(12) United States Patent
Hareyama et al.

(10) Patent No.: US 6,381,483 B1
(45) Date of Patent: Apr. 30, 2002

(54) THERAPEUTIC SYSTEM

(75) Inventors: Norihiko Hareyama, Hachioji; Toru Nagase, Hoya; Shinji Hatta, Hachioji, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/266,310

(22) Filed: Mar. 11, 1999

(30) Foreign Application Priority Data

Mar. 25, 1998 (JP) ............................................ 10-077231

(51) Int. Cl.[7] ................................................ A61B 5/05
(52) U.S. Cl. ........................ 600/407; 600/411; 600/427
(58) Field of Search ................................ 600/407, 411, 600/427, 424, 439, 473, 476, 478, 109, 117, 118, 160; 606/130; 378/62, 65; 601/2–4

(56) References Cited

U.S. PATENT DOCUMENTS 5,188,111 A * 2/1993 Yates et al. .................. 604/281
5,435,304 A * 7/1995 Oppelt et al. ................ 600/439
5,553,618 A * 9/1996 Suzuki et al. ................ 600/407
5,682,890 A   11/1997 Kormos et al.
5,897,495 A * 4/1999 Aida et al. ................... 600/411
5,899,857 A * 5/1999 Wilk ........................... 600/407
6,128,522 A * 10/2000 Acker et al. ................. 600/411

* cited by examiner

Primary Examiner—Brian L. Casler
(74) Attorney, Agent, or Firm—Frishauf, Holtz, Goodman, Langer & Chick, P.C.

(57) ABSTRACT

A therapeutic system comprising a therapeutic applicator for treating living tissues and an observation unit for determining the position of the applicator. The therapeutic energy applied from the applicator to the living tissues is controlled in accordance with data representing the position of the applicator, determined by the observation unit. It is therefore easy to operate the system even if the applicator and the observation unit (e.g., an MRI apparatus) are used at the same time. The image of the living tissues remains clear during the use of the therapeutic applicator.

5 Claims, 40 Drawing Sheets

THERAPEUTIC SYSTEM

BACKGROUND OF THE INVENTION

The present invention relates to a therapeutic system comprising a medical applicator to be inserted into a living body and an observation means such as an MRI (Magnetic Resonance Imaging) apparatus.

Generally, a therapeutic system comprises a medical applicator such as a high-frequency instrument and an observation means such as an MRI apparatus. Before the medical applicator is inserted into a patient, the affected tissue within the patient, to which the applicator should be guided, is detected by the observation means. The medical applicator is inserted into the patient and guided to the affected tissue. The applicator is operated, thereby effectively performing high-frequency treatment on the affected tissue.

In the conventional medical system, the applicator and the observation means are driven independently of each other. To drive the applicator and the observation means at the same time, they must be simultaneously controlled, while being observed. Simultaneous control of the medical applicator and the observation means is troublesome.

To make matters worse, the noise in the electro-magnetic waves emitted from the applicator may distort the image generated by the observation means (e.g., MRI device). The image of the affected tissue may be also distorted to become unclear, while high-frequency waves are applied to the affected tissue.

BRIEF SUMMARY OF THE INVENTION

The present invention has been made in view of the foregoing. Its object is to provide a therapeutic system in which the medical applicator and the observation means (e.g., MRI apparatus) can be easily operated at the same time and in which the image generated by the observation means remains clear all the time the medical applicator is used.

To achieve the object, a therapeutic system according to the invention comprises: a therapeutic applicator adapted to be inserted into a body cavity, for applying therapeutic energy to treat living tissues present in the body cavity; observation means for indicating a position which the therapeutic applicator takes in the body cavity; and control means for controlling the therapeutic energy applied from the therapeutic applicator to the living tissues, on the basis of data representing the position which the therapeutic applicator takes in the body cavity.

During the therapy, the observation means for indicates the position the therapeutic applicator takes in the body cavity. The control means controls the therapeutic energy applied from the applicator to the living tissues, in accordance with the data representing the position of the applicator.

Hence, it is easy to operate the system even if the applicator and the observation unit (e.g., an MRI apparatus) are used at the same time. The image of the living tissues remains clear during the use of the therapeutic applicator.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
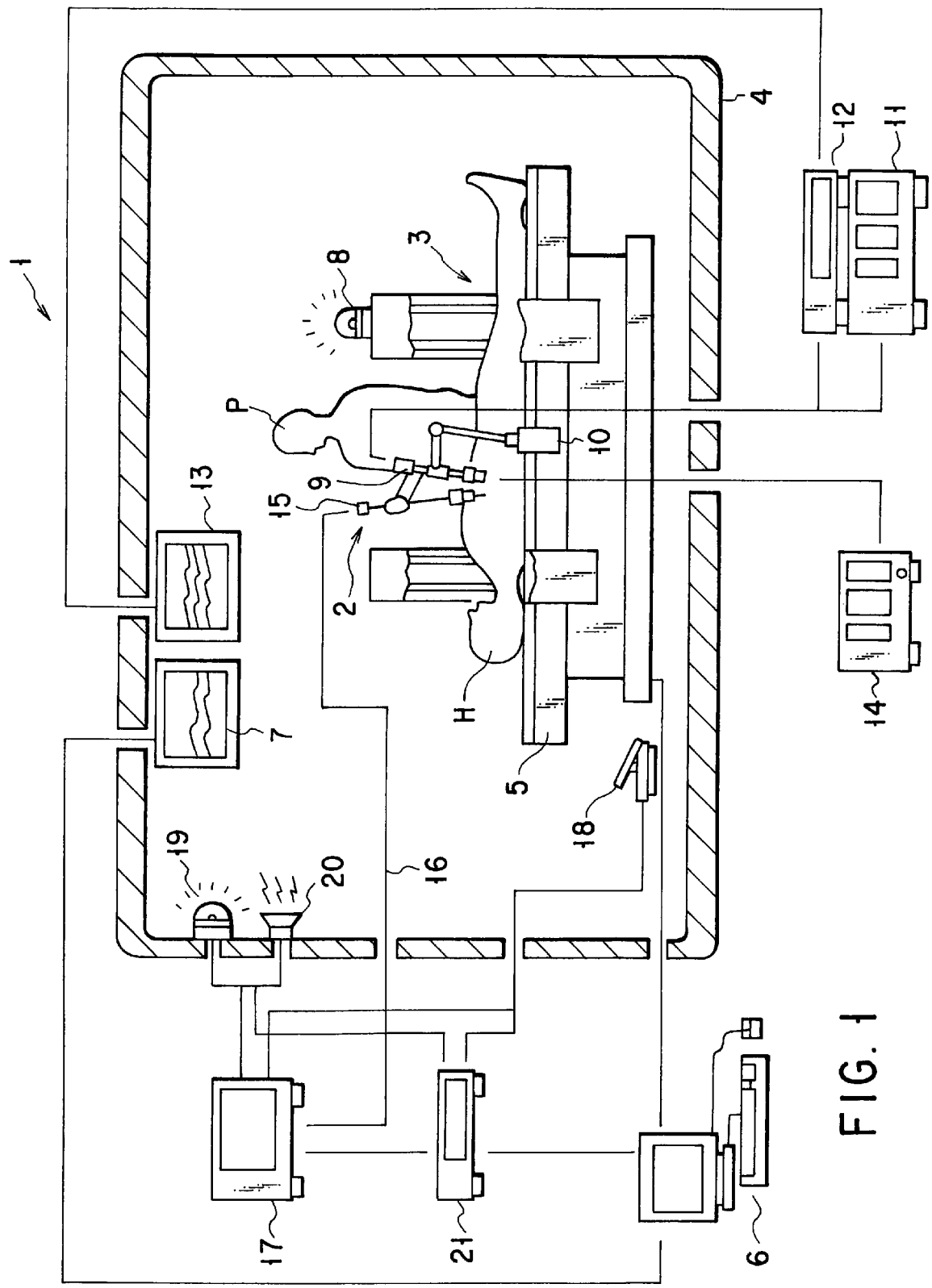
FIG. 1 is a schematic representation of a therapeutic system, which is the first embodiment of the present invention.

The first embodiment of the present invention will be described with reference to FIGS. 1 to 8. FIG. 1 shows the first embodiment, which is a therapeutic system 1. The therapeutic system 1 comprises a microwave therapeutic apparatus 2 and an MRI apparatus (observation means) 3. The microwave therapeutic apparatus 2 is designed to apply therapeutic energy to a subject to heal an affected tissue existing in the living body. The MRI apparatus 3 is designed to show MR (Magnetic Resonance) images to a doctor.

The MRI apparatus 3 has an MR gantry 5 installed in an MR inspection room 4. The MR gantry 5 is provided to support a patient H. The MR gantry 5 is connected to an MRI apparatus control section 6 located outside the MR inspection room 4.

A first monitor 7 is provided inside the MR inspection room 4 and connected to the MRI control section 6, for displaying MR images of the patient H lying on the MR gantry 5 during the MR inspection. A light 8 is mounted on a stand protruding upwardly from the gantry 5. A scope holder 10 is secured to one side of the gantry 5. The holder 10 holds an endoscope 8 (either a laparoscope 9 or an ultrasonic endoscope). The endoscope 8 is connected to a light-source device 11 and a video processor 12, both located outside the MR inspection room 4.

A second monitor 13 is provided in the MR inspection room 4. The second monitor 13 is connected to the video processor 12. To perform MR inspection on the patient H, the illumination light is applied from the light-source device 11 though the endoscope 9 into the peritoneal cavity of the patient H, which contains an affected tissue. The light reflected from everything in the peritoneal cavity is applied to the endoscope 9. The endoscope 9 forms an image of the peritoneal cavity. The video processor 12 converts the image into a video signal, which is supplied to the second monitor 13 provided in the MR inspection room 4. The second monitor 13 displays the image of the peritoneal cavity.

The therapeutic system has a pneumoperitoneal device 14. The pneumoperitoneal device 14 is driven when the endoscope 9 is used. The device 14 supplies gas into the peritoneal cavity of the patient H in order to accomplish pneumoperitoneum.

The microwave therapeutic apparatus 2 comprises a microwave applicator (medical applicator) 15. The microwave applicator 15 is connected by a microwave relay cable 16 with a microwave oscillator 17, which is located in the MR inspection room 4. A foot switch 18, an indicator lamp 19 and a speaker 20 are connected to the microwave oscillator 17, which is provided in the MR inspection room 4.

The therapeutic system further comprises a control unit (control mans) 21 for controlling the microwave therapeutic apparatus 2. The control unit 21 is arranged outside the MR inspection room 4. The microwave oscillator 17 and MRI apparatus control section 6, both located outside the room 4, are connected to the control unit 21. The foot switch 18, indicator lamp 19 and speaker 20, all located in the room 4, are also connected to the control unit 21.

Figure 2A:
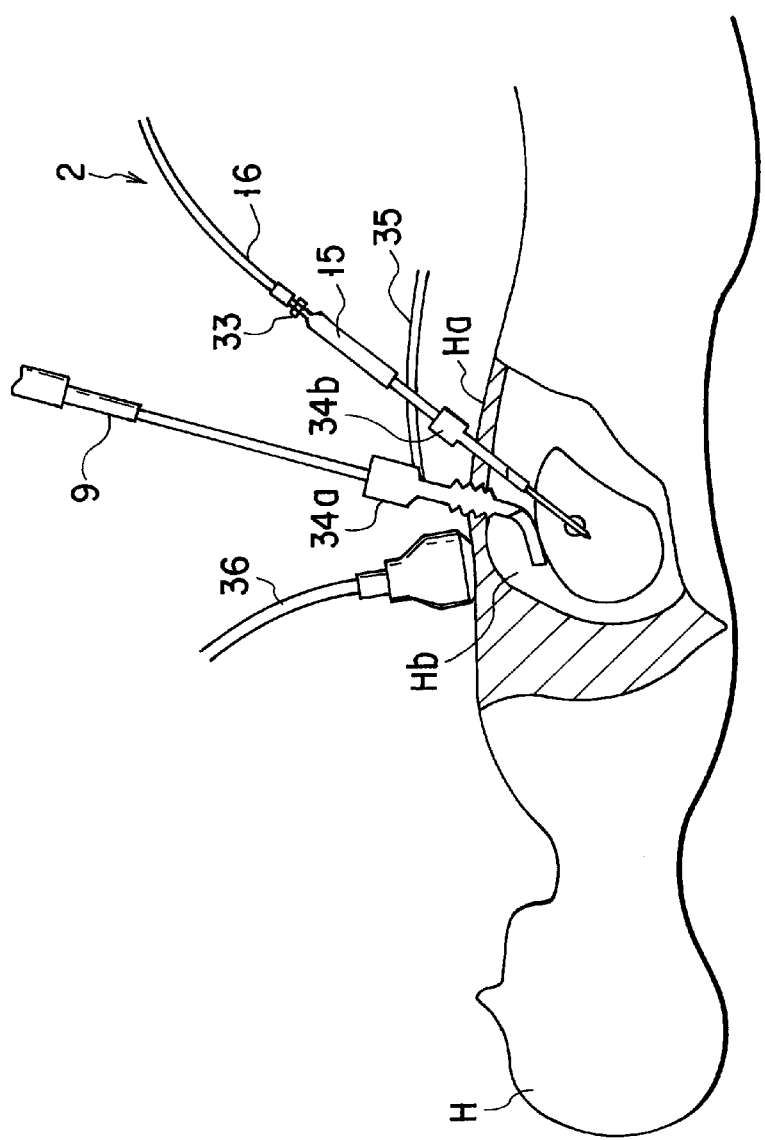
FIG. 2A is a partially sectional view of a patient, illustrating how the medical apparatus is used to perform treatment on the patient.
Figure 2B:
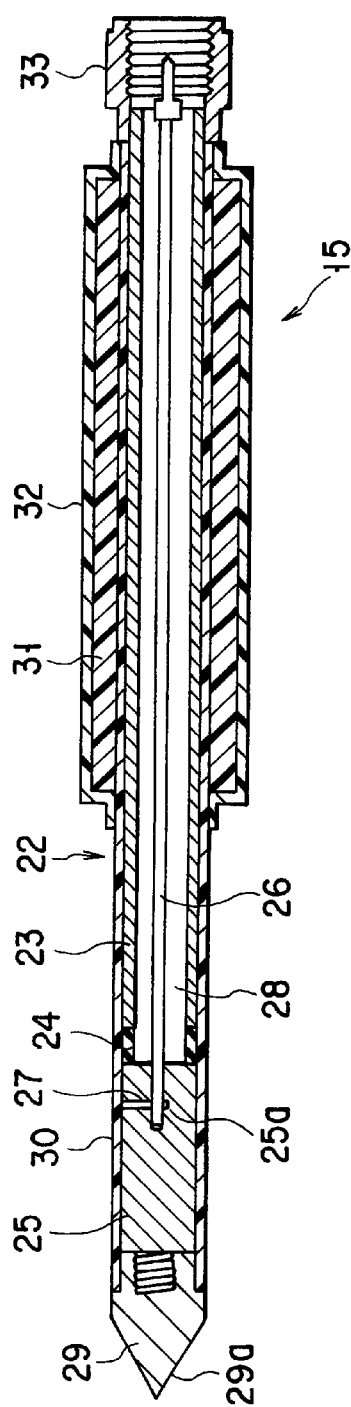
FIG. 2B is a longitudinal sectional view of the microwave applicator incorporated in the first embodiment of the invention.

The microwave applicator 15 has a rod-shaped main body 22 that is shown in FIG. 2B. The man body 22 comprises a conductor 23, an insulator 24, and a distal conductor 25. The outer conductor 23 and the insulator 24 are hollow cylinders, whereas the distal conductor 25 is a solid cylinder. The conductors 23 and 25 and the insulator 24 have substantially the same diameter. They are connected together in axial alignment, with the insulator 24 interposed between the conductors 23 and 25. The microwave applicator 15 has an MW (Microwave) antenna, the center part of which is arranged in the insulator 24.

An inner conductor 26, which is a thin rod, extends through the outer conductor 23 and the insulator 24 in axial alignment therewith. The distal part of the inner conductor 26 is inserted into the axial hole made in the distal conductor 25. The distal conductor 25 has a radial hole 25a that communicates with the axial hole. The radial hole 25a is filled with solder, which functions as an MR marker 27 to be used in magnetic resonance imaging (MRI). The solder holds the distal part of the inner conductor 26 firmly and steadily in the axial hole of the distal conductor 25, while electrically connecting the inner conductor 26 to the distal conductor 25. The annular space defined by the outer conductor 23, insulator 24 and inner conductor 26 is filled with a dielectric body 28.

A distal tip 29 is set in screw engagement with the distal conductor 25. The distal end of the tip 29 is shaped like a corn, forming a sharp piercing part 29a.

The main body 22 of the microwave applicator 15 has its outer circumferential surface covered with a transparent layer 30 made of fluororesin. A resin cylinder 31, which serves as a grip, is mounted on the proximal end portion of the main body 22. The outer circumferential surface of the resin cylinder 31 is covered with a resin coating 32.

A coaxial connector 33 is coupled to the proximal end of the main body 22. The microwave relay cable 16 can be connected to the coaxial connector 33 as is shown in FIG. 2A.

Figure 8:
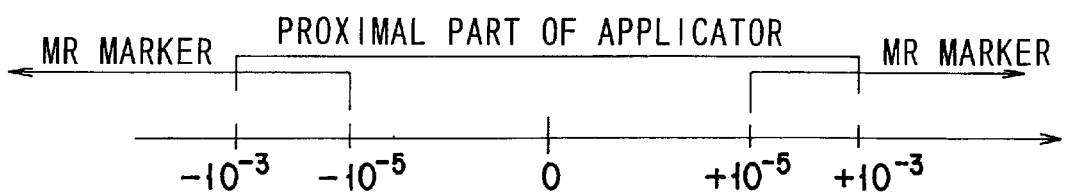
FIG. 8 is a diagram illustrating the range of magnetic susceptibility for the main body of the microwave applicator, and also the range of magnetic susceptibility for the MR marker formed in the main body.

The outer conductor 23, distal conductor 25 and inner conductor 26 are made of material, such as Cu, which has magnetic susceptibility ranging from $-10^{-3}$ to $+10^{-3}$, as is shown in FIG. 8. The solder, which forms the MR marker 27, has magnetic susceptibility of $-10^{-5}$ or less, or $+10^{-5}$ or more. Thus, the main body 22 of the applicator 15 has an MR marker 27, which has magnetic susceptibility greater in absolute value than the magnetic susceptibility of the material of the main body 22.

Before therapy is performed on the patient H by means of the therapeutic system 1, trocars 34a and 34b are set in the abdominal wall Ha of the patient H as is illustrated in FIG. 2A. The endoscope 9 is inserted through the trocar 34a into the peritoneal cavity Hb of the patient H. The microwave applicator 15 is inserted through the trocar 34b into the peritoneal cavity Hb. An air-supplying tube 35 is connected to the trocar 34a. An ultrasonic probe 36 is placed on the abdomen of the patient H to apply ultrasonic waves into the peritoneal cavity Hb.

Figure 3:
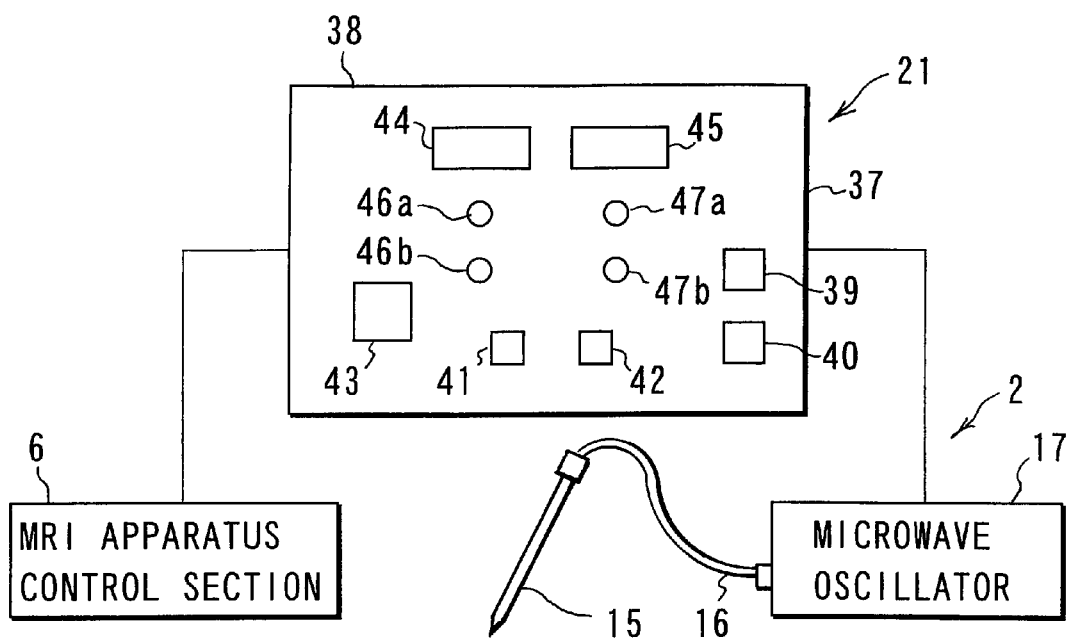
FIG. 3 is a diagrammatic view showing the connection of the control unit to some other components of the first embodiment.

As shown in FIG. 3, the control unit 21 has a unit case 37 and an operation panel 38. The operation panel 38 is provided on the unit case 37. Various switches are arranged on the operation panel 38. They are a start switch 39, a stop switch 40, a high output switch 41, a low output switch 42, an MRI start switch 43, a high output display 44, a low output display 45, high-output setting switches 46a and 46b, and low-output setting switches 47a and 47b.

Figure 4:
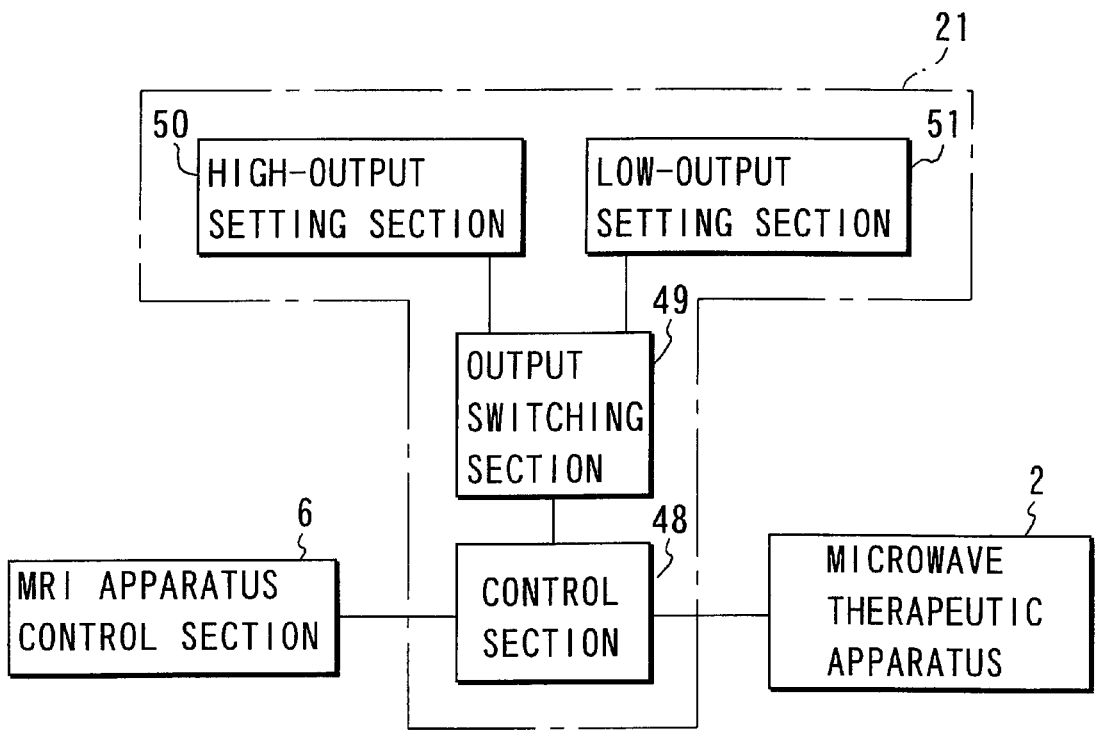
FIG. 4 is a block diagram of the control section incorporated in the first embodiment.

As shown in FIG. 4, the control unit 21 comprises a control section 48, an output switching section 49, a high-output setting section 50, and a low-output setting section 51. The high-output setting section 50 and the low-output setting sections 51 are connected to the output switching section 49. The high-output setting switches 46a and 46b are connected to the high-output setting section 50. The low-output setting switches 47a and 47b are connected to the low-output setting sections 51.

The high output switch 41 and low output switch 42 are connected to the output switching section 49. The start switch 39, stop switch 40, MRI start switch 43, high output display 44 and low output display 45 are connected to the control section 48.

The operation of the therapeutic system 1 will be described. First, the patient H is laid on the MR gantry 5 provided in the MR inspection room 4, as is illustrated in FIG. 1. Then, as shown in FIG. 2A, trocars 34a and 34b are set in the abdominal wall Ha of the patient H. The insertion section of the endoscope 9 is inserted into the peritoneal cavity Hb of the patient H through the trocar 34a, and the microwave applicator 15 is inserted into the peritoneal cavity Hb through the trocar 34b. If necessary, the ultrasonic probe 36 is placed on the abdomen of the patient H.

Illumination light is applied from the light-source device 11 through the endoscope 9 to, for example, the affected tissue presents in the peritoneal cavity Hb of the patient H. The endoscope 9 forms an image of the peritoneal cavity Hb. The video processor 12 converts the image into a video signal. The video signal is supplied to the second monitor 13 provided in the MR inspection room 4. The second monitor 13 displays the endoscopic image of the peritoneal cavity Hb.

Figure 6:
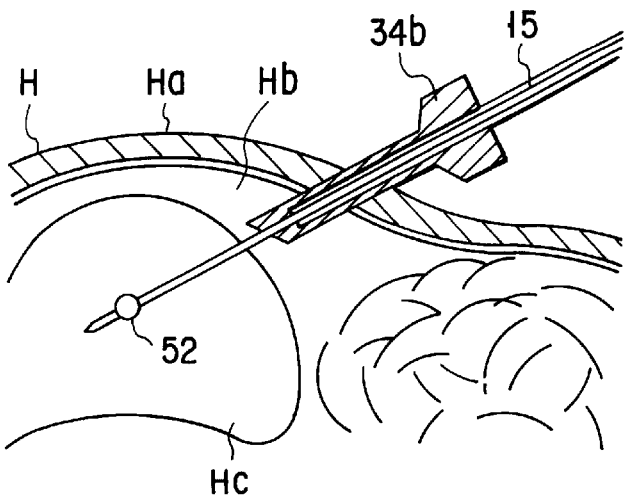
FIG. 6 is a longitudinal sectional view of the patient, showing the applicator of the first embodiment, which is inserted into the peritoneal cavity of the patient.
Figure 7:
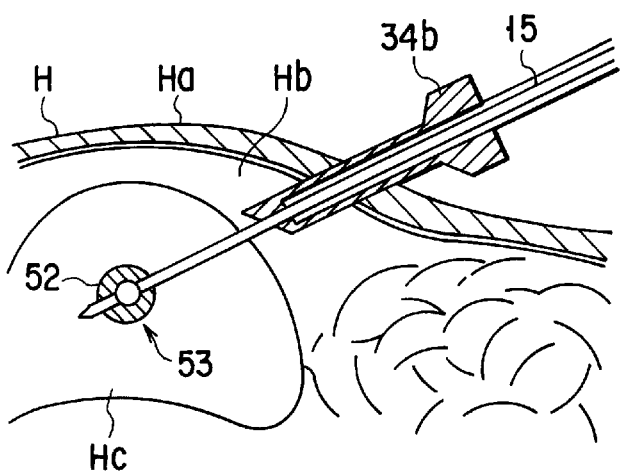
FIG. 7 is a longitudinal sectional view of the patient, showing an MR image of the region of the affected tissue, which is being coagulated by the microwave applicator of the first embodiment.

During MR inspection, the first monitor 7 provided in the MR inspection room 4 displays an MR image of the patient H lying on the MR gantry 5. The first monitor 7 displays the image of the microwave applicator 15, too, as shown in FIGS. 6 and 7. In FIGS. 6 and 7, Hc indicates the liver of the patient, 52 denotes the artifact resulting from the MR marker 27, and 53 designates the region coagulated when the microwave applicator 15 applies microwaves to the affected tissue.

In the present embodiment, the control unit 21 is operated, setting the output of the microwave applicator 15, before the microwave applicator 15 is used. The output of the microwave applicator 15 can be set at two values, i.e., high and low. The high output is set when the high-output setting switches 46a and 46b are pushed. The low output is set when the low-output setting switches 47a and 47b are pushed. The high output is selected when the high output switch 41 is pushed, and the low output is selected when the low output switch 42 is pushed. Alternatively, the high output and the low output may be switched from one to the other, every time an output-changeover switch (not shown) is pushed.

After the output has been set for the microwave applicator 15, the start switch 39 of the control unit 21 is depressed. Then, the control unit 21 transmits an output start signal to the microwave therapeutic apparatus 2. At the same time, the control unit 21 transmits a control signal to the microwave therapeutic apparatus 2. The control signal corresponds to the output value set in the control unit 21. Upon receipt of the output start signal, the microwave therapeutic apparatus 2 starts operating, whereby the microwave applicator 15 applies microwaves to the affected tissue present in the peritoneal cavity Hb. Thus, microwave therapy is started.

During the microwave therapy, the control unit 21 transmits a control signal to the microwave therapeutic apparatus 2, controlling the output of the apparatus 2. At the same time, the control unit 21 transmits an MRI start signal to the MRI apparatus 3. In response to the MRI start signal, the MRI apparatus 3 starts generating an MR image of the patient H. The output signal from the MRI apparatus control section 6 is input to the control section 48 of the control unit 21, whereby the MRI apparatus 3 provides an MR image that indicates the position of the microwave applicator 15.

The data representing the position of the microwave applicator 15 is supplied to the control unit. 21. In accordance with this data the control unit 21 controls the output of the microwave applicator 15, i.e., the therapeutic energy to be applied from the applicator 15 to the affected tissue existing in the peritoneal cavity Hb.

Figure 5:
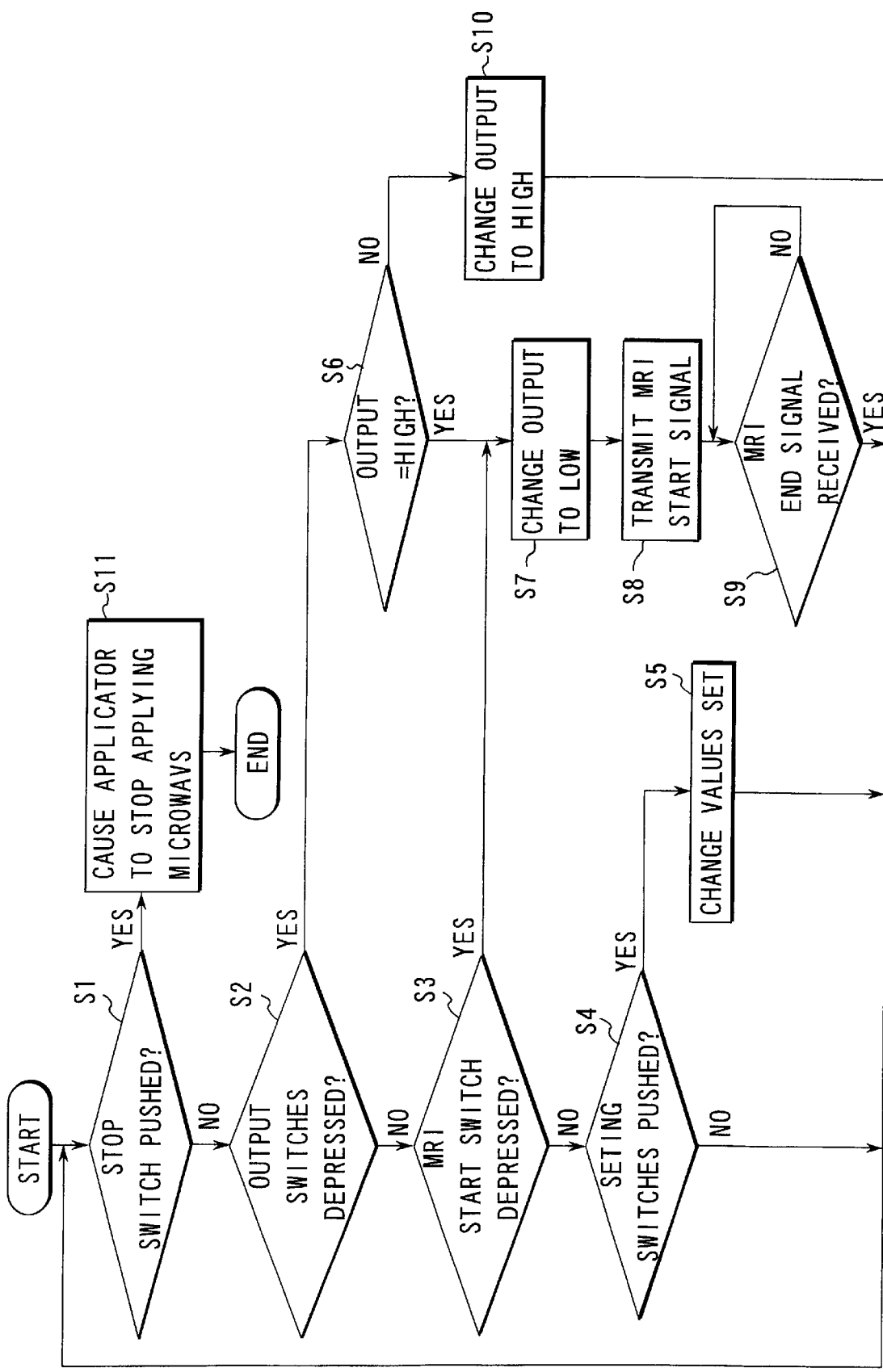
FIG. 5 is a flow chart explaining the operation of the first embodiment of the invention.

How the control unit 21 controls the microwave applicator 15 will be explained, with reference to the flow chart of FIG. 5.

First, it is determined in Step S1 whether the stop switch 40 has been pushed or not. If NO in Step S1, the operation goes to Step S2. In Step S2, it is determined whether the high output switch 41 and low output switch 42 of the output-switching section 49 have been depressed or not. If it is determined that neither the switch 41 nor the switch 42 has been depressed, the operation goes to Step S3.

In Step S3, it is determined whether the MRI start switch 43 has been depressed or not. If NO in Step S3, the operation goes to Step S4.

In Step S4, it is determined whether the setting switches (i.e., high-output setting switches 46a and 46b and low-output setting switches 47a and 47b) have been pushed or not. If YES in Step S4, the operation goes to Step S5. In Step S5, the various values set are changed. The operation then returns to Step S1. If NO in Step S4, the values set are not changed, and the operation returns to Step S1.

If YES in Step S2, that is, if the output switch 41 or the output switch 42, or both switches 41 and 42 have been pushed, the operation goes to Step S6. In Step S6, it is determined whether the microwave output of the microwave oscillator 17 is high or not. If YES in Step S6, the operation goes to Step S7.

In Step S7, the microwave output of the microwave oscillator 17 is changed to low. Then, in Step S8, the control unit 21 transmits an MRI start signal to the MRI apparatus 3. Thus, the microwave therapeutic apparatus 2 is controlled such that the output of the oscillator 17, if high, is changed to low when the MRI start switch 43 is pushed while the microwave applicator 15 is applying microwaves to the affected tissue. The control unit 21 then transmits an MRI start signal to the MRI apparatus 3.

After the control unit 21 transmits an MRI start signal to the MRI apparatus 3 in Step S8, the operation goes to Step S9. In Step S9 it is determined whether or not the control unit 21 has received an MRI end signal from the MRI apparatus 3. Step S9 is repeated until it is determined that the unit 21 has received an MRI end signal. If YES in Step S9, the operation returns to Step S1. Hence, after the completion of the MR imaging, the output of the microwave oscillator 17 remains not changed to high until the control unit 21 receives an MRI end signal from the MRI apparatus 3.

If NO in Step S6, that is, if the microwave output of the microwave oscillator 17 is not high, the operation goes to Step S10. In Step S10 the microwave output of the microwave oscillator 17 is changed to high. The operation then returns to Step S1.

When the stop switch 40 is pushed while the microwave therapeutic apparatus 2 is operating, it is determined in Step S1 that the stop switch 40 has been depressed. In this case, the operation goes to Step S11. In Step S11, the control unit 21 transmits an output stop signal to the microwave therapeutic apparatus 2. In response to the output stop signal, the apparatus 2 stops operating. As a result, the microwave applicator 15 ceases to apply microwaves to the affected tissue existing in the peritoneal cavity Hb. The microwave therapy is thereby terminated.

If NO in Step S1, that is, if it is determined that the stop switch 40 has not been pushed, either the high output switch 41 or the output-changeover switch (not shown) may be depressed after the MR imaging has completed. In this case, the microwave therapeutic apparatus 2 is controlled to change the output of the microwave oscillator 17 to high.

The low output switch 42 may be pushed while the output of the microwave oscillator 17 remains high, thus changing the output of the oscillator 17 to low. Alternatively, the stop switch 40 may be pushed while the output of the microwave oscillator 17 remains high, thereby causing the oscillator 17 to stop generating microwaves. In either case, the control unit 21 transmits an MRI start signal to the MRI apparatus 3.

The therapeutic system 1 described above, i.e., the first embodiment of the invention, is advantageous in the following respects.

When the microwave therapeutic apparatus 2 and the MRI apparatus 3 are used simultaneously, the output of the microwave applicator 15, i.e., the energy applied to the affected tissue, is automatically decreased. The noise in the electromagnetic waves applied from the applicator 15 imposes on the MRI image generated by the MRI apparatus 3 can therefore be minimized. The MRI image of the peritoneal cavity Hb, showing the affected tissue, is sufficiently clear even while the microwave therapeutic apparatus 2 is being used. Further, therefore may be also distorted to become unclear, while high-frequency waves are applied to the affected tissue. Since the MRI image is not blurred, showing the affected tissue somewhat larger than it is, there is no possibility that microwaves are applied to anything existing around the affected tissue.

In the first embodiment, the microwave therapeutic apparatus 2 can continuously perform microwave therapy, while the MR imaging is being effected. It is therefore possible to prevent the temperature of the living tissue from falling during the MR imaging. This helps to accomplish effective therapy.

Further, it is easy to operate the microwave therapeutic apparatus 2 and the MRI apparatus 3 at the same time. This is because the control unit 21 automatically decreases the output of the microwave applicator 15 (i.e., the energy applied to the affected tissue) while the MRI apparatus 3 is performing MR imaging.

Still further, the main body 22 of the microwave applicator 15 is electrically insulated reliably and is biologically adapted, because the outer surface of the main body 22 is covered with a transparent layer 30 made of fluororesin. In addition, no living tissues will stick to the main body 22 of the applicator 15 when the microwave applicator 15 is used to cauterize the affected tissue.

In the first embodiment, the solder, forming the MR marker 27, electrically connects the distal part of the inner conductor 26 to the distal conductor 25. Hence, the artifact 52 resulting from the MR marker 27 located before the center of the MW antenna of the applicator 15 can be shown in the MR image as shown in FIG. 6. The artifact 52 thus shown serves to locate the center of the MW antenna, from which therapeutic energy is emitted. This helps to enhance the operability of the microwave applicator 15 and the safety and reliability of the microwave therapy. Moreover, the microwave applicator 15 is easy to assemble since the MR marker 27 is located in front of the center part of the MW (Microwave) antenna, which is arranged in the insulator 24.

The MRI apparatus 3, which serves as means for determining the position of the microwave applicator 15, may be replaced by an ultrasonic imaging apparatus or an X-ray CT (Computed Tomography) apparatus. Furthermore, the microwave therapeutic apparatus 2, which is used as the therapeutic apparatus, may be replaced by a laser apparatus, a RF therapeutic apparatus, an HF therapeutic apparatus, or an ultrasonic-wave apparatus. Moreover, a tissue-separating current may be supplied to the microwave applicator 15 for a short time when the stop switch 40 is pushed at the end of the microwave therapy. Still further, a graduation may be printed on the microwave applicator 15 so that the doctor may know how deep the applicator 15 has been inserted into the peritoneal cavity Hb, by reading the graduation shown in the RM image of the patient H.

The therapeutic system 1, which is the first embodiment of the invention, comprises a therapeutic applicator for applying therapy to a living tissue and an observation means for determining the position of the applicator. The energy applied from the applicator to the living tissue is controlled in accordance with the data representing the position of the applicator. Hence, it is easy to operate the therapeutic applicator and the observation means, such as an MRI apparatus, at the same time. Further, the observation means provides a clear MR image of the patient while the therapeutic applicator is being used.

Figure 9:
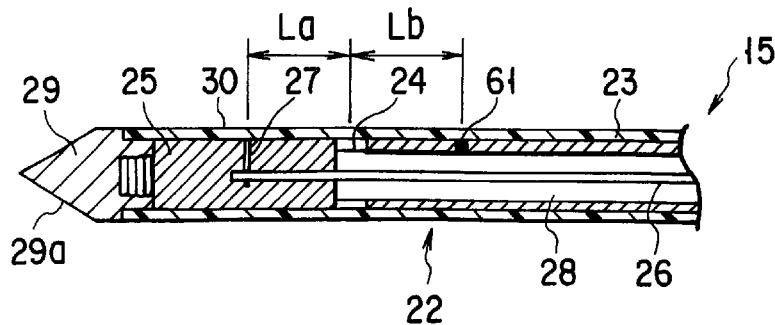
FIG. 9 is a longitudinal sectional view of the distal portion of the microwave applicator provided in a therapeutic system, which is the second embodiment of the present invention.
Figure 10:
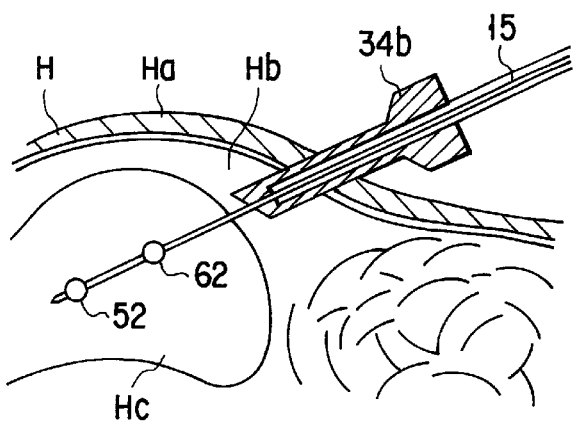
FIG. 10 is a longitudinal sectional view of the patient, showing the applicator of the second embodiment, which is inserted into the peritoneal cavity of the patient.
Figure 11:
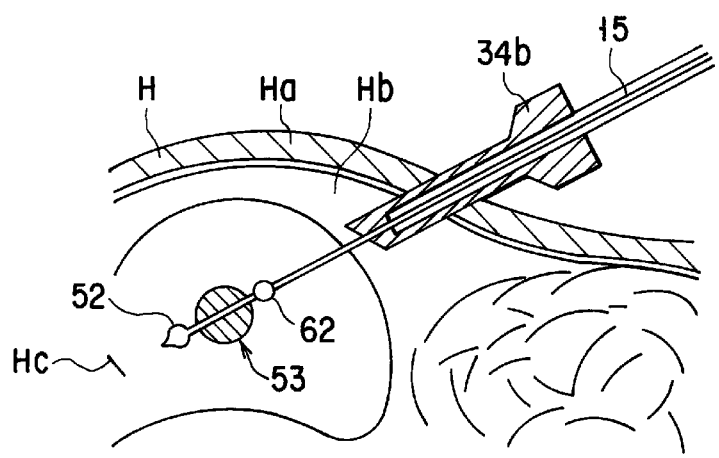
FIG. 11 is a longitudinal sectional view of the patient, showing an MR image of the region of the affected tissue, which is being coagulated by the microwave applicator of the second embodiment.

FIGS. 9 to 11 show the second embodiment of the present invention. The second embodiment is identical to the first embodiment (FIGS. 1 to 8), except for the structure of the microwave applicator 15.

As shown in FIG. 9, the microwave applicator 15 has two MR markers 27 and 61. The first MR marker 27 of the same type as the one used in the first embodiment is arranged at a position which is distal to the center part of the MW antenna (i.e., the center part of the insulator 24) of the applicator 15. The second MR marker 61, which is made of solder, is arranged at a position, which is proximal to the center part of the MW antenna.

The distance La between the first MR marker 27 and the center part of the MW antenna, and the distance L2 between the second MR marker 61 and the center part of the MW antenna have relation of La>Lb, La<Lb, or La=Lb. The second MR marker 61 may be made of material other than solder, such as one having magnetic susceptibility of $-10^{-3}$ or less, or $+10^{-3}$ or more.

The microwave applicator 15 has its center of energy-emission at the center part of the MW antenna, which lies between the first MR marker 27 and the second MR marker 61. Therefore, two artifacts 52 and 62 will appear in an MR image that has been generated by the MRI apparatus 3, as is illustrated in FIG. 10.

The second embodiment is advantageous in some respects. As shown in FIG. 11, neither the artifact 52 nor the artifact 62 conceals the image of an affected tissue that is treated with microwave (i.e., coagulated region 53). This is because the center of energy-emission (i.e., center part of the MW antenna) is located between the first MR marker 27 and second MR marker 61, both made of solder and resulting in the first artifact 52 and second artifact 62, respectively. As a result, how the living tissue is coagulated can be clearly observed. This enables the doctor to know how the living tissue changes, from the beginning of the microwave therapy he or she is performing by the use of the microwave applicator 15. The safety of the microwave therapy can therefore be enhanced.

Figure 12:
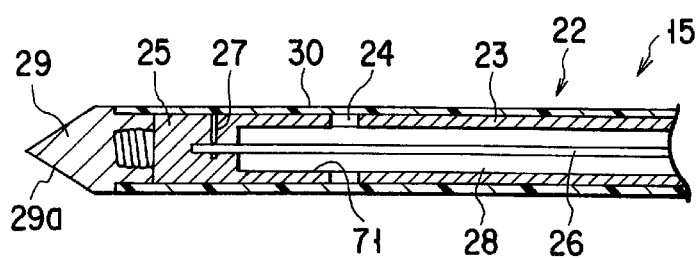
FIG. 12 is a longitudinal sectional view of the distal portion of the microwave applicator provided in a therapeutic system, which is the third embodiment of the present invention.

FIG. 12 shows the microwave applicator 15 incorporated in a therapeutic system according to the third embodiment of the invention. The third embodiment differs from the first embodiment (FIGS. 1 to 8) in the structure of the microwave applicator 15. As FIG. 12 shows, the distal conductor 25 has an axial hole 71 made in its proximal end part. The hole 71 communicates with the interior of the outer conductor 23, which is a hollow cylinder. The distal end part of the dielectric body 28 is inserted in the axial hole 71.

The distal end part of the dielectric body 28, which is inserted in the axial hole 71 renders the distal conductor 25 more rigid than in the case where only the distal part of the inner conductor 26 supports the distal conductor 25 as in the first embodiment. Ultimately, the dielectric body 28 serves to strengthen the junction between the distal conductor 25 and the insulator 24, which are relatively fragile.

Figure 13:
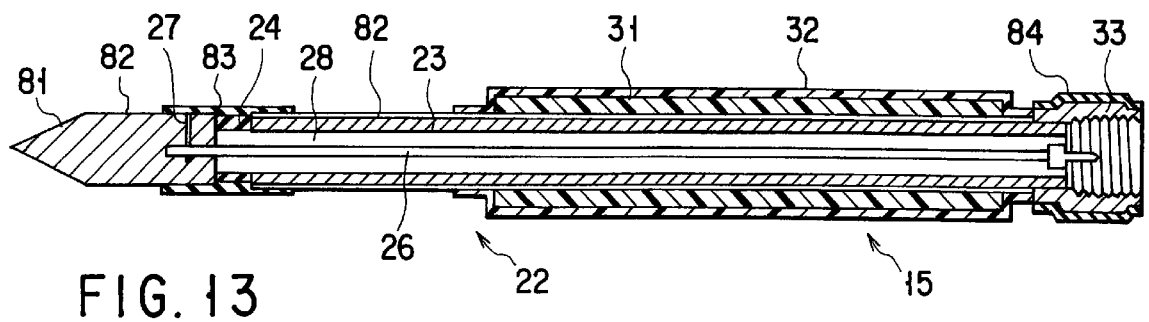
FIG. 13 is a longitudinal sectional view of the microwave applicator incorporated in a therapeutic system, which is the fourth embodiment of this invention.

FIG. 13 shows the microwave applicator 15 incorporated in a therapeutic system, which is the fourth embodiment of the invention. The fourth embodiment differs from the first embodiment (FIGS. 1 to 8) in the structure of the microwave applicator 15. As FIG. 13 shows, the microwave applicator 15 has a distal conductor 81, instead of the distal conductor 25 and the distal tip 29. Further, a titanium coating 82, instead of the transparent layer 30 made of fluororesin, covers the distal conductor 81 and the outer conductor 23.

An insulating sheath 83 is mounted on the proximal part of the distal conductor 81, the insulator 24, and the distal part of the outer conductor 23. An insulating cover 84 is mounted on the outer circumferential surface of the coaxial connector 33.

The titanium coating 82 can be thinner than the fluoreresin layer 30 to have the same strength. Hence, the main body 22 of the microwave applicator 15 can have a smaller outer diameter than its counterpart of the first embodiment. In addition, MR markers can be made of the titanium coating 83 covering the distal conductor 81 and the outer conductor 23.

Figure 14:
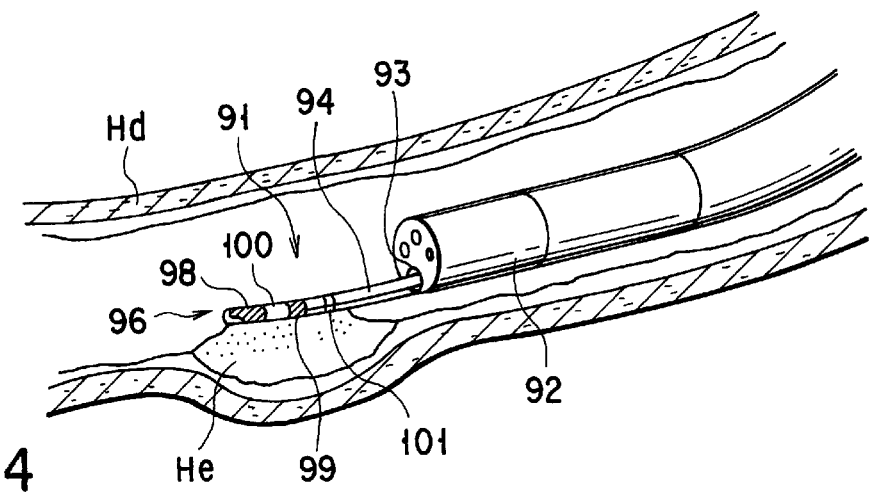
FIG. 14 is a perspective view showing the insertion section of an endoscope and a applicator incorporated in a therapeutic system according to the a fifth embodiment of the invention.
Figure 15:
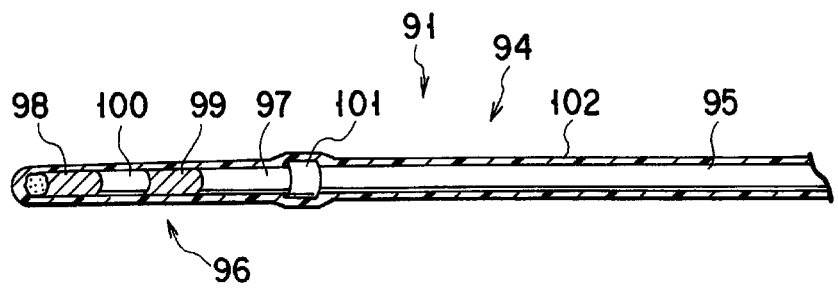
FIG. 15 is a perspective view of the applicator incorporated in the fifth embodiment.

FIGS. 14 and 15 depict the flexible applicator 91 incorporated in a therapeutic system, which is the fifth embodiment of the present invention. The flexible applicator 91 is designed for accomplishing therapy on affected tissues in the esophageal veins, the bile duct, or the like.

As shown in FIG. 14, the flexible applicator 91 has an elongated insertion section 94. The insertion section 94 comprises a flexible coaxial cable 95, an MW antenna 96, and an insulating sheath 97. The insertion section 94 is guided into a body cavity through the instrument channel 93 of an MR-compatible endoscope (or an MR endoscope) 92. The flexible coaxial cable 95 is provided in the insertion section 94 and comprises an inner conductor and an outer conductor surrounding the inner conductor. The MW antenna 96, which applies therapeutic energy, is connected to the distal end of the coaxial cable 95. The insulating sheath 97 covers the flexible coaxial cable 95 and the MW antenna 96.

The MW antenna 96 comprises a distal conductor 98, a proximal conductor 99, and a dielectric body 100. The distal conductor 98 is connected to the inner conductor of the coaxial cable 95. The proximal conductor 99 is connected to the outer conductor of the coaxial cable 95. The dielectric body 100 is interposed between the distal conductor 98 and the proximal conductor 99.

An MR marker 101 is provided on the distal part of the flexible coaxial cable 95, at a position proximal to the MW antenna 96. A sheath 102 made of fluororesin is mounted on the entire insertion section 94 of the flexible applicator 91.

To use the flexible applicator 91, the insertion section of the MR-compatible endoscope 92 is inserted into a tubular cavity, e.g., the esophagus Hd, of the patient. The distal end of the insertion section is guided to the vicinity of the affected tissue, e.g., phlebeurysm He, existing in the esophagus Hd. Then, the insertion section 94 of the flexible applicator 91 is inserted into the esophagus Hd through the instrument channel 93 of the MR-compatible endoscope 92. The doctor can set the MW antenna 96 at a desired position with respect to the surface of the esophagus Hd, referring to the position of the MR marker 101 on the flexible applicator 91. Once set so, the MW antenna 96 can coagulate or cauterize the phlebeurysm He efficiently.

The fifth embodiment described above is advantageous in that the MW antenna 96, i.e., the means for emitting therapeutic energy, can be easily located. This is because the ring-shaped MR marker 101 is provided on the distal part of the insertion section 92 of the flexible applicator 91, at a position proximal to the MW antenna 96. The doctor can therefore correctly place the MW antenna 96 at a desired position with respect to the surface of the tubular cavity. Once set so, the MW antenna 96 can coagulate or cauterize the affected tissue present in the tubular cavity. Thus, the operability of the microwave applicator 15 and the safety and reliability of the microwave therapy can be enhanced. As a result, even if either coagulation or necrosis is induced in the thin wall of a tubular organ, necrosis or deciduation of the tissue will occur, and no pits will be formed in the wall of the tubular organ.

Figure 16:
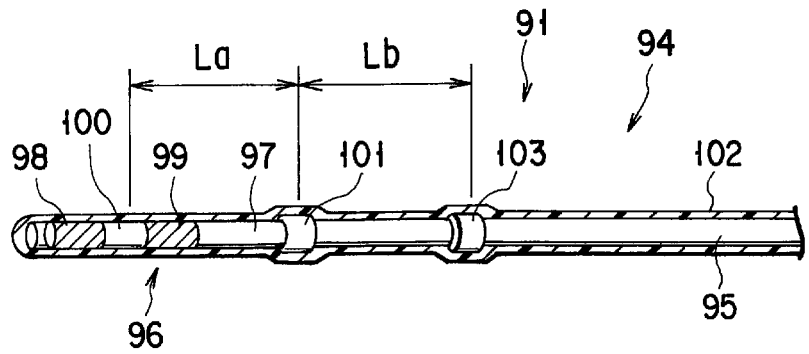
FIG. 16 is a longitudinal sectional view of the applicator provided in a therapeutic system according to the sixth embodiment of the invention.

FIG. 16 shows the flexible applicator 91 incorporated in a therapeutic system, which is the sixth embodiment of the present invention. The flexible applicator 91 differs from its counterpart of the fifth embodiment, as will be described below.

In the fifth embodiment, one the ring-shaped MR marker 101 is provided on the distal part of the insertion section 94 of the flexible applicator 91, at a position proximal to the MW antenna 96. In the sixth embodiment, a second MR marker 103 is arranged at the rear of the ring-shaped MR marker 101. The dielectric body 100 is the middle part of the MW antenna 96 that applies microwave to coagulate or cauterize the affected tissue in the wall of the tubular organ. The distance La between the body 100 and the front MR marker 101 is equal to the distance Lb between the front MR marker 101 and the second MR marker 103. While the flexible applicator 91 is being used, the position of the dielectric body 100 can be inferred from the distance Lb between the MR marker 101 and 103.

In the sixth embodiment, the second MR marker 103 is located at the back of the MR marker 101 which is identical to its counter part of the fifth embodiment, and the distance La is equal to the distance Lb (La=Lb). Hence, it is easier for a doctor to locate the dielectric body 100 that is the center of energy-emission.

Figure 17:
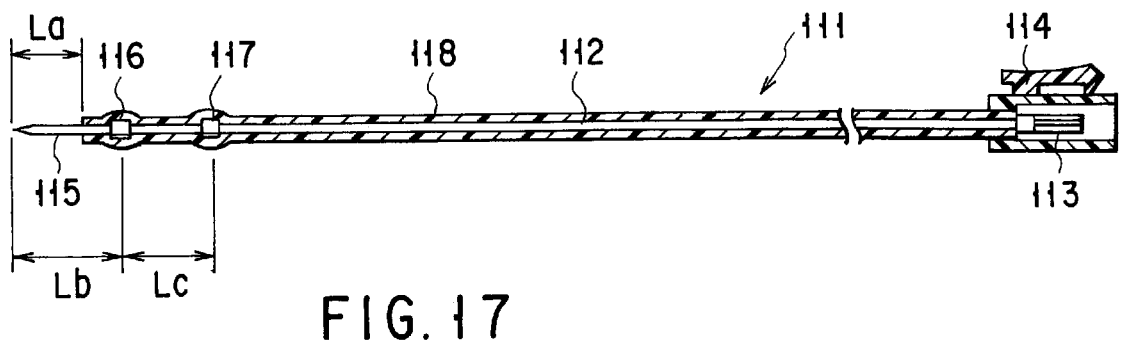
FIG. 17 is a longitudinal sectional view of the applicator incorporated in a therapeutic system according to the seventh embodiment of the invention.

FIG. 17 shows the monopolar paracentetic applicator 111 incorporated in a therapeutic system that is the seventh embodiment of the invention.

The mono-polar paracentetic applicator 111 is used in combination with an electrode provided outside the patient. The applicator 111 has a needle electrode 112 made of titanium. A connector 113 is mounted on the distal part of the needle electrode 112. A connector housing 114 is mounted on the connector 113.

A needle 115 having a length La is attached to the distal end of the needle electrode 112. Two ring-shaped MR markers 116 and 117 are provided on the distal part of the electrode 112, at the back of the needle 115. The MR markers 116 and 117 are spaced apart by a distance Lc. The distance Lc is equal to the distance Lb between the tip of the needle 115 and the front MR marker 116 (Lb=Lc). The needle electrode 112 is covered with a fluororesin coating 118.

While the mono-polar paracentetic applicator 111 is being used, the position of the tip of the needle 115 attached to the distal end of the needle electrode 112 can be inferred from the distance Lc between the MR markers 116 and 117. Further, the applicator 111 may have a smaller diameter, ultimately reducing the pain the patient may have while receiving the therapy. This is possible because the needle 115 having an appropriate length La is attached to the distal end of the needle electrode 112 made of titanium.

Figure 18:
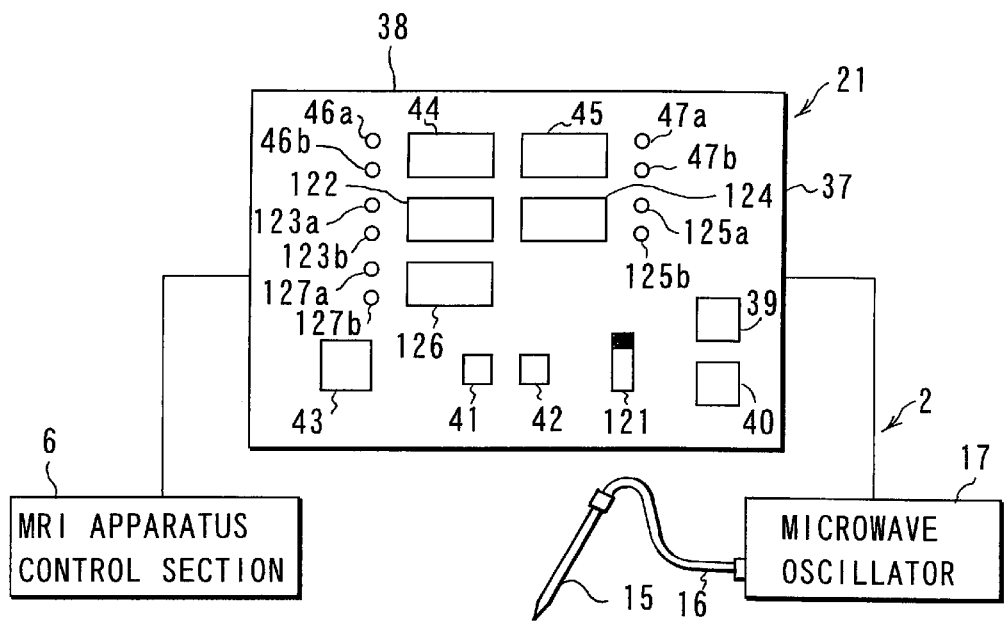
FIG. 18 is a diagrammatic view showing the connection of the control unit to some other components of a therapeutic system according to the eighth embodiment of the present invention.
Figure 19:
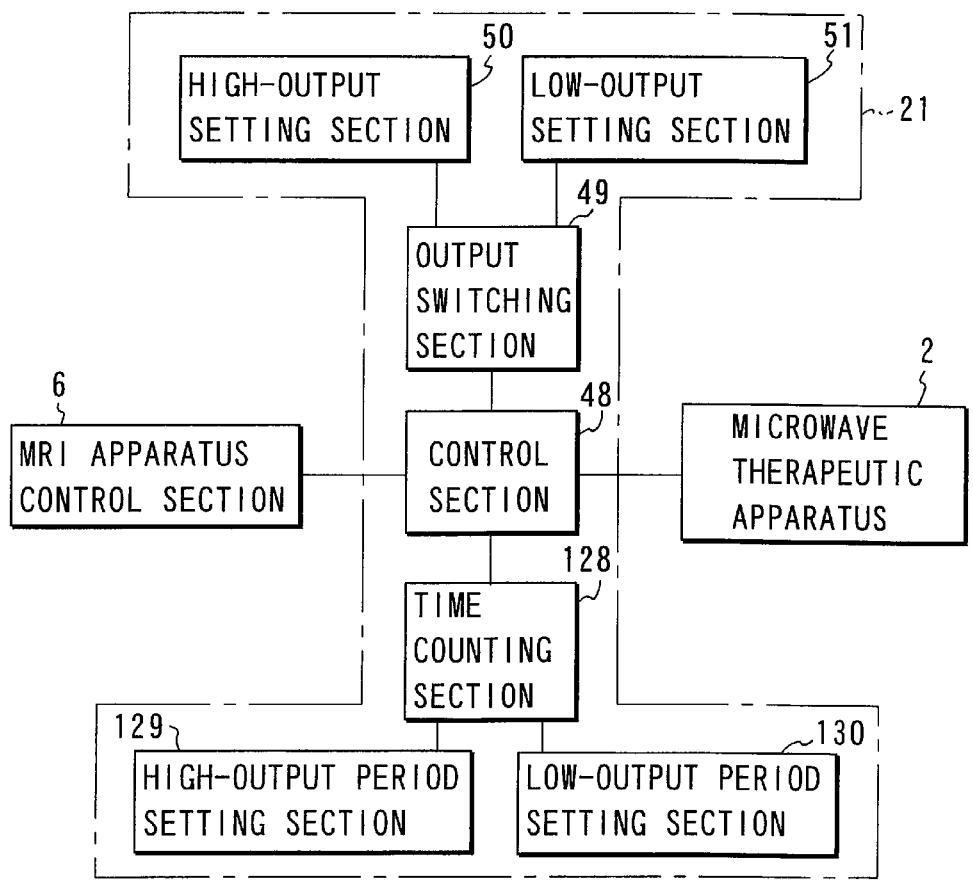
FIG. 19 is a block diagram of the control section incorporated in the eighth embodiment.
Figure 20:
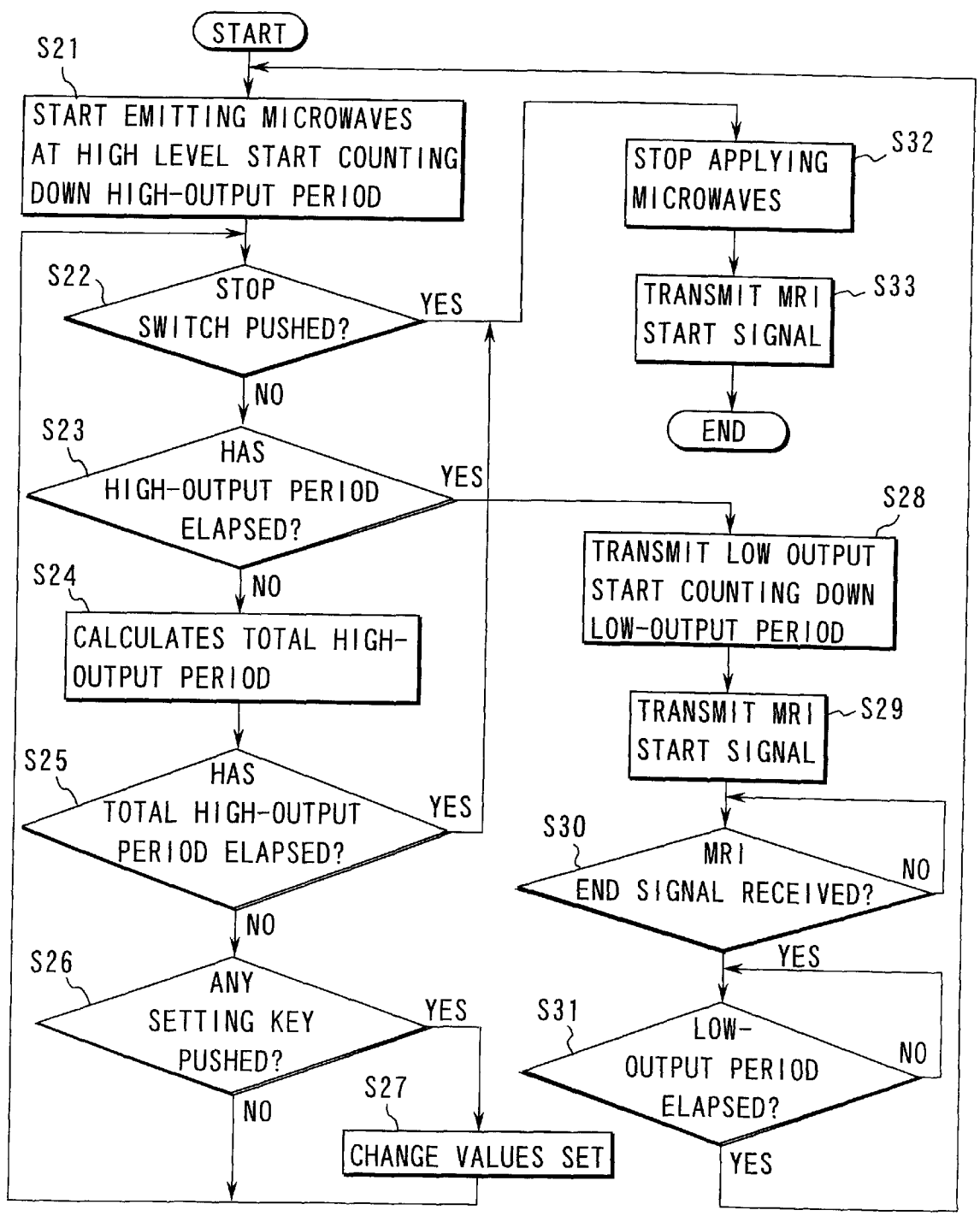
FIG. 20 is a flow chart explaining the operation of the eighth embodiment of the invention.

FIGS. 18 to 20 show a therapeutic system according to the eighth embodiment of the present invention. The eighth embodiment is identical to the first embodiment (FIGS. 1 to 8), except for the structure of the control unit 21.

As shown in FIG. 18, some additional switches and displays are provided on the operation panel 38 of the control unit 21. The additional switches are: an automatic/manual switch 121, high-output period setting switches 123a and 123b, low-output period setting switches 125a and 125b, and total high-output period setting switches 127a and 127b. The additional displays are a high-output period display 122, a low-output display 124, and a total high-output period display 126. The control unit 21 is set into automatic control mode or manual control mode by operating the switch 121. Once set in the manual mode, the control unit 21 can operate in the same way as in the first embodiment to perform various controls. Once set in the automatic control mode, the control unit 21 can perform various controls in accordance with the periods of time that have been set by operating the switches 123a, 123b, 125a, 125b, 127a and 127b.

As shown in FIG. 19, the control section 48 that is provided in the control unit 21 is connected to a time counting section 128. The time counting section 128 is connected to a high-output period setting section 129 and a low-output period setting section 130.

How the control unit 21 controls the microwave applicator 15 in the eighth embodiment will be explained.

First, the operation panel 38 of the control unit 21 is operated, setting conditions in which the applicator 15 of the microwave therapeutic apparatus 2 should be operated. More specifically, the high-output period setting switches 123a and 123b are operated, setting a high-output period for which the applicator 15 is to apply microwaves at high level. The high-output period display 122 displays the high-output period thus set. Similarly, the low-output period setting switches 125a and 125b are operated, setting a low-output period for which the applicator 15 is to apply microwaves at low level. The low-output display 124 displays the low-output period thus set. Further, the total high-output period setting switches 127a and 127b are operated, setting a total high-output period for which the applicator 15 is to apply microwaves at high level. The total high-output period display 126 displays the total high-output period.

Next, the automatic/manual switch 121 is operated, whereby the control unit 21 is set into either the automatic control mode or the manual control mode. If the control unit 2 is set into the manual control mode, the high-output period, low-output period and total high-output period set by operating the operation panel 38 will be invalidated. In this case, the control unit 21 will operate in the same way as in the first embodiment.

If the control unit 2 is set into the automatic control mode, the control unit 21 will perform various controls in accordance with the various periods set by operating the operation panel 38, as will be described with reference to the flow chart of FIG. 20.

First, the start switch 39 of the control unit 21 is depressed. The control unit 21 generates a signal representing the high-output period. This signal is supplied to the microwave therapeutic apparatus 2. The microwave applicator 15 of the therapeutic apparatus 2 starts emitting microwaves in Step S21. At the same time, the time counting section 128 starts counting down the high-output period. Then, in Step S22, it is then determined whether the stop switch 40 has been pushed or not.

If NO in Step S22, that is, if the stop switch 40 has not been pushed, the operation goes to Step S23. In Step S23, it is determined whether the high-output period has elapsed or not. If NO in Step S23, the operation goes to Step S24, in which a total high-output period is calculated. Then, in Step S25, it is determined whether the total high-output period has elapsed or not. If NO in Step S25, it is determined in Step S26 whether any setting switches have been pushed or not. If YES in Step S26, the operation goes to Step S27, in which the various values set are changed. The operation then returns to Step S22. If NO in Step S26, the operation returns directly to Step S22.

If YES in Step S23, that is, if it is determined that the high-output period has elapsed, the operation goes to Step S28. In Step S28, the low output is transmitted to the microwave therapeutic apparatus 2. The output of the apparatus 2 is thereby switched to the low value. The microwave applicator 15 of the apparatus 2 starts emitting microwaves. At the same time, the time counting section 128 starts counting down the low-output period.

Thereafter, in Step S29, the control unit 21 transmits an MRI start signal to the MRI apparatus 3. Then, in Step S30, it is determined whether or not the control unit 21 has received an MRI end signal from the MRI apparatus 3. If NO, Step S30 is repeated until the high-output period elapses. Upon lapse of the high-output period, the output of the microwave therapeutic apparatus 2 is switched to the low value, and the MRI apparatus 3 starts MRI imaging.

If YES in Step S30, that is, if it is determined that the control unit 21 has received an MRI end signal from the MRI apparatus 3, the operation goes to Step S31. In Step S31, it is determined whether the low-output period has elapsed or not. If NO, Step S31 is repeated. If YES, the operation returns to Step S21. In Step S21, the output of the microwave therapeutic apparatus 2 is switched to the high value again, only if the control unit 21 has received an MRI end signal.

The microwave applicator 15 emits high-output microwaves and low-output microwaves alternately and repeatedly. The applicator 15 stops emitting microwaves when the total high-output period set elapses. Then, the MRI apparatus 3 carries out MR imaging. Thereafter, the microwave therapy is terminated.

If YES in Step S22, that is, if it is determined that the stop switch 40 has been pushed in the course of the microwave therapy, the control unit 21 transmits an output stop signal to the microwave therapeutic apparatus 2. In response to the output stop signal, the oscillator 17 stops generating microwaves. As a result, the microwave applicator 15 ceases to apply microwaves in Step S32. Then, in Step S33, the control unit 21 transmits an MRI start signal to the MRI apparatus 3, which performs MR imaging.

In the eighth embodiment, the various output periods set by operating the operation panel 38 will be invalidated when the automatic/manual switch 121 provided on the panel 38 of the control unit 21 is operated, thereby setting the control unit 21 into the manual control mode. In this case, the control unit 21 will operate in the same way as in the first embodiment. Thus, the microwave output of the microwave oscillator 15, i.e., the therapeutic energy applied to the living tissue, is automatically decreased while both the microwave therapeutic apparatus 2 and the MRI apparatus 3 are operating at the same time, the latter performing MR imaging. The influence that the noise in the microwaves applied from the applicator 15 imposes on the MRI apparatus 3 can therefore be minimized. As a result, the image provided by the MRI apparatus 3 is sufficiently clear even while the microwave therapeutic apparatus 2 is being used.

Furthermore, once the control unit 21 has been set into the automatic control mode by operating the automatic/manual switch 121, the microwave applicator 15 automatically emit high-output microwaves and low-output microwaves alternately and repeatedly, and the MRI apparatus 3 automatically repeats the MR imaging. Hence, the eighth embodiment can achieve the same advantages as the first embodiment.

In the eighth embodiment, the MRI apparatus 3 may be replaced by an ultrasonic imaging apparatus or an X-ray CT apparatus. And the microwave therapeutic apparatus 2 may be replaced by a laser apparatus, an RF therapeutic apparatus, an HF therapeutic apparatus, or an ultrasonic-wave apparatus. Moreover, a tissue-separating current may be supplied to the microwave applicator 15 for a short time when the stop switch 40 is pushed at the end of the microwave therapy. If such a current is so supplied to the microwave applicator 15, bleeding will be prevented at the living tissue when the applicator 15 (i.e., electrode) is pulled out of the tissue after the completion of the microwave therapy.

Figure 21:
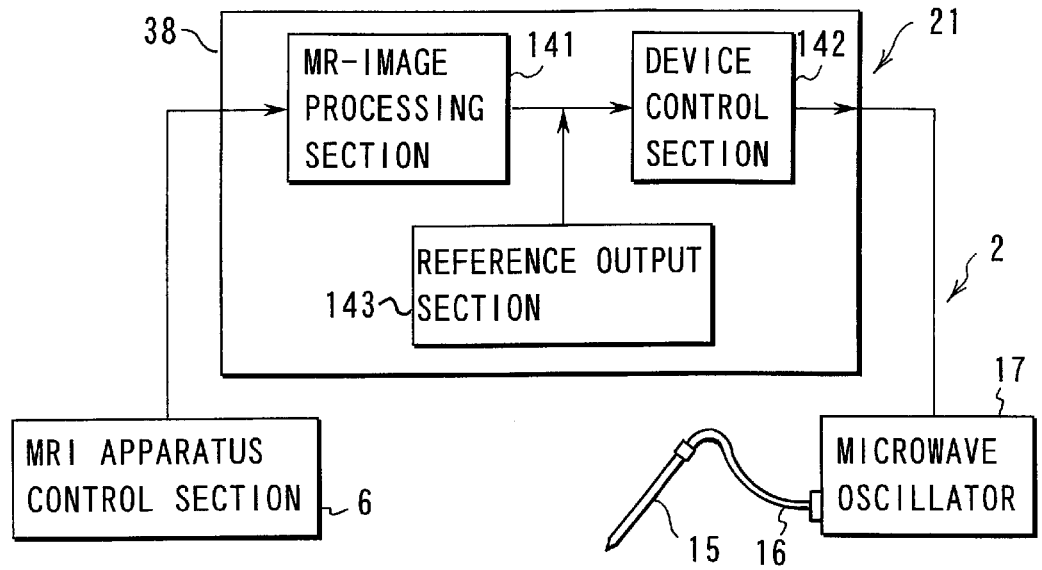
FIG. 21 is a schematic representation of a therapeutic system, which is the ninth embodiment of the present invention.
Figure 22:
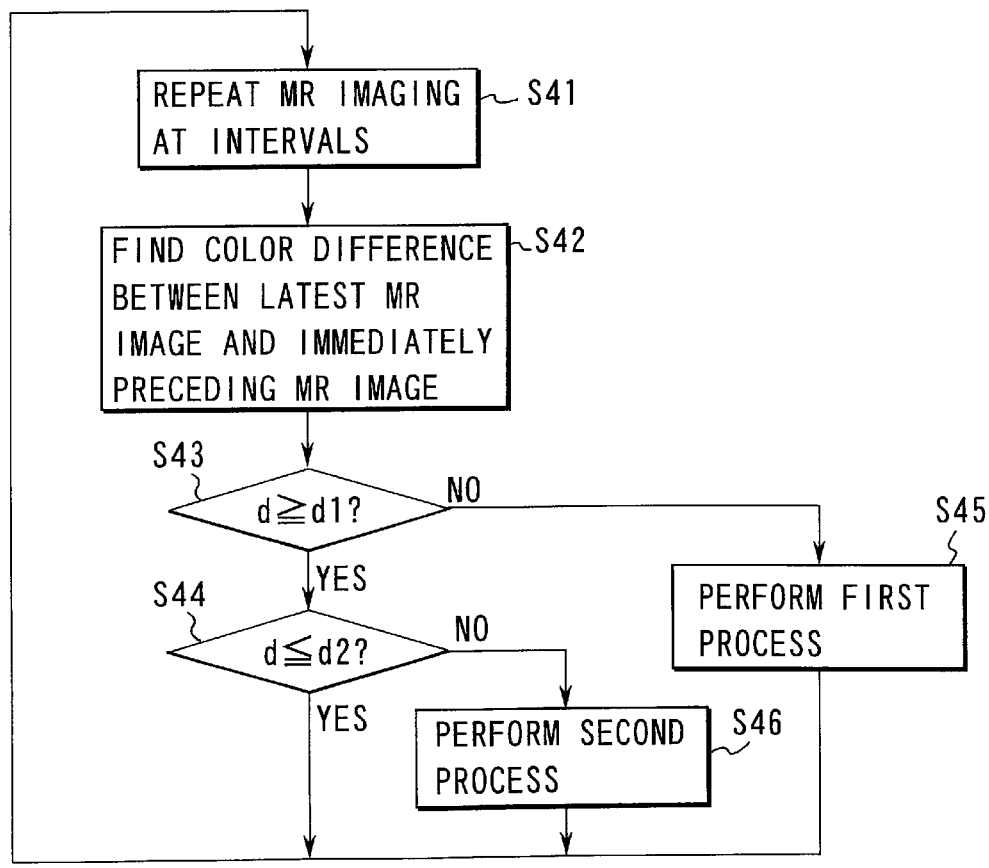
FIG. 22 is a flow chart explaining the operation of the ninth embodiment shown in FIG. 21.

FIGS. 21 and 22 show a therapeutic system according to the ninth embodiment of the invention. The ninth embodiment is identical to the first embodiment (FIGS. 1 to 8), except for the structure of the control unit 21.

As shown in FIG. 21, the control unit 21 comprises an MR-image processing section 141, a therapeutic device control section 142, and a reference output section 143.

In the ninth embodiment, the MRI apparatus 3 repeats MR imaging at intervals, while the microwave applicator 15 is applying microwaves to an affected tissue. How this is performed will be explained below, with reference to the flow chart of FIG. 22.

First, the MRI apparatus 3 repeats MR imaging at certain intervals in Step S41. In Step S42, the previous MR image and the latest MR image are compared, finding a color difference d between the MR images compared. An increase in the size of the treated region is determined from the color difference d.

Next, in Step S43, it is determined whether the color difference d obtained in Step S42 is equal to or greater than the minimum proper color difference d1. If YES, that is, if d>d1, the operation goes to Step S44. In Step S44, it is determined whether the color difference d is equal to or less than the maximum proper color difference d2. If YES, that is, if d≦d2, the operation returns to Step S41.

If the color difference d falls outside a prescribed range of proper values, the output of the microwave applicator 15 is changed as will be described below.

Namely, if NO in Step S43, that is, if d<d1 the therapy speed is too low. In this case, the operation goes to Step S45, in which one of the following processes A to D is carried out.

A. To increase the output of the applicator 15

B. To lengthen the period of outputting microwaves

C. To increase the temperature set for the living tissue

D. To alter the output waveform to increase the therapy speed

If NO in Step S44, that is, if d>d2, the therapy speed is too high. In this case, the operation goes to Step S46, in which one of the following processes A to D is carried out.

A. To decrease the output of the applicator 15

B. To shorten the period of outputting microwaves

C. To decrease the temperature set for the living tissue

D. To alter the output waveform to decrease the therapy speed

The ninth embodiment described above is advantageous in that the safety and reliability of the microwave therapy can be enhanced. This is because the microwave therapeutic apparatus 2 is controlled to effect the therapy at the best possible speed.

In the ninth embodiment, too, the MRI apparatus 3 may be replaced by an ultrasonic imaging apparatus or an X-ray CT apparatus. Further, the microwave therapeutic apparatus 2 may be replaced by a laser apparatus, an RF therapeutic apparatus, an HF therapeutic apparatus, or an ultrasonic-wave apparatus.

Figure 23:
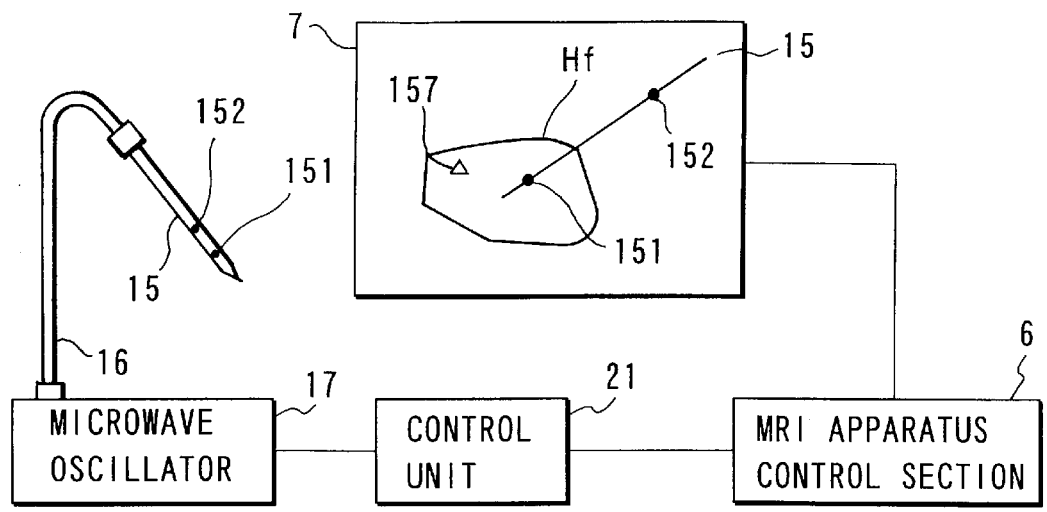
FIG. 23 is a block diagram schematically showing a therapeutic system, which is the tenth embodiment of the invention.
Figure 24:
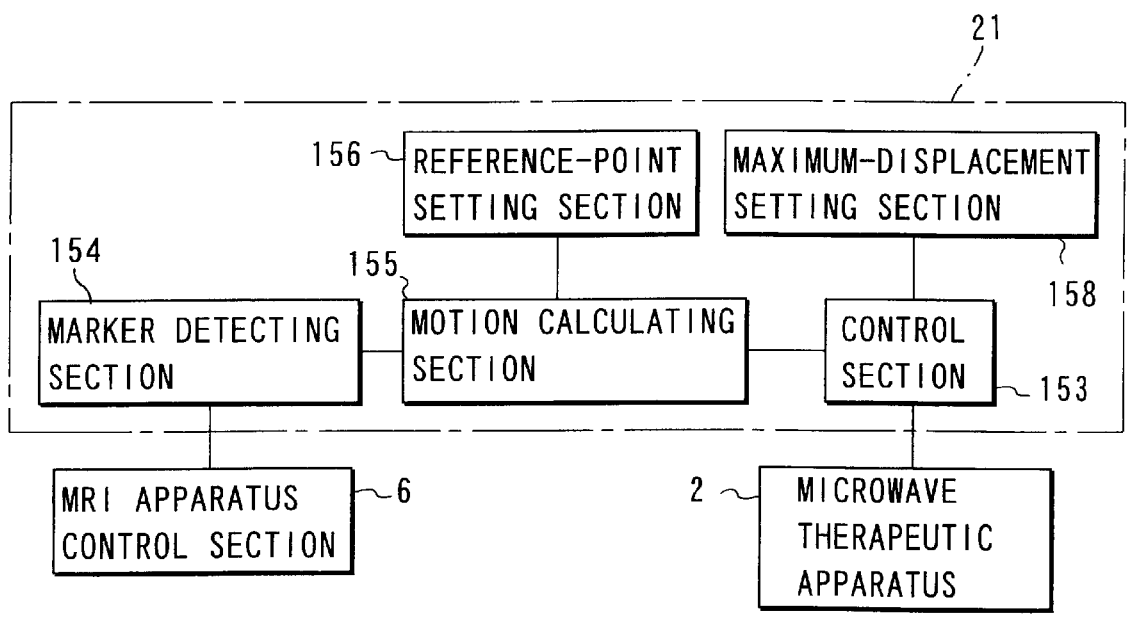
FIG. 24 is a block diagram depicting the connection of the control unit to some other components of the tenth embodiment.

FIGS. 23 and 24 show a therapeutic system according to the tenth embodiment of the invention. The tenth embodiment is identical to the therapeutic system 1 (FIGS. 1 to 8) that is the first embodiment, except for the following respects.

As shown in FIG. 23, the microwave applicator 15 has two MR markers 151 and 152. As shown in FIG. 24, the control unit 21 incorporates a control section 153, a marker detecting section 154, and a motion calculating section 155. The control section 153 is connected to the microwave therapeutic apparatus 2. The marker detecting section 154 is connected to the MRI apparatus control section 6 provided in the MRI apparatus 3. The motion calculating section 155 is connected to and located between the control section 153 and the marker detecting section 154.

A reference-point setting section 156 is connected to the motion calculating section 155. The section 156 is designed to set a reference point 157 at, a given position on the MR screen of the first monitor 7. The first monitor 7 is provided to display an MR image generated by the MRI apparatus 3. More specifically, the first monitor 7 displays the image of the organ Hf being treated and the image of the microwave applicator 15, as is illustrated in FIG. 23. A maximum-displacement setting section 158 is connected to the control section 153.

The control section 153 provided in the control unit 21 monitors the positional relation of the two MR markers 151 and 512 and the reference point 157 in order to detects the displacement of the microwave applicator 15. Upon detecting an excessive displacement of the applicator 15 from the reference point 157, the control section 153 causes the microwave oscillator 17 to stop generating microwaves.

The operation of the therapeutic system 1 according to the tenth embodiment will be explained.

At first, the doctor operates the maximum-displacement setting section 158, thus setting the maximum displacement the applicator 15 may have with respect to the reference point 157 without causing troubles. Then, the doctor pierces the organ Hf with the microwave applicator 15. The MRI apparatus 3 generates MR images of the organ Hf and applicator 15, which are displayed on the MR screen of the first monitor 7. The doctor operates the reference-point setting section 156, thereby setting a reference point 157 on the MR screen of the first monitor 7. The data representing the positional relation the MR markers 151 and 152 on the applicator 15 and the reference point 157 have at this time is stored, as an initial position value, into the memory (not shown) incorporated in the control section 153.

Every time the MRI apparatus 3 generates an MR image of the organ Hf and applicator 15, the positional relation of the MR markers 151 and 152 and the reference point 157 is detected. If the displacement of the microwave applicator 15 exceeds the maximum value set by operating the maximum-displacement setting section 158, it is determined that the applicator 15 has been displaced excessively. In this case, the control section 153 causes the microwave oscillator 17 to stop generating microwaves.

Moreover, if neither the MR marker 151 nor the MR marker 512 is displayed on the MR screen of the first monitor 7, the section 153 causes the microwave oscillator 17 to stop generating microwaves.

In the tenth embodiment, the microwave oscillator 17 automatically stops generating microwaves when the microwave applicator 15 is displaced excessively. That is, since the output of the microwave therapeutic apparatus 2 is controlled in accordance with the positional relation of the images MR markers and reference point, all generated by the MRI apparatus 3, the safety and reliability of the microwave therapy can be enhanced.

Also in the tenth embodiment, the MRI apparatus 3 may be replaced by an ultrasonic imaging apparatus or an X-ray CT apparatus. Further, the microwave therapeutic apparatus 2 may be replaced by a laser apparatus, an RF therapeutic apparatus, an HF therapeutic apparatus, or an ultrasonic-wave apparatus.

Figure 25:
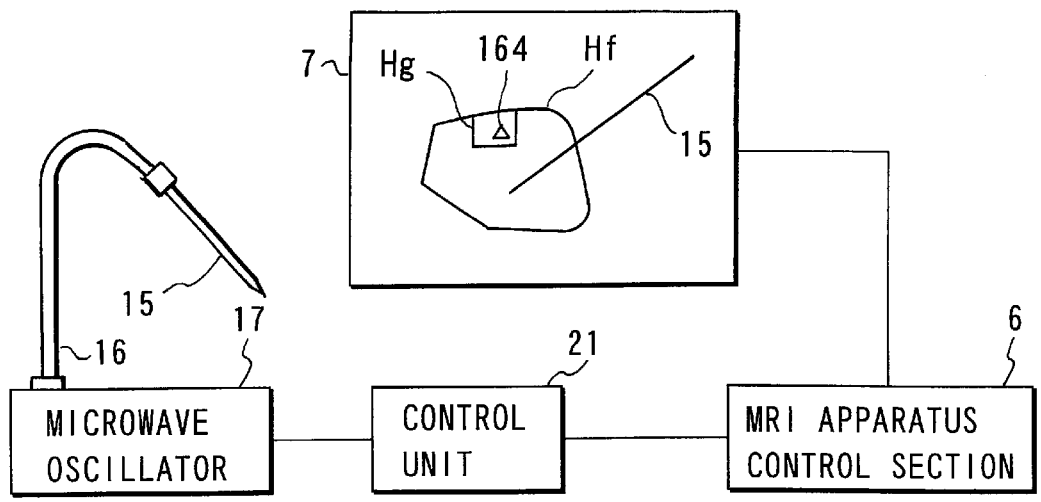
FIG. 25 is a schematic representation of a therapeutic system according to the eleventh embodiment of the present invention.
Figure 26:
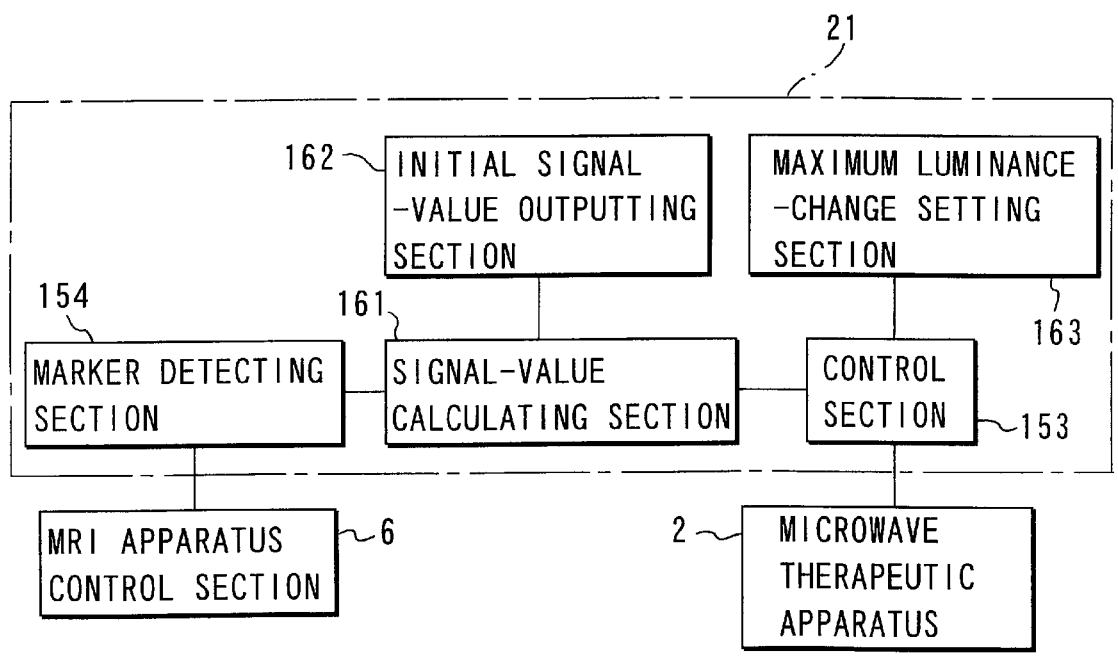
FIG. 26 is a block diagram illustrating the connection of the control unit to some other components of the eleventh embodiment.

FIGS. 25 and 26 show a therapeutic system according to the eleventh embodiment of the present invention. The eleventh embodiment is identical to the tenth embodiment (FIGS. 23 and 24), except for the structure of the control unit 21.

As depicted in FIG. 26, a signal-value change calculating section 161 is used in place of the motion calculating section 155. The section 161 is connected to and arranged between the control section 153 and the marker detecting section 154.

Further, an initial signal-value outputting section 162 is connected to the signal-value change calculating section 161. A maximum luminance-change setting section 163 is connected to the control section 153. As in the tenth embodiment, the first monitor 7 displays the image of the organ Hf being treated and the image of the microwave applicator 15, as is illustrated in FIG. 25. In FIG. 25, Hg denotes a protected region of the organ Hf.

A monitor marker 164 can be displayed on the MR screen of the first monitor 7, for example in the protected region Hg of the organ Hf that should be protected from any damage. The monitor marker 164 can be moved to any desired position on the MR screen, by operating an appropriate input device such as a keyboard or a mouse.

The operation of the eleventh embodiment will be described. First, the doctor pierces the organ Hf with the microwave applicator 15. Then, the MRI apparatus 3 generates MR images of the organ Hf and applicator 15, which are displayed on the MR screen of the first monitor 7. The doctor moves the applicator 15, setting the monitor marker 164 in the protected region Hg of the organ Hf displayed on the MR screen of the first monitor 7. Data representing the luminance of the image of the protected region Hg designated by the monitor marker 164 is stored, as initial value, into the memory (not shown) incorporated in the control section 153.

Further, the doctor operates the maximum luminance-change setting section 163, setting a maximum luminance change. Every time the MRI apparatus 3 generates an MR image of the organ Hf and applicator 15 after the microwave therapy has been started, the luminance of the image of the protected region Hg is compared with the initial value stored in the memory of the control section 153, thereby determining a change in luminance. If the luminance change exceeds the maximum luminance change set by operating the maximum luminance-change setting section 163, it is determined that degeneration has occurred in the protected region Hg of the organ Hf. In this case, the control section 153 causes the microwave oscillator 17 to stop generating microwaves.

As indicated above, the monitor marker 164 is set in any region of the MR image of the organ Hf that should be protected from damage. When the luminance change in the region of the MR image exceeds the preset maximum luminance change, it is determined that degeneration has occurred in this region. Then, the control section 153 causes the microwave oscillator 17 to stop generating microwaves. Hence, the eleventh embodiment helps to enhance the safety and reliability of the microwave therapy.

In the eleventh embodiment, too, the MRI apparatus 3 may be replaced by an ultrasonic imaging apparatus or an X-ray CT apparatus. Further, the microwave therapeutic apparatus 2 may be replaced by a laser apparatus, an RF therapeutic apparatus, an HF therapeutic apparatus, or an ultrasonic-wave apparatus.

Figure 27:
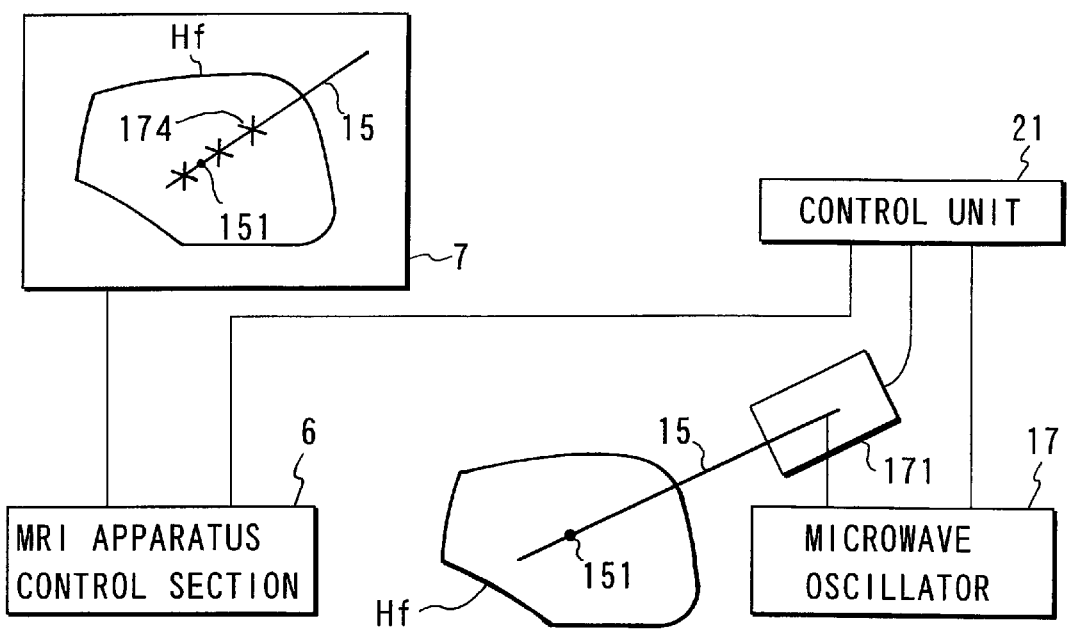
FIG. 27 is a schematic representation of a therapeutic system according to the twelfth embodiment of the this invention.
Figure 28:
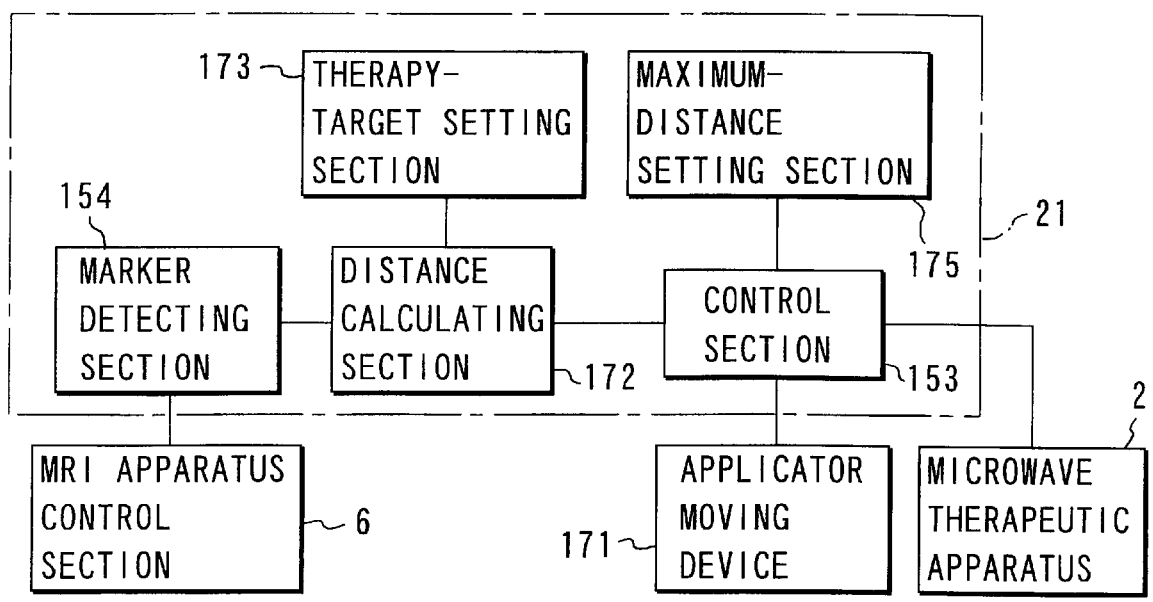
FIG. 28 is a block diagram illustrating the connection of the control unit to some other components of the twelfth embodiment.
Figure 29:
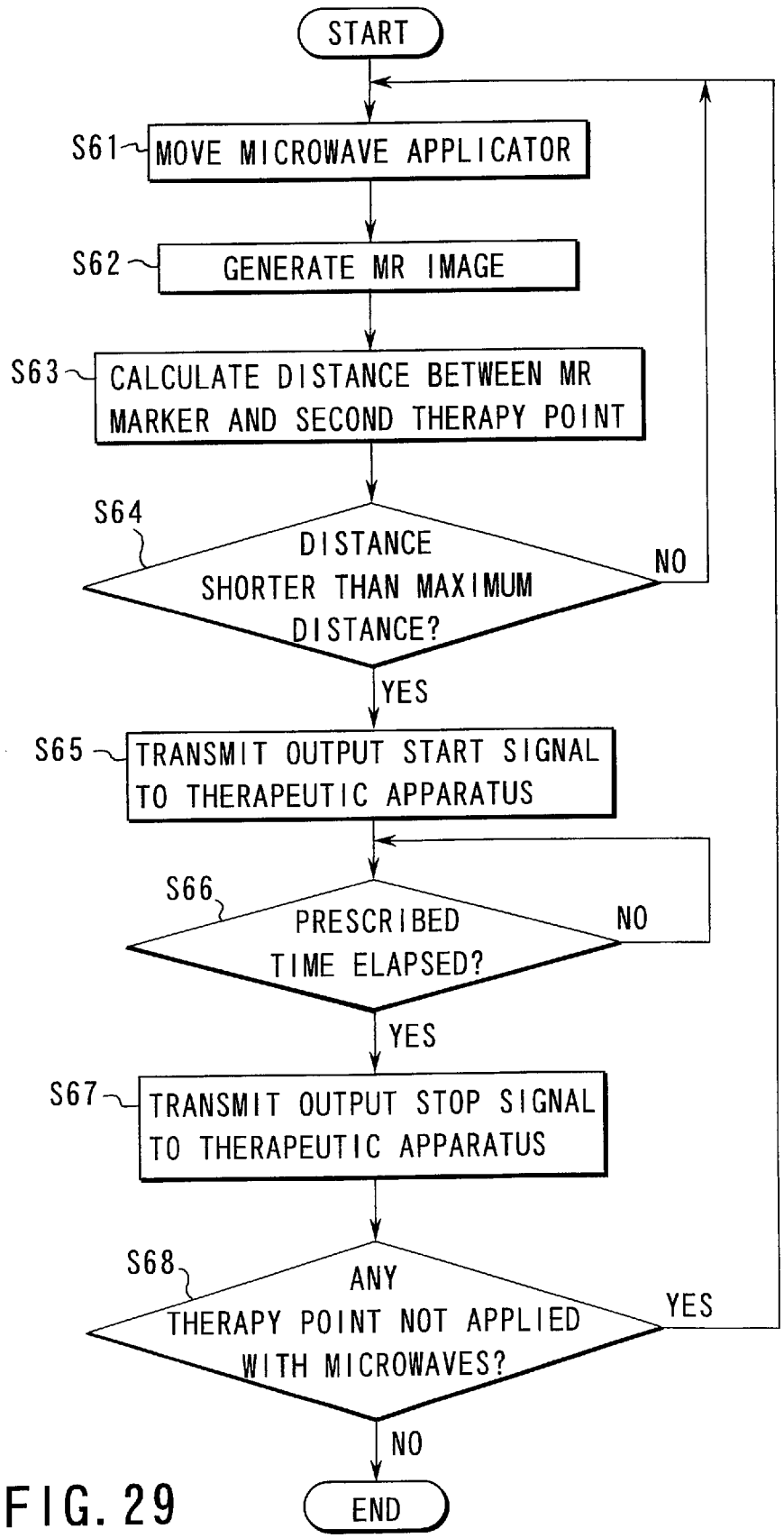
FIG. 29 is a flow chart explaining the operation of the twelfth embodiment shown in FIG. 27.

FIGS. 27 to 29 show a therapeutic system according to the twelfth embodiment of this invention. The twelfth embodiment is identical to the therapeutic system 1 (FIGS. 23 and 24), i.e., the tenth embodiment, except for the following respects.

As shown in FIG. 28, the twelfth embodiment has an applicator moving device 171, a distance calculating section 172, a therapy-point (target) setting section 173, and a maximum-distance setting section 175. The applicator moving device 171 is provided outside the control unit 21 and connected to the control section 153 of the control unit 21, for moving the microwave applicator 15 in the axial direction thereof. The distance calculating section 172, therapy-point setting section 173 and maximum-distance setting section 175 are provided in the control unit 21.

The distance calculating section 172 is connected to and located between the control section 153 and the marker detecting section 154. The therapy-point setting section 173 is connected to the distance calculating section 172, for setting a plurality of therapy points 174 on the MR screen of the first monitor 7 that displays an MR image generated by the MRI apparatus 3. The therapy points 174 indicate those parts of the organ Hf that must be treated with microwaves. The applicator moving device 171 moves the microwave applicator 15 under the control of the control section 153, until the MR marker 151 on the applicator 15 to a therapy point 174. The applicator then applies microwaves to the parts of the organ Hf, i.e. the therapy points 174. The doctor operates the maximum-distance setting section 175, setting the longest distance the MR marker 151 can be moved from one therapy point 174 to another, without causing any trouble during the microwave therapy.

The operation of the twelfth embodiment will be explained. First, the doctor pierces the organ Hf with the microwave applicator 15. The MRI apparatus 3 generates MR images of the organ Hf and applicator 15, which are displayed on the MR screen of the first monitor 7. The doctor operates the therapy-point setting section 173, setting therapy points 174 on the MR screen of the first monitor 7.

Thereafter, the control section 153 controls the applicator moving device 171, which moves the applicator 15 until the monitor marker 151 reaches the first therapy point 174. The applicator 15 is operated, applying microwaves to that part of the organ Hf which is located at the first therapy point 174. When the part of the organ Hf is treated thoroughly, the applicator 15 stops applying microwaves under the control of the control section 153. The control section 153 controls the applicator moving device 171, which moves the microwave applicator 15 in the axial direction thereof, so that the MR marker 151 may moves to the second therapy point 174.

How the microwave applicator 15 is moved, to move the MR marker 151 from the first therapy point 174 to the second therapy point 171, will be described with reference to the flow chart of FIG. 29.

At first, in Step S61, the applicator moving device 171 moves the microwave applicator 15 toward the second therapy point 174. In Step S62, the MRI apparatus 3 performs MR imaging, whereby an MR image is displayed on the MR screen of the first monitor 7.

Thereafter, in Step S63, the distance calculating section 172 calculates the distance between the MR marker 151 and the second therapy point 174. In Step S64, it is determined whether the distance calculated in Step S63 is longer than the maximum distance set by operating the maximum-distance setting section 175. If NO, the operation returns to Step S61, and Steps 62 and 63 are repeated.

If YES in Step S64, that is, if the distance calculated in Step S63 is equal to or shorter than the maximum distance, it is determined that the MR marker 151 has moved to the second therapy point 174. In this case, the operation goes to Step S65. In Step S65, the control unit 21 transmits an output start signal to the microwave therapeutic apparatus 2. In response to the output start signal, the applicator 15 starts applying microwaves to that part of the organ Hf which is located at the second therapy point 174.

In Step S66, it is determined whether a prescribed period of time has elapsed or not from the start of application of microwaves. If NO, the operation returns to Step S66. If YES, the operation goes to Step S67, in which the control unit 21 transmits an output stop signal to the microwave therapeutic apparatus 2. In response to the output stop signal, the applicator 15 stops applying microwaves.

Then, in Step S68 it is determined whether there is any therapy point 174 to which microwaves have not been applied. If YES, the operation returns to Step S61. Steps S61 to S68 are repeated until it is determined in Step S 68 that microwaves have been applied to all therapy points 174 set by operating the therapy-point setting section 173. Then, the microwave applicator 15 is no longer moved in the organ Hf, because the microwave therapy has been performed at every therapy point 174 he or she had set by operating the therapy-point setting section 173.

As mentioned above, the twelfth embodiment has the applicator moving device 171 for moving the applicator 15 in the axial direction thereof, and the therapy-point (target) setting section 173 for setting therapy points 174 on the MR screen of the first monitor 7. The control section 153 controls the device 171 such that the MR marker 151 on the applicator 15 moves from one therapy point 174 to the next one. Hence, the microwave therapeutic apparatus 2 can automatically effect microwave therapy sequentially at all therapy points 174. Therefore, it is easy to operate the microwave therapeutic apparatus 2 and the MRI apparatus 3 at the same time in the therapeutic system according to the twelfth embodiment.

Also in the twelfth embodiment, the MRI apparatus 3 may be replaced by an ultrasonic imaging apparatus or an X-ray CT apparatus. Further, the microwave therapeutic apparatus 2 may be replaced by a laser apparatus, an RF therapeutic apparatus, an HF therapeutic apparatus, or an ultrasonic-wave apparatus.

Figure 30:
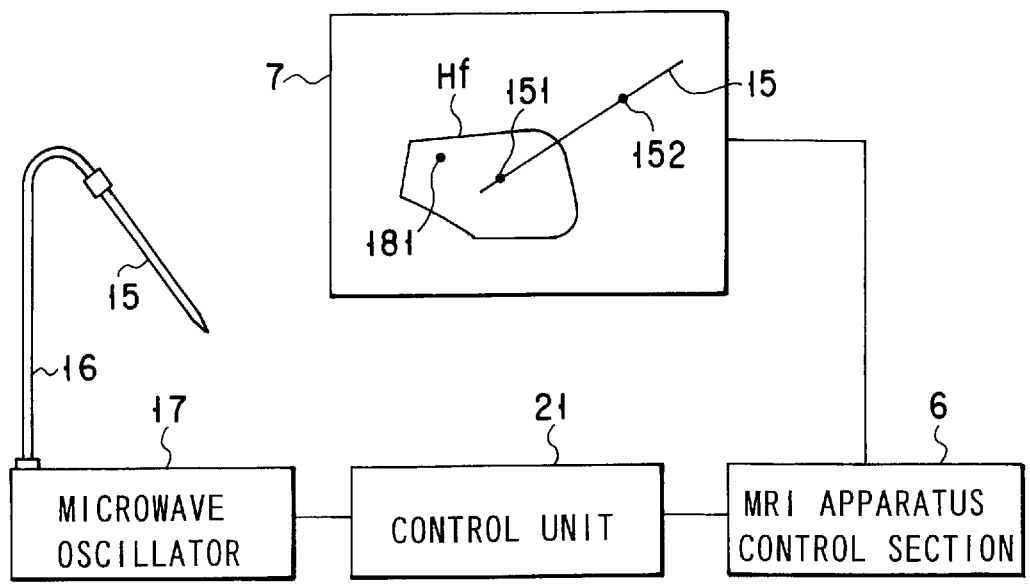
FIG. 30 is a block diagram schematically showing a therapeutic system according to the thirteenth embodiment of the invention.

FIG. 30 shows a therapeutic system according to the thirteenth embodiment of the invention. The thirteenth embodiment is identical to the therapeutic system 1 (FIGS. 23 and 24), i.e., the tenth embodiment, except for the following respects.

As illustrated in FIG. 30, a reference-point marker 181 is set on the MR screen of the first monitor 7 that displays an MR image generated by the MRI apparatus 3. The positional relation between the reference-point marker 181, on the one hand, and the MR markers 151 and 152 on the microwave applicator 15, on the other hand, is detected every time the MRI apparatus generates an MR image. If the distance between each MR marker and the reference-point marker 181 is longer than a preset value, it is determined that the microwave applicator 15 has been excessively moved in the organ Hf being treated with microwaves. In so, the control unit 21 causes the microwave oscillator 17 to stop generating microwaves.

Neither the MR marker 151 nor the MR marker 152 may be displayed on the MR screen of the first monitor 7. In this case, the control unit 21 causes the microwave oscillator 17 to stop generating microwaves.

In the thirteenth embodiment, the microwave oscillator 17 automatically stops generating microwaves when the applicator 15 is moved too much with respect to the reference-point marker 181. Hence, the safety and reliability of the microwave therapy can be enhanced, even if the patient H lying on the MR gantry 5 during the MR inspection.

Figure 31:
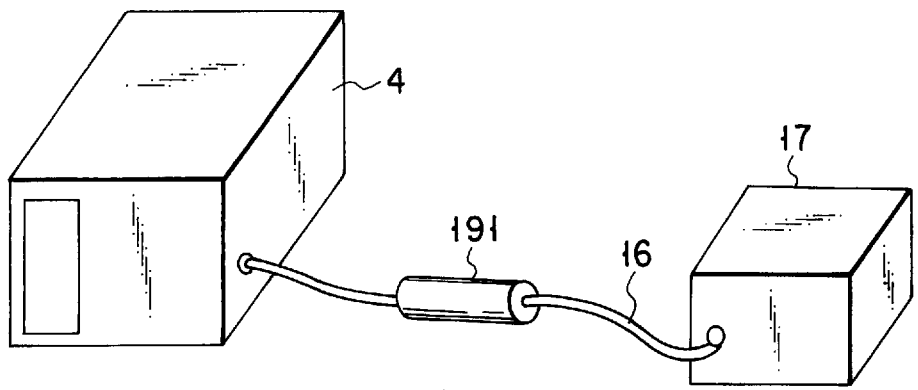
FIG. 31 is a perspective view of a therapeutic system, which is the fourteenth embodiment of the present invention.
Figure 32:
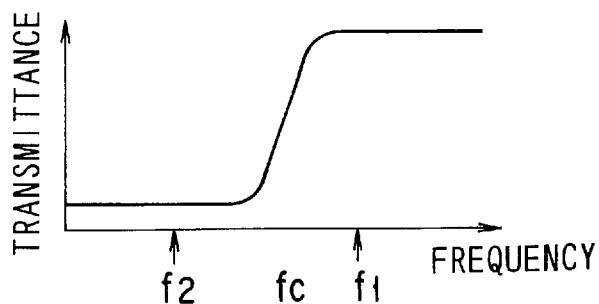
FIG. 32 is a graph representing the operating characteristic of the coaxial filter used in the fourteenth embodiment.
Figure 33:
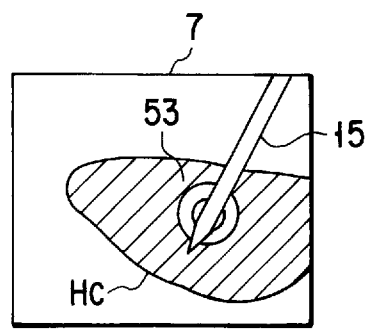
FIG. 33 is a diagram showing an MR tomogram generated in the fourteenth embodiment.

FIGS. 31 to 33 show a therapeutic system, which is the fourteenth embodiment of the present invention. This embodiment is identical to the therapeutic system 1 (FIGS. 1 to 8), i.e., the first embodiment, except for the following respects.

The microwave oscillator 17, which is provided outside the MR inspection room 4 as shown in FIG. 31, incorporates a magnetron. The magnetron is used as a microwave generator, for generating high-frequency microwaves for therapeutic purpose. The magnetron is connected to the microwave applicator 15 provided in the MR inspection room 4, by a microwave relay cable 16 that is a coaxial cable. A coaxial filter 191 is provided on the microwave relay cable 16. Hence, the coaxial filter 191 is arranged between the output section of the magnetron and the input section of the MR inspection room 4.

The coaxial filter 191 operates as a high-pass filter (HPF) having a threshold frequency fc. The threshold frequency fc is lower than the frequency f1 of the therapeutic microwaves and higher than the intermediate frequency f2 of the MRI waves, as is seen from FIG. 32. That is, f1>fc>f2. Thus, the coaxial filter 191 transmits the therapeutic microwaves and attenuates the waves.

The MRI apparatus 3 is provided in the MR inspection room 4, though not shown in FIG. 31. The MRI apparatus 3 generates an MR tomogram of the illustrated in FIG. 33. The MR tomogram includes an image of the patient's liver Hc and a region 53 thereof, coagulated as the microwave applicator 15 (not shown) applies microwaves in the lever Hc.

As described above, the coaxial filter 191 is provided on the microwave relay cable 16 that connects the microwave applicator 15 and the magnetron which are provided in the MR inspection room 4 and the microwave oscillator 17, respectively. The filter 191 can therefore remove noise, if any, in the therapeutic microwaves before these microwaves are transmitted into the MR inspection room 4, while not attenuating the therapeutic microwaves at all. The MRI tomogram is free from the influence of the noise in the therapeutic microwaves. This makes it possible to carry out microwave therapy and MR imaging at the same time. Hence, there will arise no problem if a magnetron, which is an inexpensive component but generates noise over a broad band, is used to generate therapeutic microwaves. In addition, the coaxial filter 191 can be a simple filter such as a waveguide or the like.

A therapeutic system according to the fifteenth embodiment of the present invention will be described with reference to FIG. 34A. The fifteenth embodiment differs from the fourteenth embodiment (FIGS. 31 to 33), only in the operating characteristic of the coaxial filter 191. The coaxial filter 191 operates as a band-pass filter (BPF), not as a high-pass filter as in the fourteenth embodiment. As can be understood from FIG. 34A, the coaxial filter 191 transmits therapeutic microwaves having frequency f1 and attenuates the MRI microwaves. The cut-off frequency fc of the filter 191 has an upper-limit value fcH and a lower-limit value fcL. These values fcH and fcL, the frequency f1 of the therapeutic microwaves, and the intermediate frequency f2 of the MRI waves have the relationship of: f1>fcH>fcL>f2.

In the fifteen embodiment, the coaxial filter 191 is a band-pass filter. Therefore, the microwave therapy and the MR imaging can be effected at the same time by the use of a single filter, regardless of the intermediate frequency f2 of the MRI waves. Operating as a band-pass filter, the coaxial filter 191 transmits the therapeutic microwaves and attenuates the MRI waves as shown in FIG. 34A.

A therapeutic system according to the sixteenth embodiment of the present invention will be described with reference to FIG. 34B. The sixteenth embodiment differs from the fourteenth embodiment (FIGS. 31 to 33), only in the operating characteristic of the coaxial filter 191. The coaxial filter 191 operates as a band-cut filter (BCF), not as a high-pass filter as in the fourteenth embodiment, and attenuates only the MRI microwaves having frequency f2. The coaxial filter 191 has a cut-off frequency having an upper-limit value fcH and a lower-limit value fcL. As can be seen from FIG. 34B, the values fcH and fcL, the frequency f1 of the therapeutic microwaves, and the frequency f2 of the MRI waves have the relationship of: f1>fcH>f2>fcL.

Since the coaxial filter 191 is a band-cut filter (BCF), it attenuates only microwaves of a specific band. Hence, the filter 191 generates heat only a little while operating and can be made small. The microwave therapy and the MR imaging can be performed at the same time by the use of a single filter, regardless of the frequency f1 of the therapeutic microwaves. The filter 191 may be replaced by a waveguide that has been adjusted in size to have the cut-off frequency described above.

Figure 35:
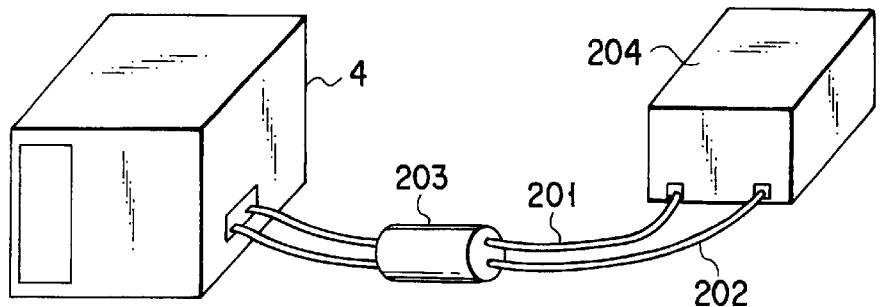
FIG. 35 is a perspective view of a therapeutic system, which is the seventeenth embodiment of the present invention.
Figure 36:
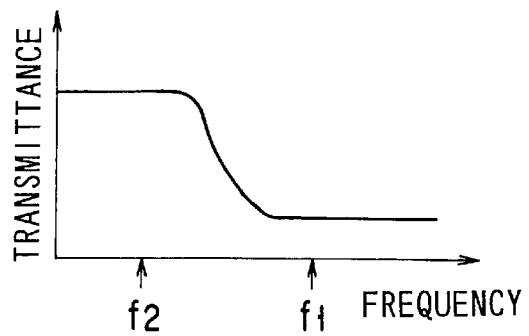
FIG. 36 is a graph representing the operation characteristic of the filter used in a therapeutic system according to the seventeenth embodiment of this invention.

FIGS. 35 and 36 show a therapeutic system according to the seventeenth embodiment of the invention. The therapeutic system 1 according to the seventeenth embodiment differs from the fourteenth embodiment (FIGS. 31 to 33) in the following respects.

As shown in FIG. 35, a high-frequency power supply 204 is provided outside the MR inspection room 4, i.e. the magnetic shield room for use in MR imaging. The power supply 204 includes a high-frequency wave generator of two-wire output type (not shown), such as an electrode knife apparatus. Two high-frequency wave relay cables 201 and 202 are connected at one end to the high-frequency wave generator arranged in the power supply 204. The first cable 201 is connected at the other end to an active electrode (not shown) provided in the MR inspection room 4. The second cable 202 is connected at the other end to a return electrode (not shown) provided in the MR inspection room 4. A two-wire filter 203 is provided on the cables 201 and 202. The filter 203 operates as a low-pass filter (LPF) having a threshold frequency fc. The threshold frequency fc is lower than the frequency f1 of the therapeutic microwaves and higher than the frequency f2 of the MRI microwaves, as is seen from FIG. 36. That is, f1>fc>f2. Thus, the coaxial filter 191 transmits the MRI microwaves and attenuates the therapeutic microwaves.

As described above, the cables 201 and 202 connects the two-wire high-frequency wave generator provided in the power supply 204 to the active electrode and return electrode, both provided in the MR inspection room 4. Since the two-wire filter 203 is provided on the cables 201 and 202, can remove noise, if any, in the MRI waves before the MRI microwaves are transmitted from the power supply 204 to the MR inspection room 4, while attenuating the therapeutic microwaves. The MRI tomogram is therefore free from the influence of the noise in the MRI waves. This makes it possible to carry out microwave therapy and MR imaging at the same time.

Figures 37A, 37B:
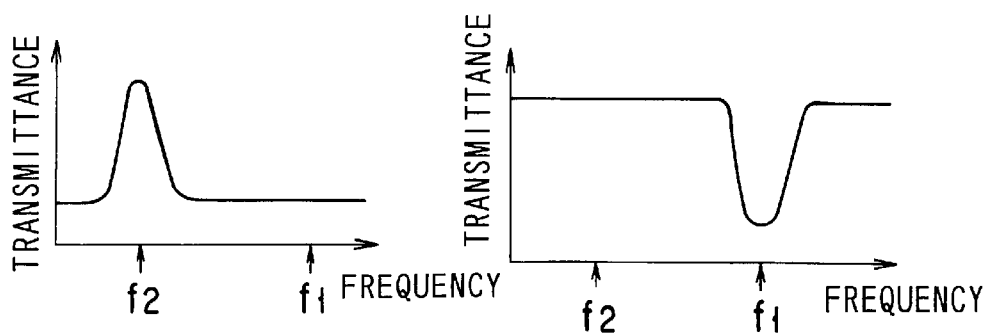
FIG. 37A is a graph depicting the operation characteristic of the filter used in a therapeutic system according to the eighteenth embodiment of the invention.
FIG. 37B is a graph representing the operation characteristic of the filter used in a therapeutic system according to the nineteenth embodiment of the present invention.

A therapeutic system according to the eighteenth embodiment of the invention will be described with reference to FIG. 37A. The eighteenth embodiment differs from the seventeenth embodiment (FIGS. 35 and 36), only in the operating characteristic of the two-wire filter 203. In the eighteenth embodiment, the two-wire filter 203 provided on the cables 201 and 202 operates as a band-pass filter (BPF), not as a low-pass filter as in the seventeenth embodiment. As can be understood from FIG. 37A, the filter 203 transmits the MRI microwaves having frequency f2 and attenuates the therapeutic microwaves having frequencies similar to frequency f1.

Thanks to the use of a single filter, i.e., the two-wire filter 203 functioning as a band-pass filter, the microwave therapy and the MR imaging can be performed at the same time, regardless of the frequency f2 of the MRI waves.

A therapeutic system according to the nineteenth embodiment of this invention will be described with reference to FIG. 37B. The nineteenth embodiment differs from the seventeenth embodiment (FIGS. 35 and 36), only in the operating characteristic of the two-wire filter 203. In the nineteenth embodiment, the two-wire filter 203 provided on the cables 201 and 202 operates as a band-cut filter (BCF), not as a low-pass filter as in the seventeenth embodiment. As can be understood from FIG. 37B, the filter 203 attenuates only the therapeutic microwaves having frequency f1.

Thanks to the use of a single filter, i.e., the two-wire filter 203 functioning as a band-cut filter, the microwave therapy and the MR imaging can be performed at the same time, regardless of the frequency f1 of the therapeutic microwaves. The two-wire filter 203 can remove noise, if any, in therapeutic microwaves which have harmonic components such as pulse-shaped components.

Figure 38:
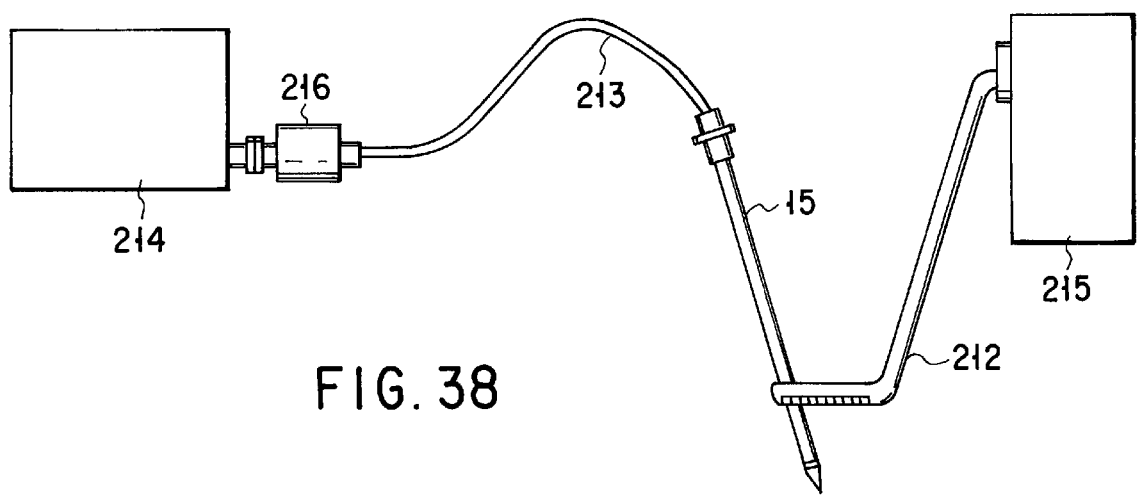
FIG. 38 is a schematic representation of a therapeutic system according to the twentieth embodiment of the present invention.

FIG. 38 shows a therapeutic system according to the twentieth embodiment of the present invention. This system comprises a microwave applicator 15, a diagnostic ultrasonic probe 212, a coaxial cable 213, a microwave generator 214, and an ultrasonic imaging apparatus 215. The microwave applicator 15 is used as a therapeutic applicator for applying therapeutic energy to an affected tissue. The diagnostic ultrasonic probe 212 is connected to the microwave applicator 15 and serves as observation means for detecting the position of the microwave applicator 15. The coaxial cable 213 connects the applicator 15 to the microwave generator 214. The diagnostic ultrasonic probe 212 is connected to the ultrasonic-wave imaging apparatus 215.

The system further comprises a coaxial filter 216, which is provided on the coaxial cable 213. The coaxial filter 216 operates as a high-pass filter. Its threshold frequency is lower than the intermediate frequency of the therapeutic microwaves and higher than the ultrasonic waves used in the ultrasonic imaging apparatus 215.

In the twentieth embodiment, the coaxial filter 216, which operates as a high-pass filter, is provided on the coaxial cable 213 which connects the microwave applicator 15 to the microwave generator 214. The filter 216 therefore removes noise which may adversely influence the ultrasonic imaging performed by the ultrasonic imaging apparatus 215, without attenuating the therapeutic microwaves supplied from the microwave generator 214 to the microwave applicator 15. Hence, the ultrasonic imaging apparatus 215 can generate a clear ultrasonic image even if the ultrasonic imaging and the microwave therapy are carried out at the same time, by means of the probe 212 and the applicator 15, respectively.

Figures 34A, 34B:
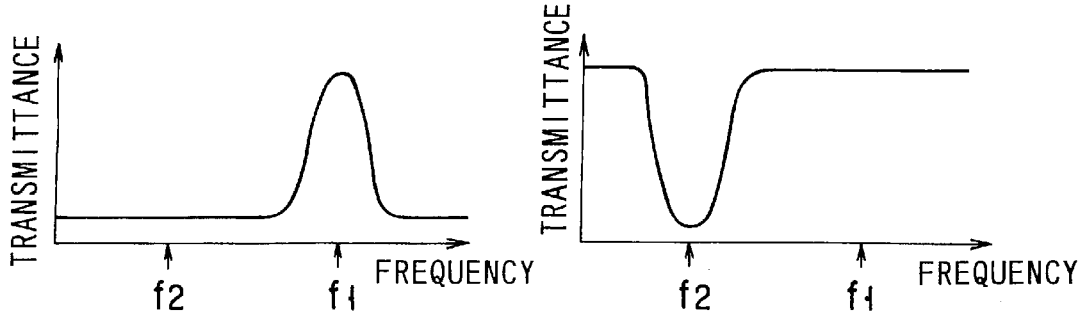
FIG. 34A is a graph illustrating the operation characteristic of the coaxial filter used in a therapeutic system according to the fifteenth embodiment of the invention.
FIG. 34B is a graph representing the operation characteristic of the coaxial filter used in a therapeutic system according to the sixteenth embodiment of this invention.

The coaxial filter 216 may be replaced by a band-pass filter that has the operating characteristic shown in FIG. 34A, or by a band-cut filter that has the operating characteristic shown in FIG. 34B.

Figure 39:
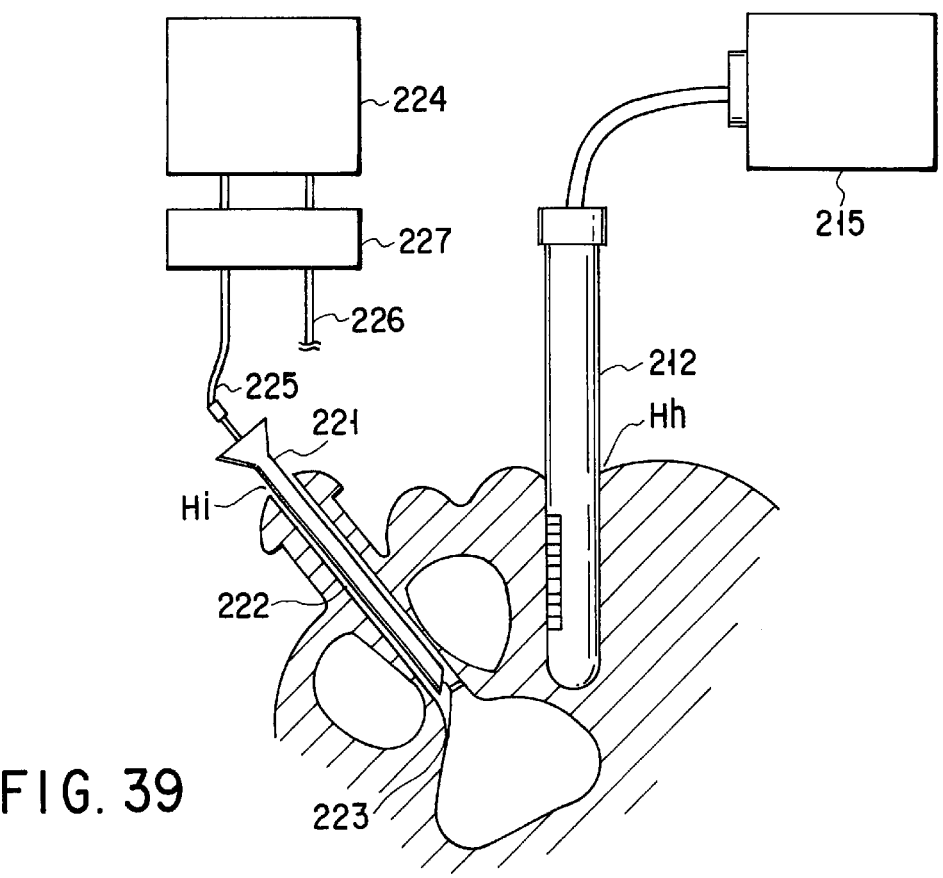
FIG. 39 is a diagram schematically showing a therapeutic system according to the twenty-first embodiment of this invention.

FIG. 39 shows a therapeutic system, which is the twenty-first embodiment of the present invention. This therapeutic system comprises a diagnostic ultrasonic probe 212, an ultrasonic imaging apparatus 215, a resectoscope 221, and a two-wire high-frequency wave generator 224. The resectoscope 221 is used as a therapeutic applicator for applying therapeutic energy to an affected tissue. The diagnostic ultrasonic probe 212 is similar to its counterpart of the twentieth embodiment (FIG. 38).

The resectoscope has a slender insertion section 222, which can be inserted into a body cavity of a patient. The insertion section 222 contains a loop electrode 223. A high-frequency output is supplied to the loop electrode 223 from the two-wire high-frequency wave generator 224.

Two cables 225 and 226 are connected at one end to the high-frequency wave generator 224. The loop electrode 223 provided in the resectoscope 221 is connected to the cable 225. The high-frequency generator 224 incorporates a return electrode (not shown), which is connected to the cable 226.

A two-wire filter 227 is provided on the cables 225 and 226, which supply the therapeutic energy to the resectoscope 221 from the two-wire high-frequency wave generator 224. The filter 227 operates as a low-pass filter having a threshold frequency that is lower than the frequency of the therapeutic high-frequency waves and higher than the frequency of the ultrasonic imaging waves.

To perform ultrasonic imaging and high-frequency wave therapy, the diagnostic ultrasonic probe 212 and the insertion section 222 of the resectoscope 221 are inserted into, for example, the rectum Hh and urethra Hi of the patient, respectively, as is illustrated in FIG. 39.

As indicated above, the two-wire filter 227 functioning as a low-pass filter is provided on the two cables 225 and 226 that supply the therapeutic energy from the generator 224 to the resectoscope 221. Hence, the filter 227 can remove noise in the therapeutic high-frequency waves, without attenuating the therapeutic waves similar to sine waves, before the loop electrode 223 approaches the diagnostic ultrasonic probe 212. As a result, the ultrasonic imaging apparatus 215 can generate a clear ultrasonic image even if the ultrasonic imaging and the high-frequency wave therapy are carried out at the same time, by means of the probe 212 and the applicator 15, respectively.

The twenty-first embodiment is not limited to a system, wherein a resectoscope is employed as therapeutic applicator. Rather, it may be applied to a system in which any other therapeutic applicator that applies high-frequency energy to accomplish therapy, while an ultrasonic imaging apparatus is operating.

Figure 40:
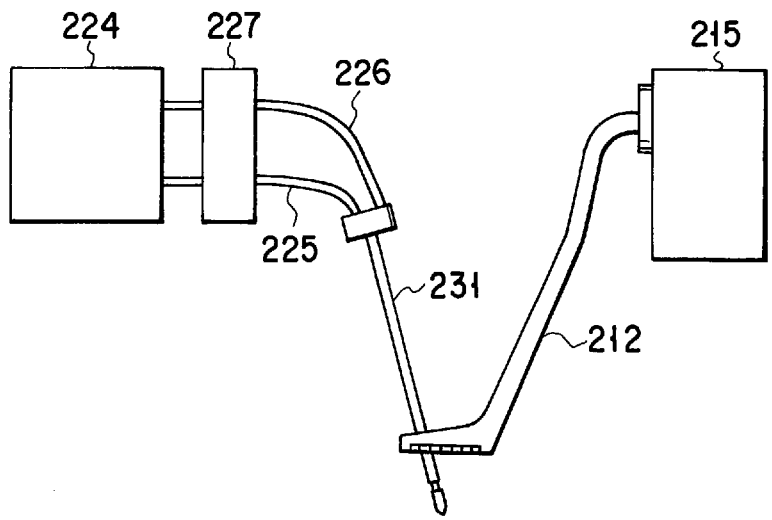
FIG. 40 is a diagram schematically showing a therapeutic system according to the twenty-second embodiment of the present invention.

FIG. 40 shows a therapeutic system according to the twenty-second embodiment of this invention. The twenty-second embodiment is different from the twenty-first embodiment (FIG. 39) in two respects only. First, a paracentetic bipolar electrode 231 is used in place of the resectoscope 221. Secondly, an ultrasonic probe 212 for use in combination with a raparoscope. The twenty-second embodiment can achieve the same advantage as the twenty-first embodiment.

A therapeutic system according to the twenty-third embodiment of the invention will be described with reference to FIG. 41. The twenty-third embodiment differs from the fourteenth embodiment (FIGS. 31 to 33) in the following respects.

A terminal board 242 is fitted in a sidewall of the MR inspection room 4, i.e. the magnetic shield room for use in MR imaging, and a coaxial noise filter 243 is mounted on the terminal board 242. The coaxial nose filter 243 is provided on a microwave relay cable 16 (i.e., a coaxial cable), which connects the microwave applicator 15 and the microwave generator (e.g., magnetron) which are provided in the MR inspection room 4 and the microwave oscillator 17, respectively. The filter 243 is either a band-pass filter or a high-pass filter, which transmits the MRI waves used in the MRI apparatus 3 to generate MR images.

As described above, the noise filter 243 is provided on the microwave relay cable 16. Therefore, the microwave therapy and the MRI imaging can be carried out at the same time, irrespective of the frequency of the microwaves generated by the microwave generator.

Figure 42:
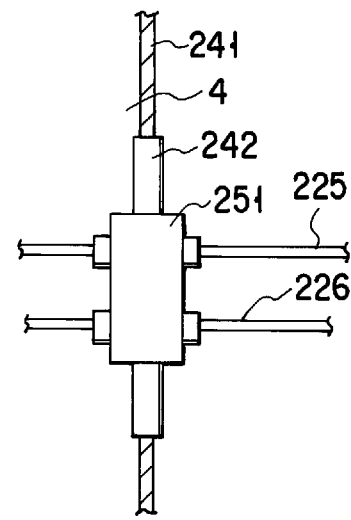
FIG. 42 is a diagram showing the filter incorporated in a therapeutic system according to the twenty-fourth embodiment of the invention.

A therapeutic system, which is the twenty-fourth embodiment of the invention, will be described with reference to FIG. 42. The therapeutic applicator used in this embodiment is a resectoscope 221 having a loop electrode 223, as in the twenty-first embodiment (FIG. 39). And a diagnostic ultrasonic probe 212 is used as observation means for detecting the position of the resectoscope 221.

Figure 41:
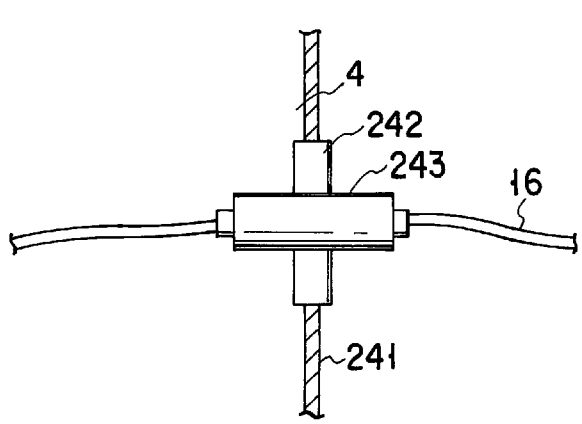
FIG. 41 is a diagram showing the coaxial filters incorporated in a therapeutic system according to the twenty-third embodiment of the present invention.

In the twenty-fourth embodiment, a terminal board 242 is fitted in a side wall of the MR inspection room 4 (i.e. the magnetic shield room for use in MR imaging), as in the twenty-third embodiment (FIG. 41). A two-wire noise filter 251 is mounted on the terminal board 242. The filter 251 is provided on two cables 225 and 226 for supplying therapeutic energy from a high-frequency generator 224, as in the twenty-first embodiment (FIG. 39). The filter 251 is either a band-pass filter or a high-pass filter, which transmits the MRI waves used in the MRI apparatus 3 to generate MR images.

As described above, the noise filter 251 is provided on the two cables 225 and 226. Therefore, the microwave therapy and the MRI imaging can be carried out at the same time, irrespective of the frequency of the output frequency of the high-frequency generator 224.

Figure 43:
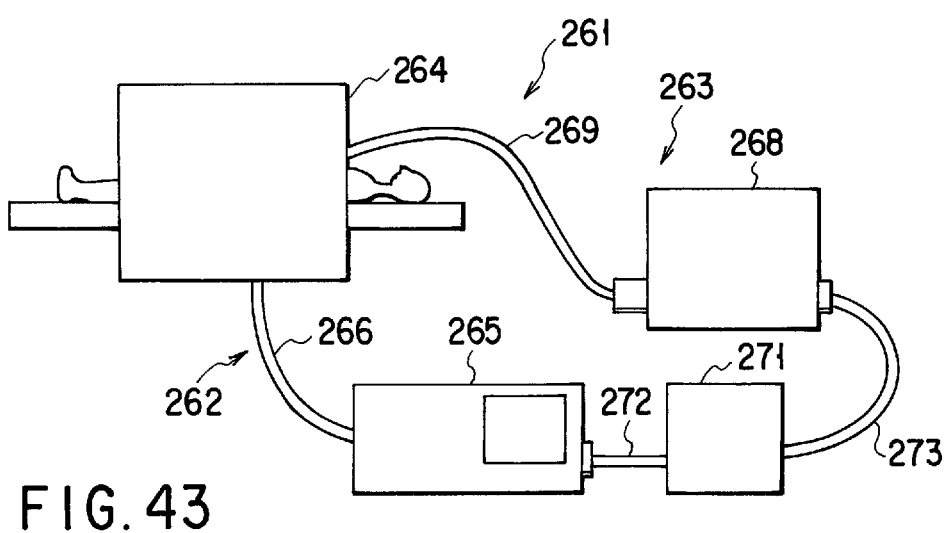
FIG. 43 is a schematic representation of a therapeutic system according to the twenty-fifth embodiment of the present invention.

FIGS. 43 to 47 show a therapeutic system 261, which is the twenty-fifth embodiment of the present invention. FIG. 43 schematically depicts this therapeutic system 261. As shown in FIG. 43, the system 261 comprises an MRI apparatus 262 and a therapeutic apparatus 263. The MRI apparatus 262 comprises an MRI gantry 264 and an MRI controller 265, which are connected by an MRI signal cable 266. The therapeutic apparatus 263 comprises a therapeutic energy generator 268 and a therapeutic probe 270 (see FIG. 44). The therapeutic probe 270 is connected to the therapeutic energy generator 268 by a cable 269.

The MRI apparatus 262 further comprises an observation unit 271, which is provided between the MRI controller 265 and the therapeutic energy generator 268. The observation unit 271 is connected to the MRI controller 265 by a signal cable 272 and to the therapeutic energy generator 268 by a signal cable 273. In the therapeutic system 261, a doctor operates the therapeutic apparatus 263, performing therapy, while observing the MRI image generated by the MRI apparatus 262.

Figure 46:
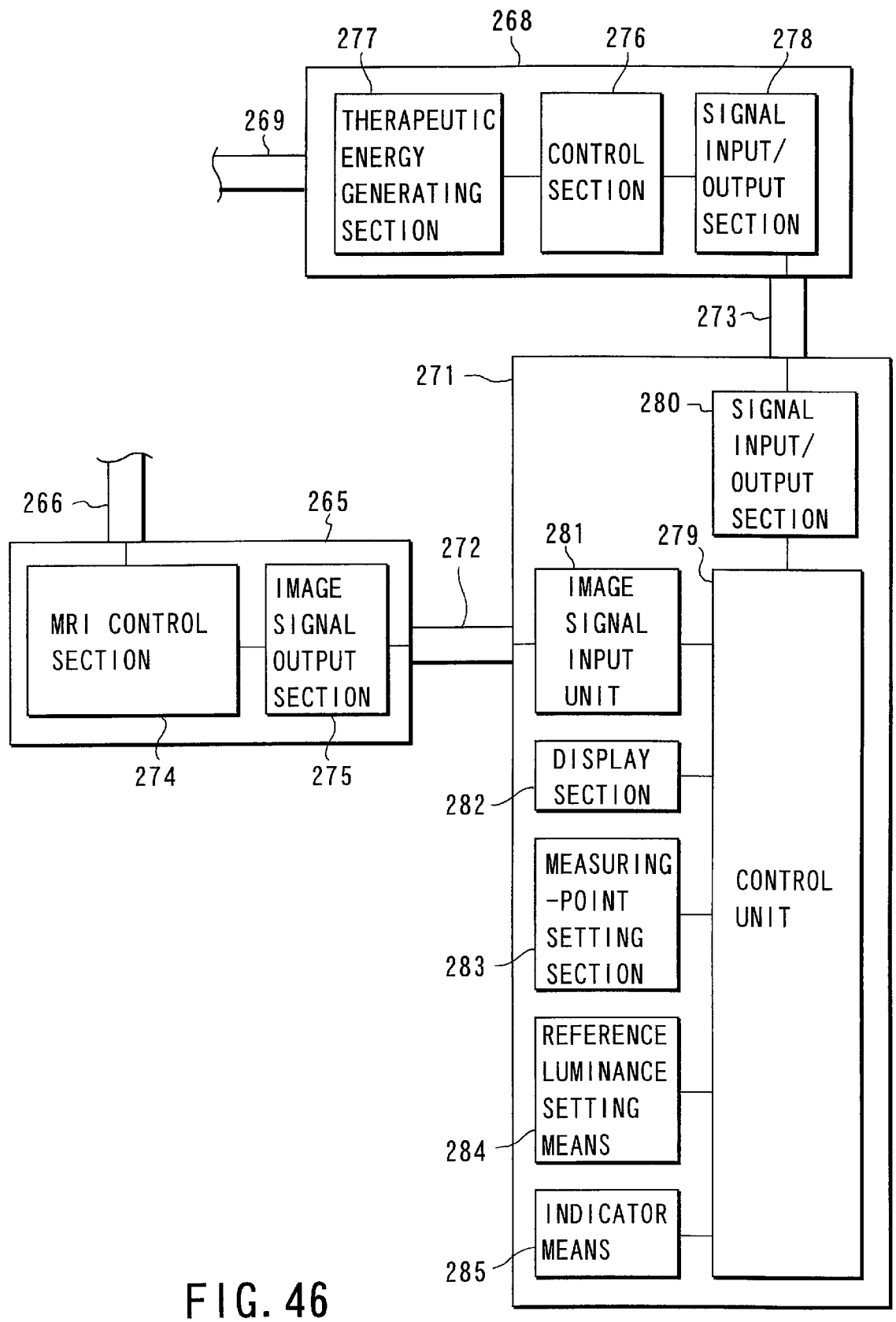
FIG. 46 is a block diagram depicting the observation unit that is incorporated in the twenty-fifth embodiment.

As shown in FIG. 46, the MRI controller 265 comprises an MRI control section 274 and an image signal output section 275. The input of the MRI control section 274 is connected to the MRI gantry 264 by the MRI signal cable 266. The output of the MRI control section 274 is connected to the image signal output section 275.

As FIG. 46 shows, the therapeutic energy generator 268 comprises a therapeutic energy control section 276, a therapeutic energy generating section 277, and a signal input/output section 278. The therapeutic energy generating section 277 is connected to the therapeutic probe 270 by the cable 269.

The observation unit 271 comprises a control section 279, a signal input/output section 280, an image signal input unit 281, a display section 282, a measuring-points setting section 283, a reference luminance setting means 284 and an indicator means 285. The signal input/output section 280, image signal input unit 281, display section 282, measuring-points setting section 283, reference luminance setting means 284 and indicator means 285 are connected to the control section 279. The image signal input unit 281 is connected to the image signal output section 275 of the MRI controller 265 by the signal cable 272. The signal input section /output section 280 is connected to the signal input/output section 278 of the therapeutic energy generator 268 by the signal cable 273. The display section 282 incorporates a monitor 267 for displaying an MR image.

Figure 44:
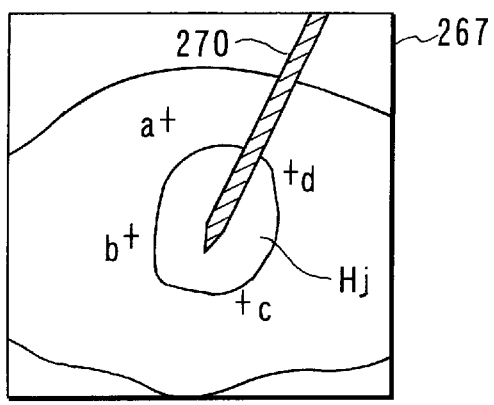
FIG. 44 shows an MR image generated in the twenty-fifth embodiment shown in FIG. 43.
Figure 45:
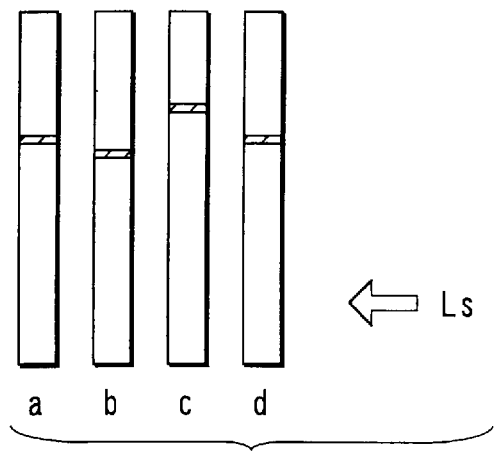
FIG. 45 is a diagram showing the luminances detected at various points in the MR image shown in FIG. 44.

The measuring-points setting section 283 is connected to an input device (not shown) such as a keyboard, a mouse, a track ball, a touch pen, or the like. As the input device is operated, the section 283 sets four measuring points (a) to (d) in the MR image generated by the MRI apparatus 262, around the image Hj of the affected region as is illustrated in FIG. 44. Luminance is measured at the measuring points (a) to (d). The display section 282 of the observation unit 271 displays the luminances at these points (a) to (d), as is shown in FIG. 45.

The input device (e.g., keyboard, mouse, track ball, touch pen, or the like) is connected to the reference luminance setting means 284, too. As the input device is operated, the means 284 sets a reference luminance value Ls for each measuring point. When the luminances at all points (a) to (d) exceed the reference luminance values, the observation unit 271 outputs a therapy stop signal to the therapeutic energy generator 268, which stops generating therapeutic energy.

The therapeutic system 261, i.e., the twenty-fifth embodiment of the invention, will be described with reference to the flow chart of FIG. 47.

In Step S71, the MRI apparatus 262 is operated, generating an MRI image before the therapeutic probe 270 is operated to perform therapy. Then, in Step S72, the MRI controller 265 transfers an image signal to the observation unit 271. In Step S73, the display section 282 of the observation unit 271 displays the MR image generated by the MRI apparatus 262.

Thereafter, in Step S74, a doctor operates the input device (e.g., keyboard, mouse, track ball, touch pen, or the like) while observing the MR image displayed on the screen of the display section 282. The measuring-points setting section 283 of the observation unit 271 sets four measuring points (a) to (d) in the MR image, around the image Hj of the affected region as is illustrated in FIG. 44. In Step S75, the doctor operates the input device again, while observing the MRI image displayed on the screen of the display section 282. Therefore, the reference luminance setting means 284 sets a reference luminance value Ls for each measuring point.

Therapy is then started in Step S76. More specifically, the therapeutic energy generator 268 supplies a therapy start signal to the observation unit 271 in Step S77. In Step 78, the MRI apparatus 262 generates an MRI image. In Step S79, the MRI controller 265 transfers an image signal to the observation unit 271.

In Step S80, the luminance at each measuring point is measured and displayed as shown in FIG. 45. In Step S81, it is determined whether all luminances at the points (a) to (d) exceed the reference luminance values Ls, respectively. If NO, the operation returns to Step 78. If YES, the therapy is terminated in Step S82. In Step S83, the indicator means 285 of the observation unit 271 is operated, indicating that the therapy has been terminated.

As the therapy proceeds, the colors of the parts of the MR image, which are at the measuring points (a) to (d), change from white to black or vice versa, for example, depending on the parameters which have been set. Hence, the colors of these parts of the MR image change to either black or white when the luminances at all measuring points (a) to (d) exceed the reference luminance values Ls, respectively.

In the twenty-fifth embodiment, the input device (e.g., keyboard, mouse, track ball, touch pen, or the like) is operated, setting four measuring points (a) to (d) in the MR image, around the image Hj of the affected region as is illustrated in FIG. 44. The input device is operated again, setting four reference luminance values Ls for the measuring points (a) to (d), respectively. When the luminances at all measuring points exceed the reference values Ls, respectively, the therapeutic energy generator 268 stops applying therapeutic energy to the affected region. Thus, the therapy is automatically terminated when the luminances at all measuring points exceed the reference values Ls. The influence of the therapy energy on the living tissues in the patient is therefore minimized. When the luminances at all measuring points exceed the reference values Ls, it is known that the therapy has been thoroughly achieved on the entire affected region, This is because the four measuring points (a) to (d) surround the image Hj of the affected region.

With the therapeutic system according to the twenty-fifth embodiment, it is possible to perform the MR imaging (i.e., providing an MRI tomogram by means of the MRI apparatus 262) and the therapy (i.e., applying therapy energy by means of the probe 270), either at the same time or alternately.

A therapeutic system according to the twenty-sixth embodiment of this invention will be described, with reference to the flow chart of FIG. 48. The twenty-sixth embodiment differs from the twenty-fifth embodiment (FIGS. 43 to 47) only in the steps of operation which are carried out after the completion of therapy.

Figure 47:
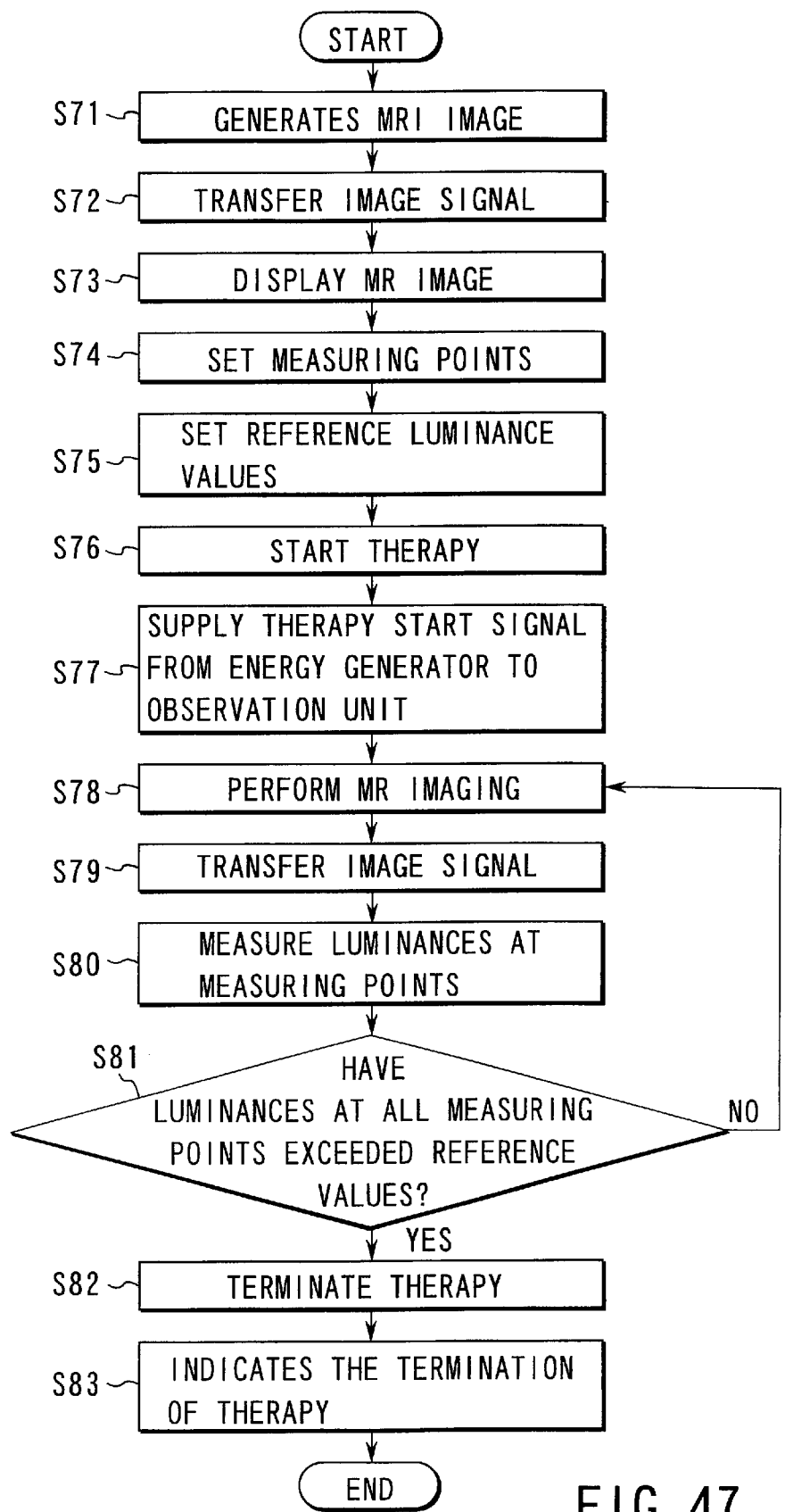
FIG. 47 is a flow chart explaining the operation of the twenty-fifth embodiment.

In the twenty-sixth embodiment, Steps S71 to S83 are carried out in the same order as in the twenty-fifth embodiment (see the flow chart of FIG. 47). After the indicator means 285 informs, in Step S83, that the therapy should be terminated, the observation unit 271 supplies a therapy end signal to the therapeutic energy generator 268 in Step S84. In Step S85, the generator 268 stops applying therapeutic energy to the affected region, whereby the therapy is terminated. More precisely, the therapeutic probe 270 stops applying the energy in response to the therapy end signal. Alternatively, the therapy energy applied from the probe 270 may be decreased in response to the therapy end signal, thereby to terminate the therapy automatically.

In the twenty-sixth embodiment, the probe 270 stops applying the therapy energy or the therapy energy applied from the probe 270 is decreased when the affected region is thoroughly treated. In other words, the therapy is automatically terminated the moment the affected region is completely treated. The influence of the therapy energy on the living tissues in the patient is therefore minimized.

Figure 49:
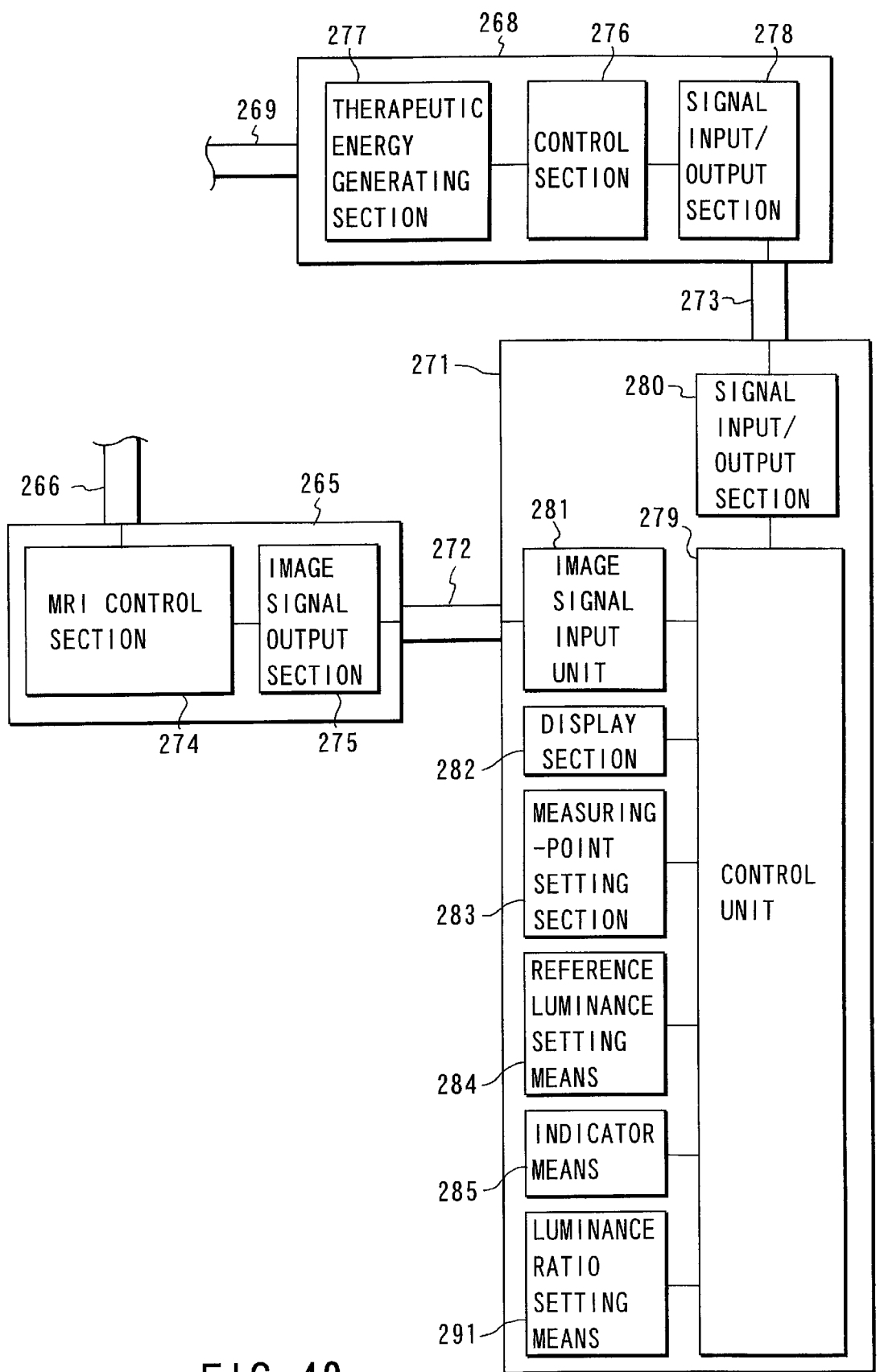
FIG. 49 is a block diagram of the observation unit incorporated in a therapeutic system according to the twenty-seventh embodiment of the present invention.

A therapeutic system according to the twenty-seventh embodiment of the invention will be described, with reference to FIGS. 49 and 50. This embodiment differs from the twenty-fifth embodiment (FIGS. 43 to 47) in that a luminance ratio setting means 291 is provided in the observation unit 271. The therapeutic system 261 is operated, as will be explained with reference to the flow chart of FIG. 50.

Figure 50:
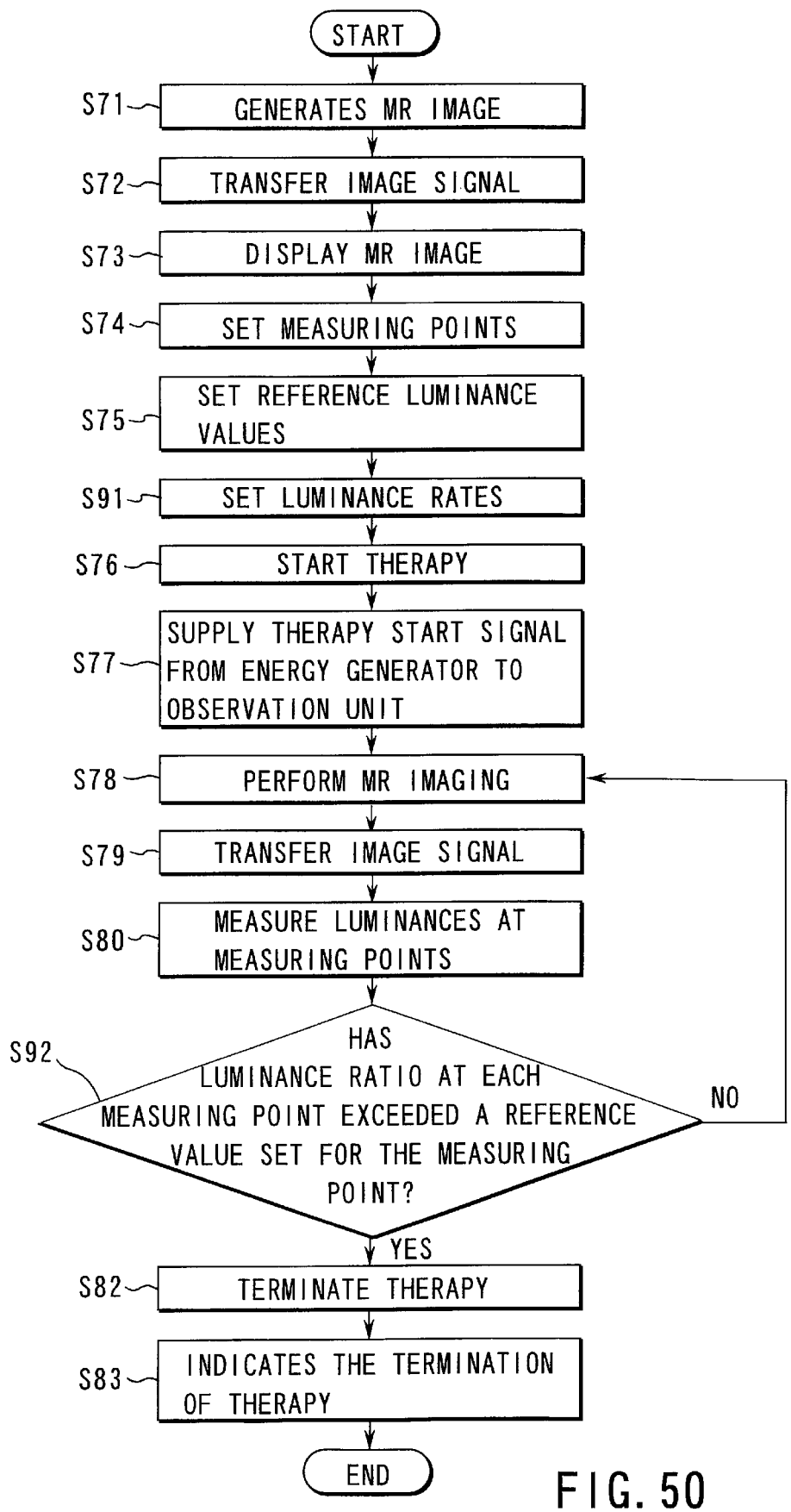
FIG. 50 is a flow chart explaining the operation of the system shown in FIG. 49.

As can be understood from FIGS. 47 and 50, Steps S71 to S75 are performed in the same order as in the twenty-fifth embodiment. After the doctor operates the input device (e.g., keyboard, mouse, track ball, touch pen, or the like), thus setting four reference luminance values Ls for the measuring points (a) to (d), respectively, in Step S75, the operation goes to Step S91.

In Step S91, the doctor operates the input device again, whereby the luminance ratio setting means 291 sets four luminance ratios for the measuring points (a) to (d), respectively. Each of the luminance ratios, thus set, is the ratio of a maximum luminance to the reference luminance Ls set for that measuring point. The maximum luminance is a value experimentally obtained, which that part of the MR image has at the measuring point when the affected region is completely treated.

Thereafter, in Step S76, the therapy is started as in the twenty-fifth embodiment. Then, Steps 77 to S80 are carried out in the same order as in the twenty-fifth embodiment. After the luminances at the measuring points (a) to (d) have been measured and displayed in Step S80, the operation goes to Step S92.

In Step S92, it is determined whether the ratio of the luminance at each measuring point to the reference luminance Ls set for the point has exceeded the luminance ratio set for the point in Step S91. If NO, the operation returns to Step S78. If YES in Step S92, the therapy is terminated in Step S82. In Step S83, the indicator means 285 of the observation unit 271 is operated, indicating that the therapy has been terminated.

The twenty-seventh embodiment is advantageous in that the affected region would not be treated excessively at all. This is because the therapy on the affected region is automatically terminated when it is determined that the ratio of the luminance at each measuring point to the reference luminance Ls set for the point has exceeded the luminance ratio set for the point.

Figure 48:
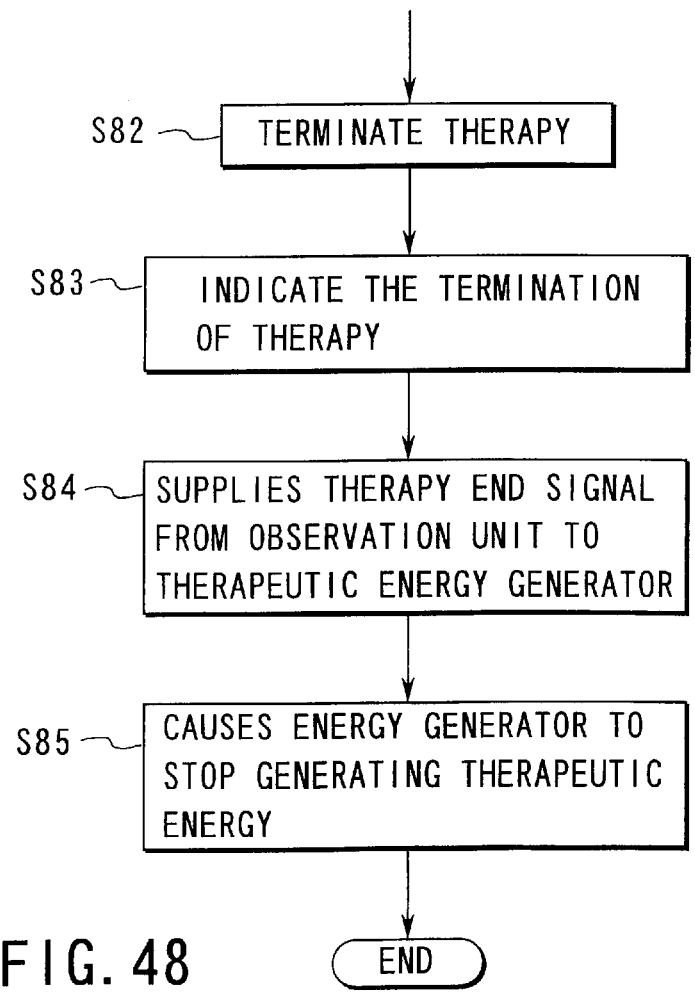
FIG. 48 is a flow chart explaining the operation of a therapeutic system according to the twenty-sixth embodiment of the invention.

In the twenty-seventh embodiment, a therapy end signal may be supplied to the therapeutic energy generator 268 as in the twenty-sixth embodiment (FIG. 48). In response to the therapy end signal, the generator 268 stops applying therapeutic energy to the affected region. Alternatively, the therapy energy applied from the probe 270 may be decreased in response to the therapy end signal.

A therapeutic system according to the twenty-eighth embodiment of the invention will be described, with reference to FIG. 51. The twenty-eighth embodiment differs from the twenty-fifth embodiment (FIGS. 43 to 47) in the operation prior to the therapy accomplished by the use of the therapeutic probe 270.

Figure 51:
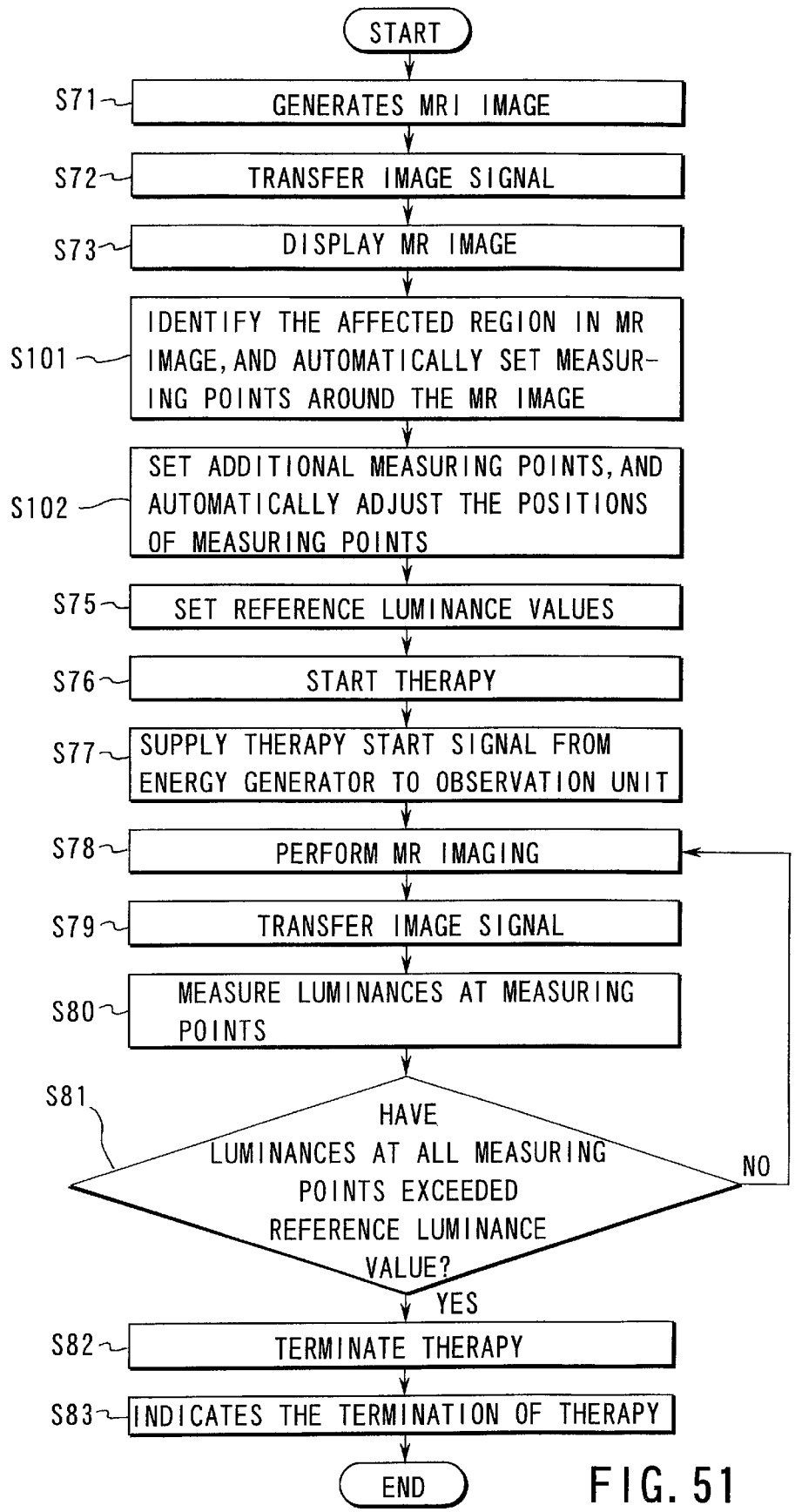
FIG. 51 is a flow chart explaining the operation of a therapeutic system according to the twenty-eighth embodiment of the invention.

As can be understood from FIGS. 47 and 51, Steps S71 to S73 are performed in the same order as in the twenty-fifth embodiment. After the display section 282 of the observation unit 271 displays the MR image in Step S73, the operation goes to Step S101. In Step S101, the MRI image displayed by the display section 282 is analyzed, thereby identifying the image Hj of the affected region and setting four measuring points (a) to (d) around the image Hj of the affected region. Then, in Step S102, the measuring-points setting section 283 sets additional measuring points around the image Hj, and the positions of the points (a) to (d) automatically set are adjusted. Thereafter, the operation goes to Step S75. Steps S75 to S83 are performed in the same order as in the twenty-fifth embodiment.

The twenty-eighth embodiment is advantageous in that the MRI apparatus 261 and the therapeutic probe 270 can be operated easily at the same time. This is because the image Hj of the affected region is automatically identified by analyzing the MR image displayed by the display section 282, and the measuring points (a) to (d) are then set around the image Hj of the affected region.

A therapeutic system according to the twenty-ninth embodiment of the invention will be described, with reference to FIG. 52. The twenty-ninth embodiment differs from the twenty-seventh embodiment (FIGS. 49 to 50) in the operation after the therapy accomplished by the use of the therapeutic probe 270.

Figure 52:
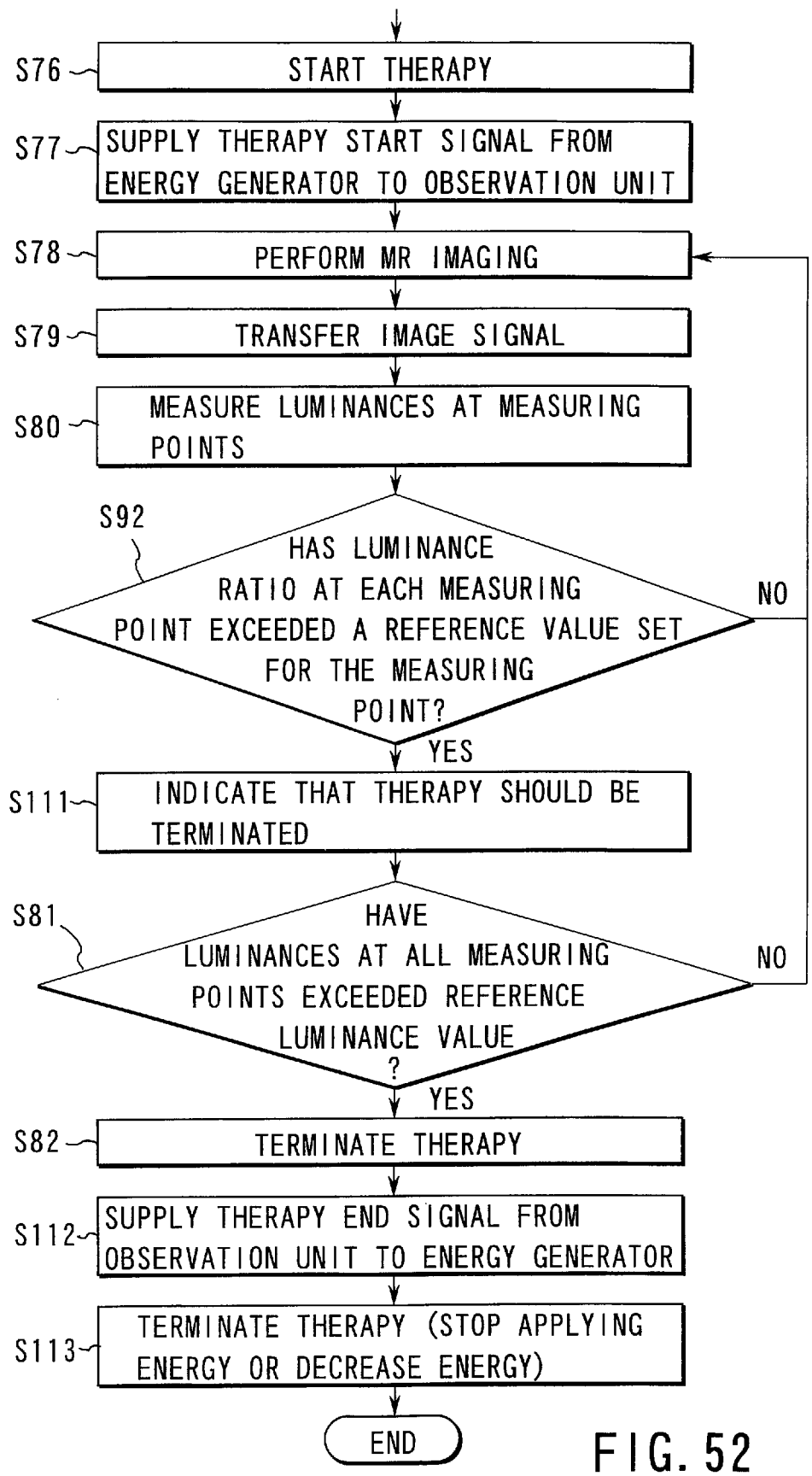
FIG. 52 is a flow chart explaining the operation of a therapeutic system according to the twenty-ninth embodiment of this invention.

As can be understood from FIGS. 50 and 52, Steps S71 to S92 are performed in the same order as in the twenty-seventh embodiment. If it is determined in Step S92 that the ratio of the luminance at each measuring point to the reference luminance Ls set for the point has exceeded the luminance ratio set for the point, the operation goes to Step S111.

In Step S111, the indicator means 285 of the observation unit 271 is operated, indicating that the therapy should be terminated. The operation then goes to Step S81 that is identical to Step S81 shown in the flow chart of FIG. 47 that explains the operation of the twenty-fifth embodiment (FIGS. 43 to 47). In Step S81, it is determined whether all luminances at the points (a) to (d) exceed the reference luminance values Ls, respectively. If NO, the operation returns to Step 78. If YES, the therapy is terminated in Step S82.

Then, in Step S112, the observation unit 271 supplies a therapy end signal to the therapeutic energy generator 268. In Step S113, the generator 268 stops applying therapeutic energy to the affected region, whereby the therapy is terminated. More precisely, the therapeutic probe 270 stops applying the energy in response to the therapy end signal. Alternatively, the therapy energy applied from the probe 270 may be decreased in response to the therapy end signal, thereby to terminate the therapy automatically.

The twenty-ninth embodiment described above is advantageous in that the therapy is automatically terminated in safety. This is because the indicator means 285 is operated, indicating that the therapy should be terminated, when it is determined that the ratio of the luminance at each measuring point to the reference luminance Ls set for the point has exceeded the luminance ratio set for the point. Then, the therapeutic energy generator 268 stops applying therapeutic energy to the affected region.

Figure 53:
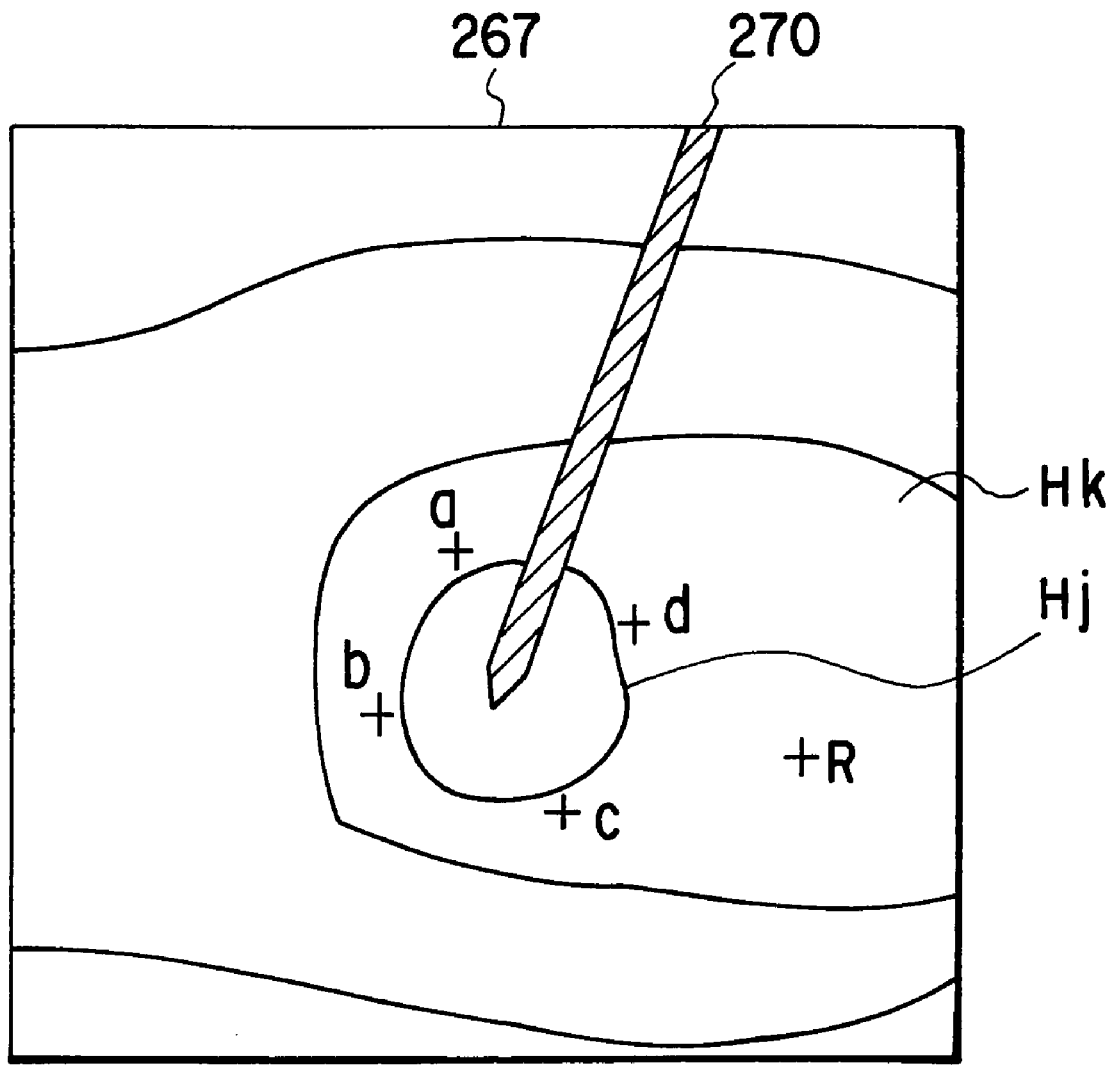
FIG. 53 is a diagram illustrating the image displayed by the display provided in the observation unit incorporated in a therapeutic system according to the thirtieth embodiment of the present invention.
Figure 54:
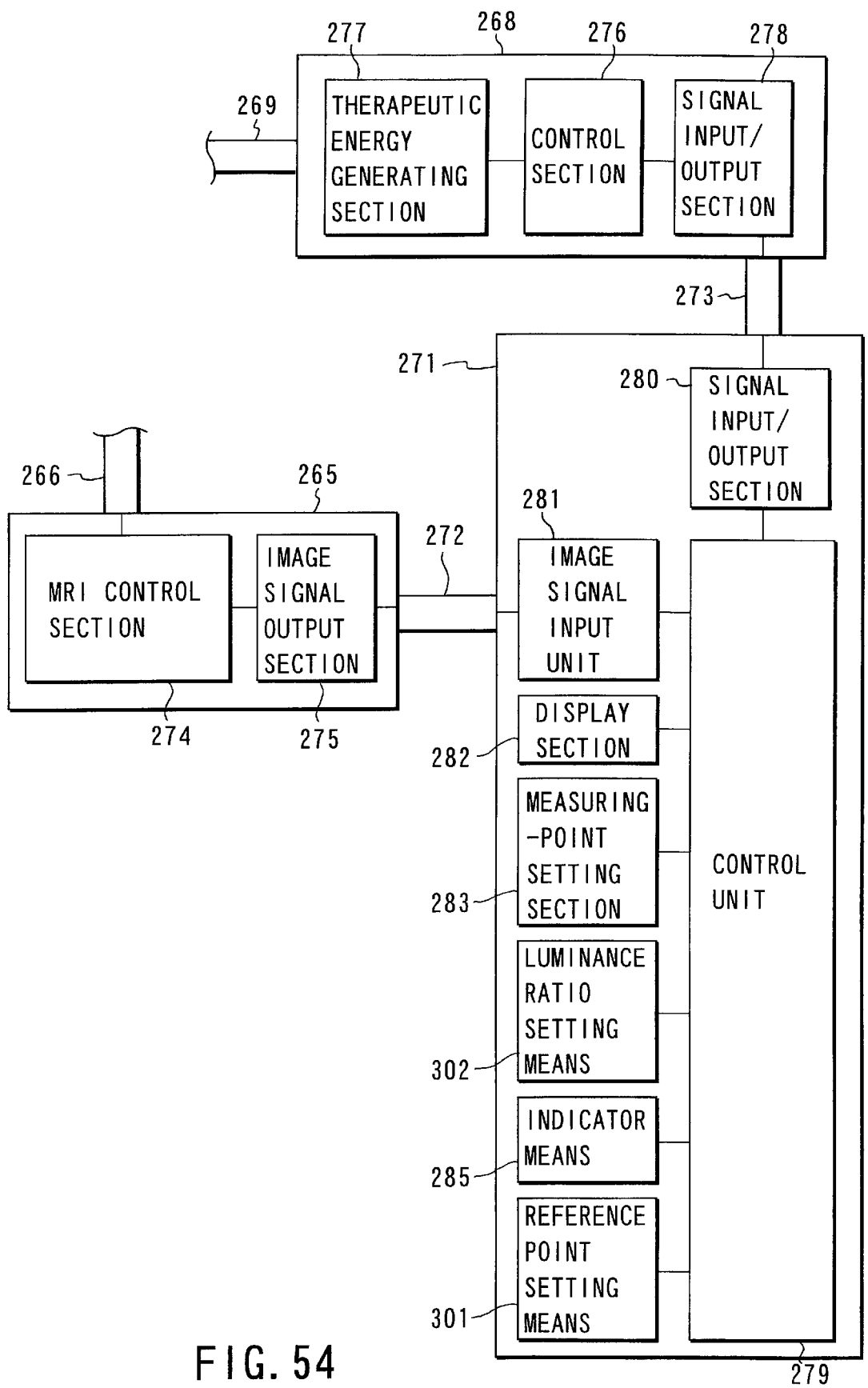
FIG. 54 is a block diagram depicting the observation unit provided in the thirtieth embodiment.
Figure 55:
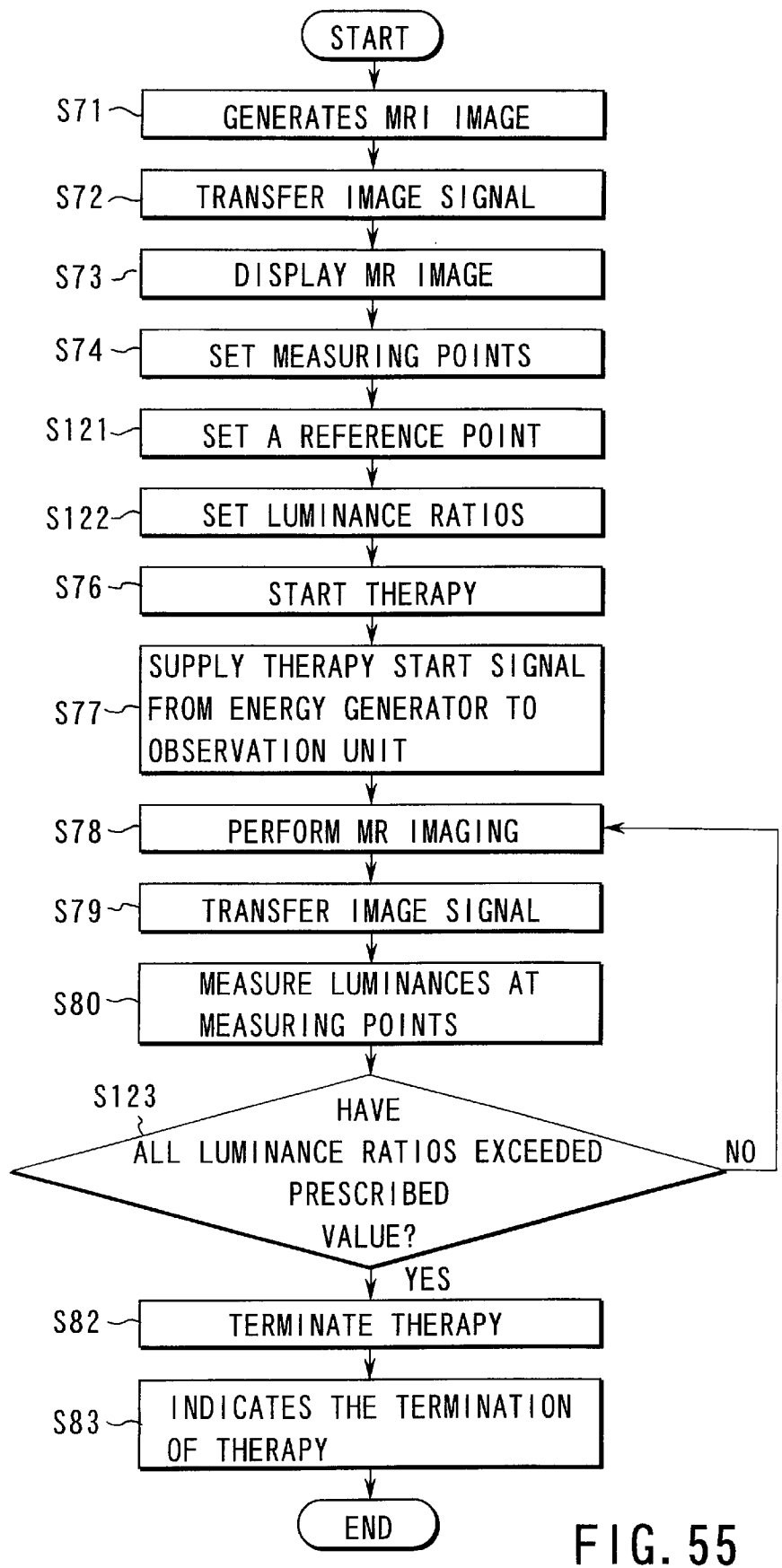
FIG. 55 is a flow chart explaining the operation of the thirtieth embodiment.

FIGS. 53 to 55 show a therapeutic system, which is the thirtieth embodiment of the present invention. The thirtieth embodiment differs from the twenty-fifth embodiment (FIGS. 43 to 47) in the following respects.

As shown in FIG. 54, the observation unit 271 has an additional component, i.e., a reference point setting means 301. The reference point setting means 301 is designed to set a reference point R in the MR image generated by the MRI apparatus 262, while the measuring-points setting section 283 sets four measuring points (a) to (d). Furthermore, the reference luminance values Ls are not set for the four measuring points (a) to (d) as in the twenty-fifth embodiment. Instead, a luminance ratio setting means 302 sets ratio of each reference luminance value Ls to the reference luminance value for the reference point R.

As shown in FIG. 53, the reference point R is set in the MR image Hk of a region that surrounds the image Hj of the affected region and that is supposed to be not influenced by the therapeutic energy applied from the probe 270. The therapeutic system is operated as will be explained below, with reference to the flow chart of FIG. 55.

As can be understood from FIGS. 47 and 55, Steps S71 to S74 are performed in the same order as in the twenty-fifth embodiment (FIGS. 43 to 47). After the four measuring points (a) to (d) have been set around the image Hj of the affected region as shown in FIG. 53, the operation goes to Step S121. In Step S121, the input device (e.g., keyboard, mouse, track ball, touch pen, or the like) is operated, whereby the reference point setting means 301 sets a reference point R in the image Hk as is illustrated in FIG. 53. In Step S122, the input device (not shown) is operated again, whereby the luminance ratio setting means 302 sets the ratios of the four reference luminance values Ls set for the measuring points (a) to (d) to the reference luminance value set for the reference point R.

Thereafter, in Step S76, the therapy is started in the same way as in the twenty-fifth embodiment. Steps S76 to S80 are carried out in the same order as in the twenty-fifth embodiment. After the luminances at the four measuring points (a) to (d) are measured and displayed in Step S80, the operation goes to Step S123.

In Step S123, it is determined whether all four luminance ratios set by the luminance ratio setting means 302 have exceeded a prescribed value or not. If NO, the operation returns to Step S78. If YES, the operation goes to Step S82, in which the therapy is terminated. In Step S83, the indicator means 285 informs that the therapy has been terminated.

The thirtieth embodiment is advantageous in that the termination of therapy is reliably recognized. This is because The reference point setting means 301 sets a reference point R in the MR image generated by the MRI apparatus 262, and the luminance ratio setting means 302 sets the ratios of the four reference luminance values Ls to the reference luminance value set for the reference point R. Thus, the influence of individual differences or MRI parameters on the luminance at each measuring point can be compensated for.

Figure 56:
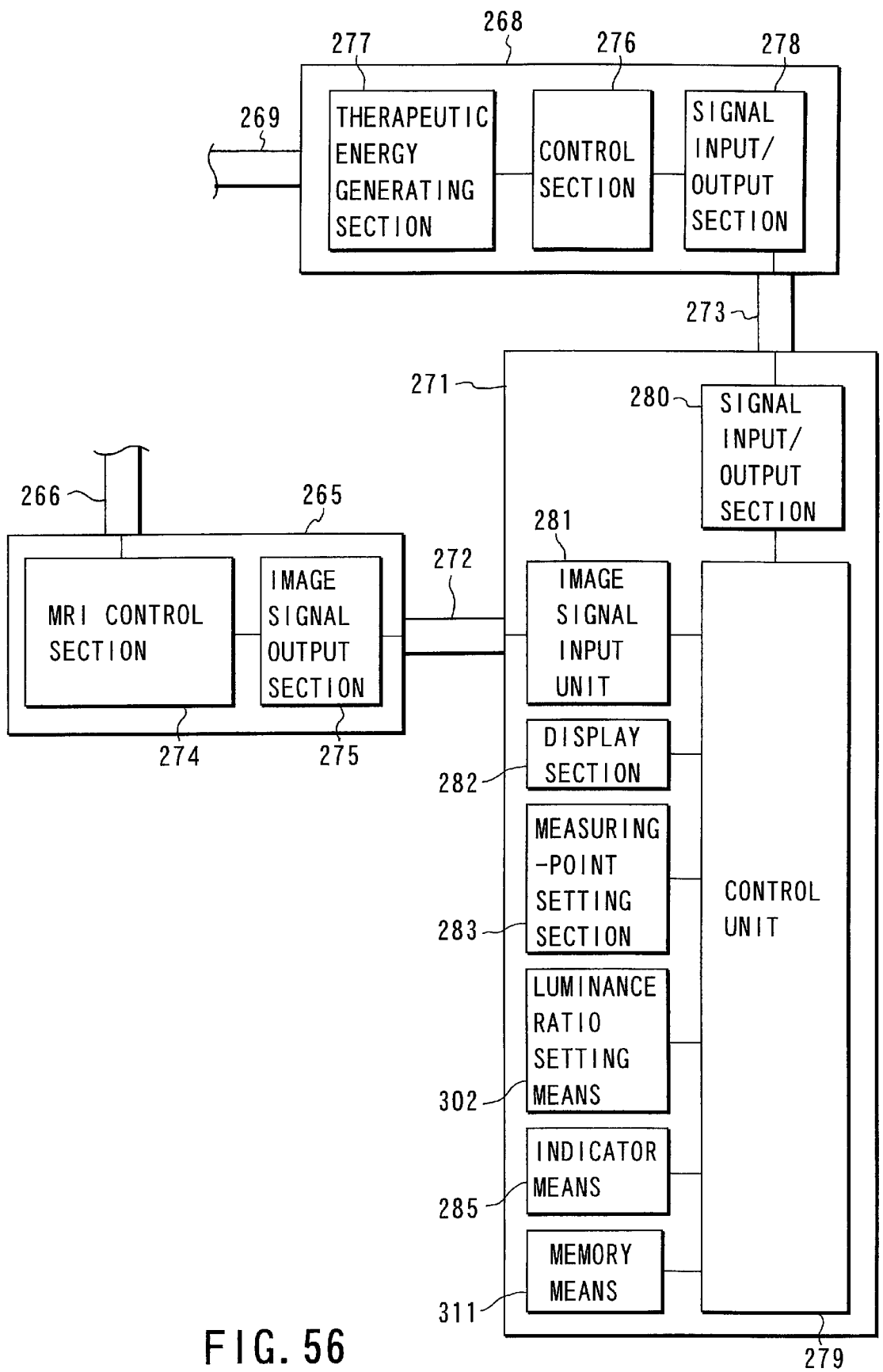
FIG. 56 is a block diagram of the observation unit incorporated in a therapeutic system according to the thirty-first embodiment of the present invention.
Figure 57:
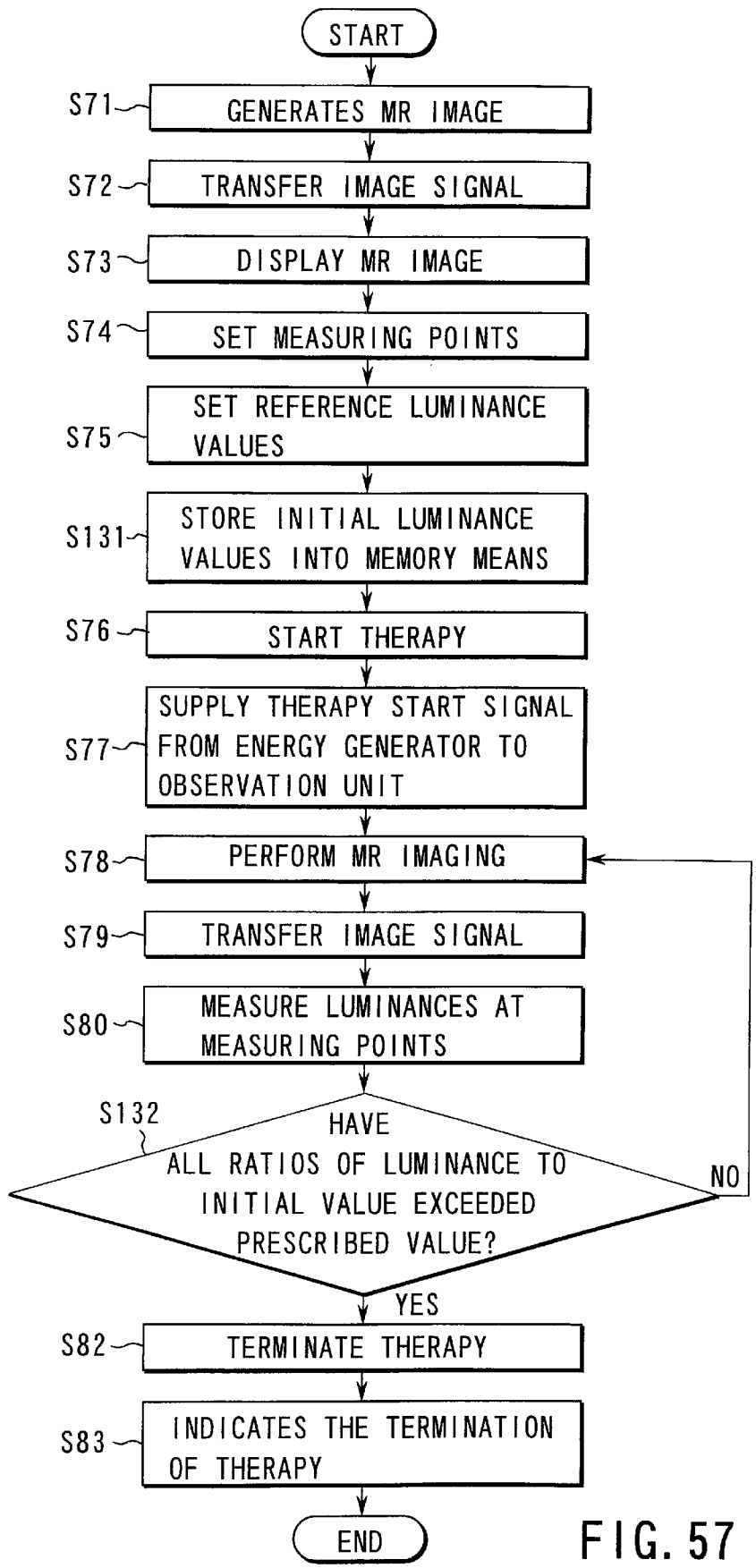
FIG. 57 is a flow chart explaining the operation of the thirty-first embodiment.

FIGS. 56 and 57 show a therapeutic system according to the thirty-first embodiment of the present invention. This embodiment differs from the thirtieth embodiment in the following respects.

As shown in FIG. 56, the observation unit 271 incorporates a memory means 311, instead of the reference point setting means 301. The memory means 311 is provided for storing the initial values of the luminances at the measuring points (a) to (d).

The operation of the thirty-first embodiment will be explained, with reference to the flow chart of FIG. 57.

As can be understood from FIGS. 47 and 57, Steps S71 to S75 are performed in the same order as in the twenty-fifth embodiment (FIGS. 43 to 47). After the reference luminance value Ls for the four measuring points (a) to (d) have been set in Step S75, the operation goes to Step S131. In Step 131, the initial luminance values Ls set for the points (a) to (d) are stored into the memory means 311.

Then, the therapy is started in Steps S76 in the same way as in the thirtieth embodiment. Steps S77 to S80 are carried out in the same order as in the thirtieth embodiment. After the luminances at the four measuring points (a) to (d) are measured and displayed in Step S80, the operation goes to Step S132. In Step S132, it is determined whether all four ratios of the luminances at the measuring points (a) to (d) to the initial values stored in the memory means 311 have exceeded a prescribed value or not. If YES, the operation goes to Step S82, in which the therapy is terminated. In this case, the indicator means 285 informs, in Step S83, that the therapy has been terminated. If NO in Step S132, the operation returns to Step S78, whereby Steps S78, S79, S80 and S132 are repeated.

In the thirty-first embodiment described above, the memory means 311 stores the initial luminance values Ls set for the points (a) to (d). The therapy is terminated when the ratios of the luminances at the points (a) to (d) set around the image Hj of the affected region, to the initial values stored in the memory means 311 have exceeded a prescribed value. Therefore, the thirty-first embodiment attains the same advantage as the thirtieth embodiment. In addition, the thirty-first embodiment can be used to perform therapy on an organ so small that the reference point R can hardly set in an MR image generated by the MRI apparatus 262.

Figure 58:
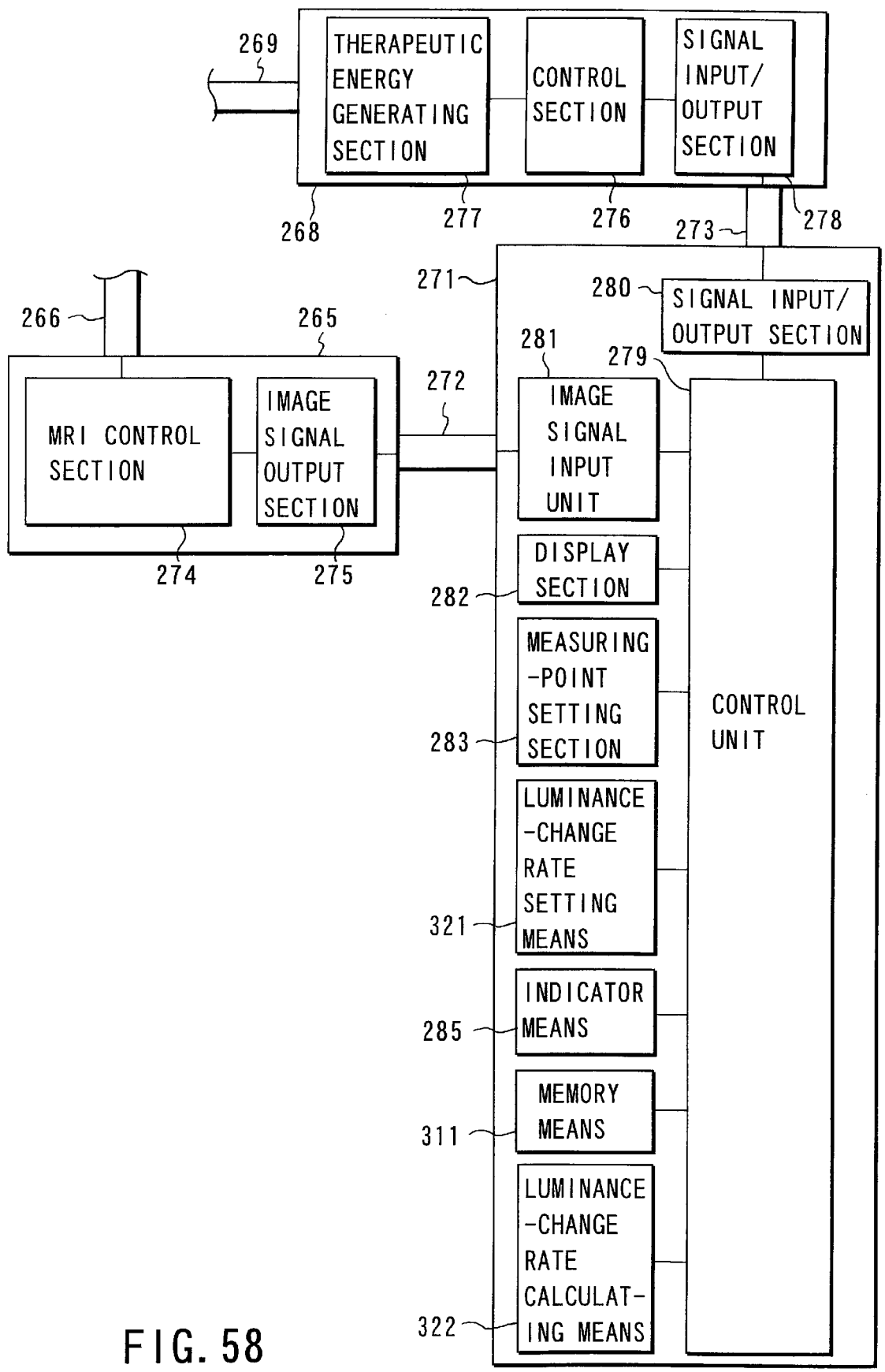
FIG. 58 is a block diagram of the observation unit incorporated in a therapeutic system according to the thirty-second embodiment of the present invention.
Figure 59:
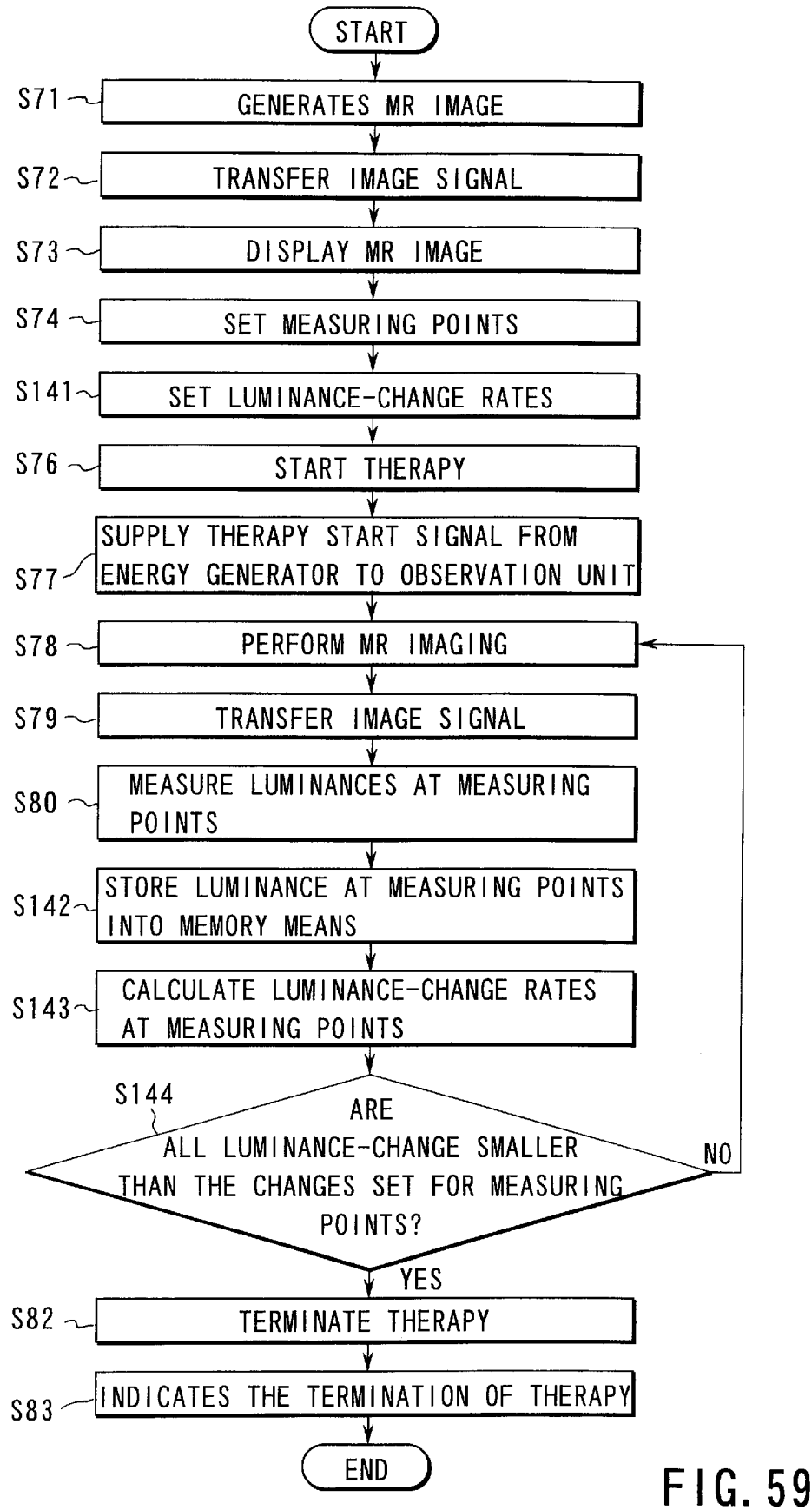
FIG. 59 is a flow chart explaining the operation of the thirty-second embodiment.

FIGS. 58 and 59 show a therapeutic system according to the thirty-second embodiment of the present invention. This embodiment differs from the thirty-first embodiment in the following respects.

As shown in FIG. 58, the observation unit 271 incorporates a luminance-change rate setting means 321 and a luminance-change rate calculating means 322, instead of the luminance rate setting means 302. Whether or not the therapy has should be terminated is determined in accordance with the luminance-change rates at the measuring points (a) to (d). The decision is not made in accordance with the luminances measured at the points (a) to (d) as in the thirty-first embodiment.

The operation of the thirty-second embodiment will be explained, with reference to the flow chart of FIG. 59. Steps S71 to S74 are carried out in the same order as in the twenty-fifth embodiment (FIGS. 45 to 47). After the four measuring points (a) to (d) have been set around the image Hj of the affected region, the operation goes to Step S141. In Step S141, the input device (e.g., keyboard, mouse, track ball, touch pen, or the like) is operated, whereby the luminance-change rate setting means 321 sets four luminance-change rates for the measuring points (a) to (d), respectively.

Thereafter, in Step S76, the therapy is started in the same way as in the twenty-fifth embodiment. Steps S77 to S80 are then performed in the same order as in the twenty-fifth embodiment. After the luminances at the four measuring points (a) to (d) are measured and displayed in Step S80, the operation goes to Step S142. In Step S142, the luminances at the points (a) to (d) are stored into the memory means 311. In Step S143, the luminance-change rate calculating means 322 calculates the luminance-change rates at the points (a) to (d). In Step S144, it is determined whether all luminance-change rates calculated are smaller than the four luminance-change rates that the luminance-change rate setting means 321 has set for the measuring points (a) to (d). If NO, the operation returns to Step S78. In this case, Steps S78 to S80 and Steps S141 to S143 are repeated. If YES in Step S144, the operation goes to Step S82, in which the therapy is terminated. In Step S83, the indicator means 285 informs that the therapy has been terminated.

In the thirty-second embodiment described above, whether the therapy should be terminated is determined in accordance with the luminance-change rates at the measuring points (a) to (d), not in accordance with the luminances measured at the points (a) to (d). In this regard, it should be noted that the luminance at any point in the image Hj of the affected region will not change once the affected region has been heated, becoming completely void of water. This is why the luminance-change rates at the measuring points (a) to (d) are monitored in the thirty-second embodiment. The thirty-second embodiment is advantageous in that it can be reliably determined whether the living tissues present in the affected region have perished.

FIGS. 60 to 63 show a therapeutic system, which is the thirty-third embodiment of this invention. The present embodiment differs from the thirty-second embodiment (FIGS. 58 and 59) in the following respects.

Figure 60:
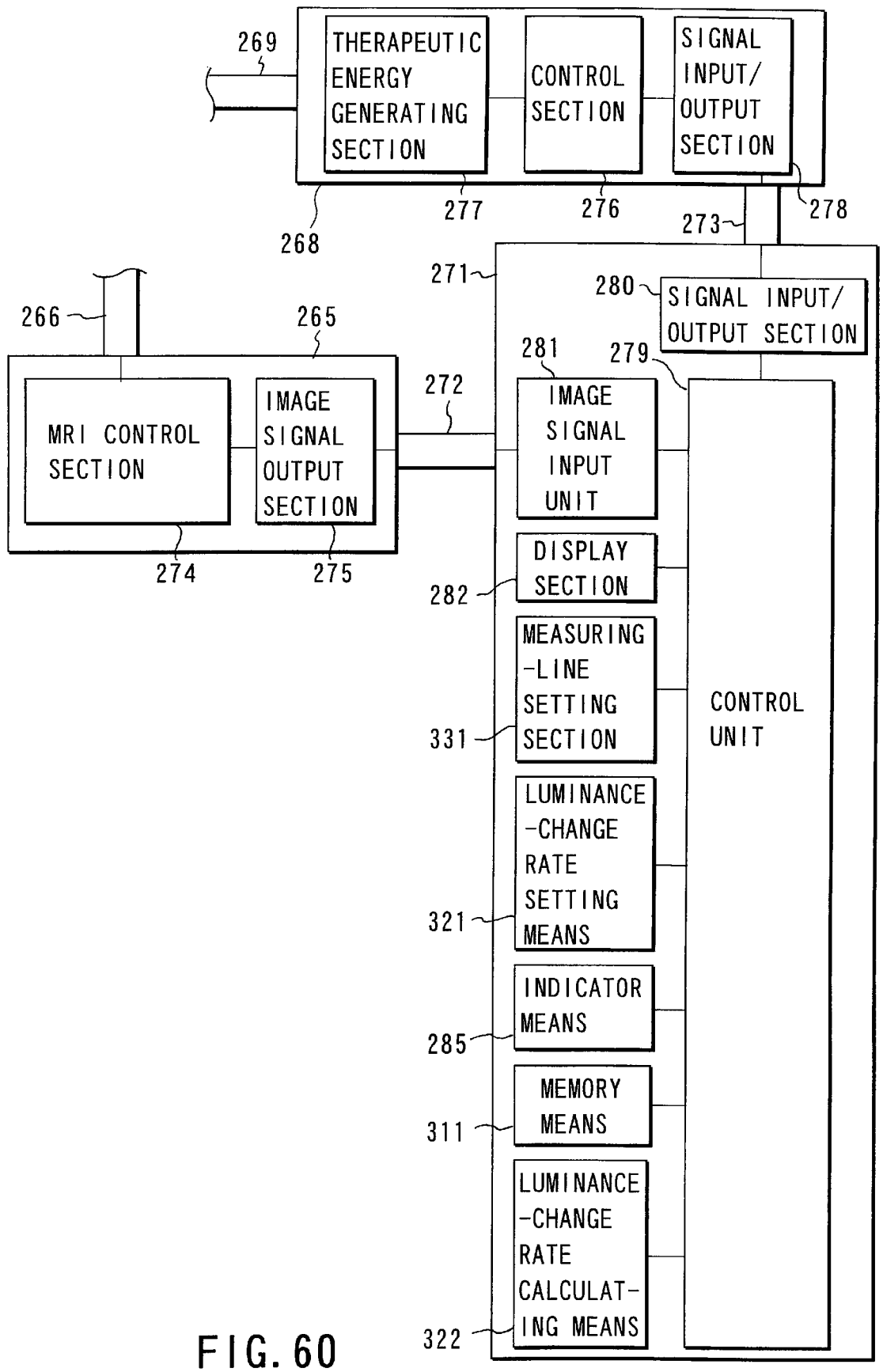
FIG. 60 is a block diagram of the observation unit incorporated in a therapeutic system according to the thirty-third embodiment of the present invention.
Figure 62:
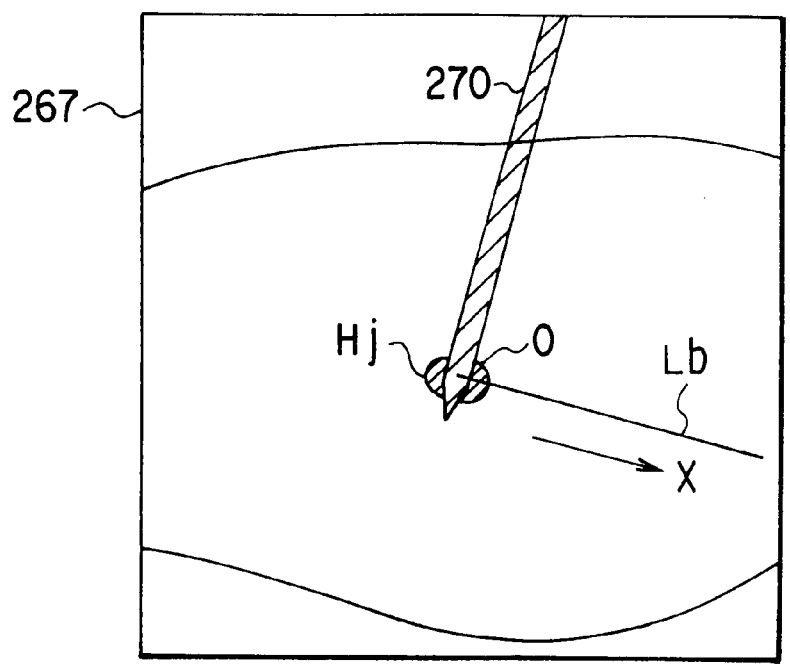
FIG. 62 is a diagram showing a part of the image displayed by the display provided in the observation unit incorporated in the thirty-third embodiment.

As shown in FIG. 60, the observation unit 271 incorporates a reference line setting means 331, instead of the measuring-points setting section 283. The reference-line setting means 331 is designed to set a reference line Lb in the MR image generated by the MRI apparatus 262, as illustrated in FIG. 62. The reference line Lb extends in a given direction from the energy-emission center 0 of the therapeutic probe 270, from which therapeutic energy is applied to the affected region Hj. A plurality of measuring points are set on the reference line Lb and spaced at regular intervals. Luminaces at these points are measured.

The operation of the thirty-third embodiment will be described with reference to the flow chart of FIG. 61.

Figure 61:
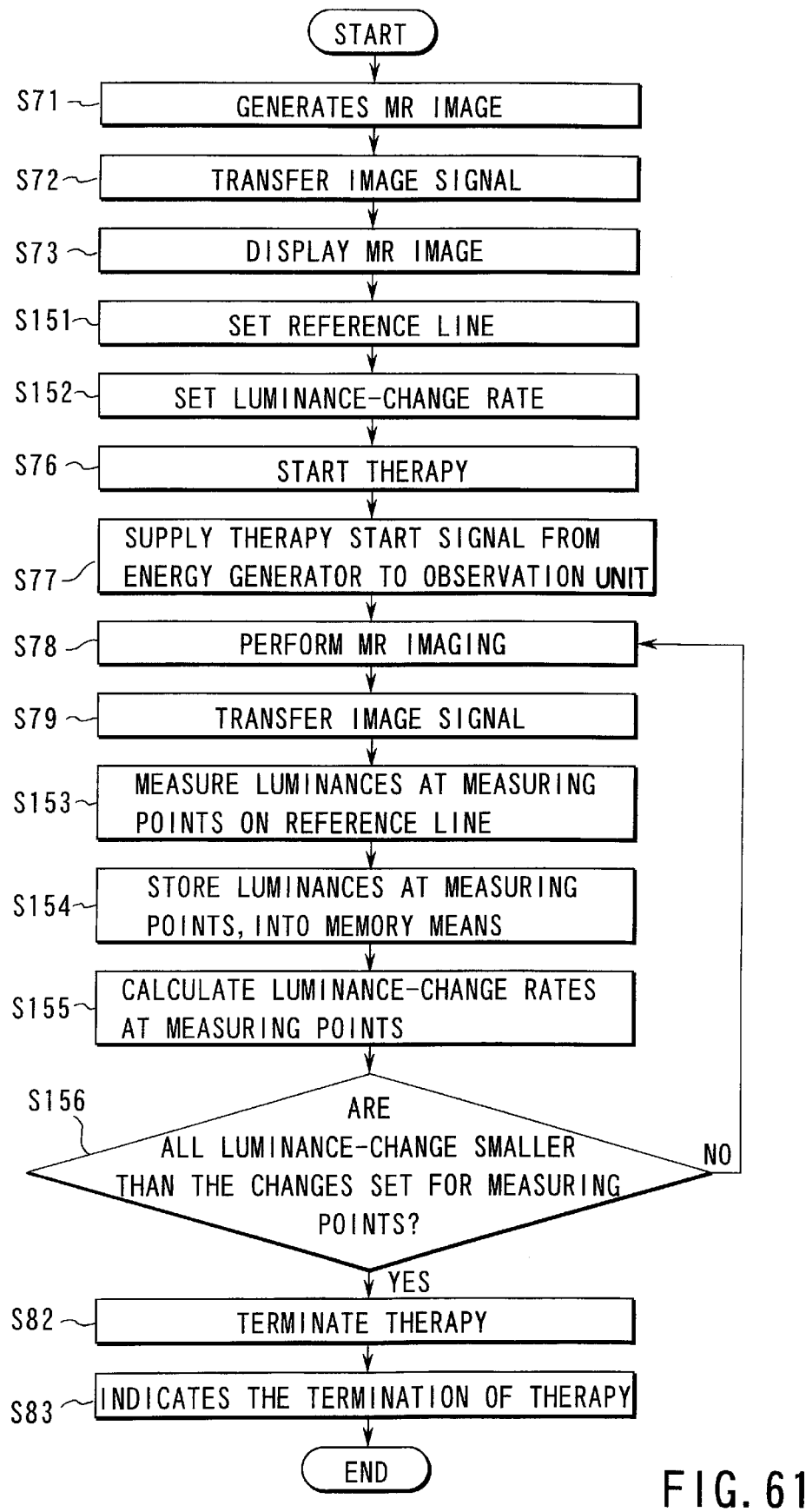
FIG. 61 is a flow chart explaining the operation of the thirty-third embodiment.

As shown in FIG. 61, Steps S71 to S73 are carried out in the same order as in the twenty-fifth embodiment (FIGS. 45 to 47). After the display section 282 of the observation unit 271 displays the MR image in Step S73, the operation goes to Step S151. In Step S151, the input device (e.g., keyboard, mouse, track ball, touch pen, or the like) is operated, whereby the reference-line setting means 331 sets a reference line Lb in the RM image generated by the MRI apparatus 262. In Step S152, the input device (not shown) is operated again, whereby the luminance-change rate setting means 321 sets a luminance-change rate for the reference line Lb.

Then, in Step S76, the therapy is started in the same way as in the twenty-fifth embodiment. Steps S77 to S79 are then performed in the same order as in the twenty-fifth embodiment. After the MRI controller 265 transfers an image signal to the observation unit 271 in Step S79, the operation goes to Step S153.

In Step S153, the luminances at the measuring points on the reference line Lb are measured and displayed. Then, in Step S154, the luminaces measured at these measuring points are stored into the memory means 311. In Step S155, the luminance-change rate calculating means 322 calculates the luminance-change rates at the measuring points.

Next, in Step S156, it is determined whether all luminance-change rates calculated for all measuring points are smaller than the four luminance-change rates that the means 321 has set for the measuring points. If NO, the operation returns to Step S78. If YES in Step S156, the operation goes to Step S82, in which the therapy is terminated. In Step S83, the indicator means 285 informs that the therapy has been terminated.

Figure 63:
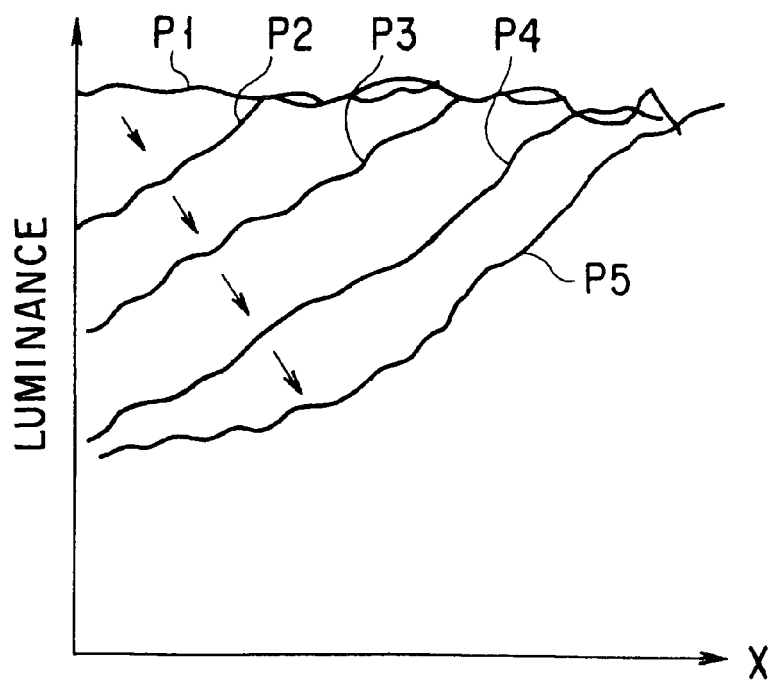
FIG. 63 is a graph illustrating how luminance changes along the reference line set in an MR image generated in the thirty-third embodiment.

FIG. 63 shows how the luminance changes along the reference line Lb set in the MR image generated by the MRI apparatus 262, during the therapy accomplished by the use of the therapeutic probe 270. In FIG. 63, the distance from the therapeutic probe 270 is plotted on the X axis, and the luminance on the Y axis. While the probe 270 applies the therapeutic energy, the luminance distribution changes with time as is indicated by curves P1 to P5. As can be understood from FIG. 63, the luminance stops increasing once it reaches a specific value. The display section 282 of the observation unit 271 displays the curves P1 to P5. Alternatively, the display section 282 may display the luminance-change rates at some measuring points on the reference line Lb, in the form of such a bar graph as is shown in FIG. 39.

As mentioned above, a reference line Lb is set which extends in a given direction from the energy-mission center O of the therapeutic probe 270 applying therapeutic energy to the affected region Hj, and luminance-change rates at some measuring points automatically set on the reference line Lb are measured. On the basis of the luminance-change rates measured it is determined whether or not the therapy should be terminated.

As the therapeutic probe 270 applies the therapeutic energy to the affected region Hj, the temperature in the region Hj gradually rises. Once the region Hj has become completely void of water, there are no longer changes in the water content in the affected region Hj. In other words, the luminance at any measuring point no longer change, however much energy is applied to the affected region Hj. Thus, it is reliably determined that the therapy should be terminated, because luminance-change rates are measured at some measuring points which have been automatically set on the reference line Lb extending from the energy-emission center O of the therapeutic probe 270.

Figure 64:
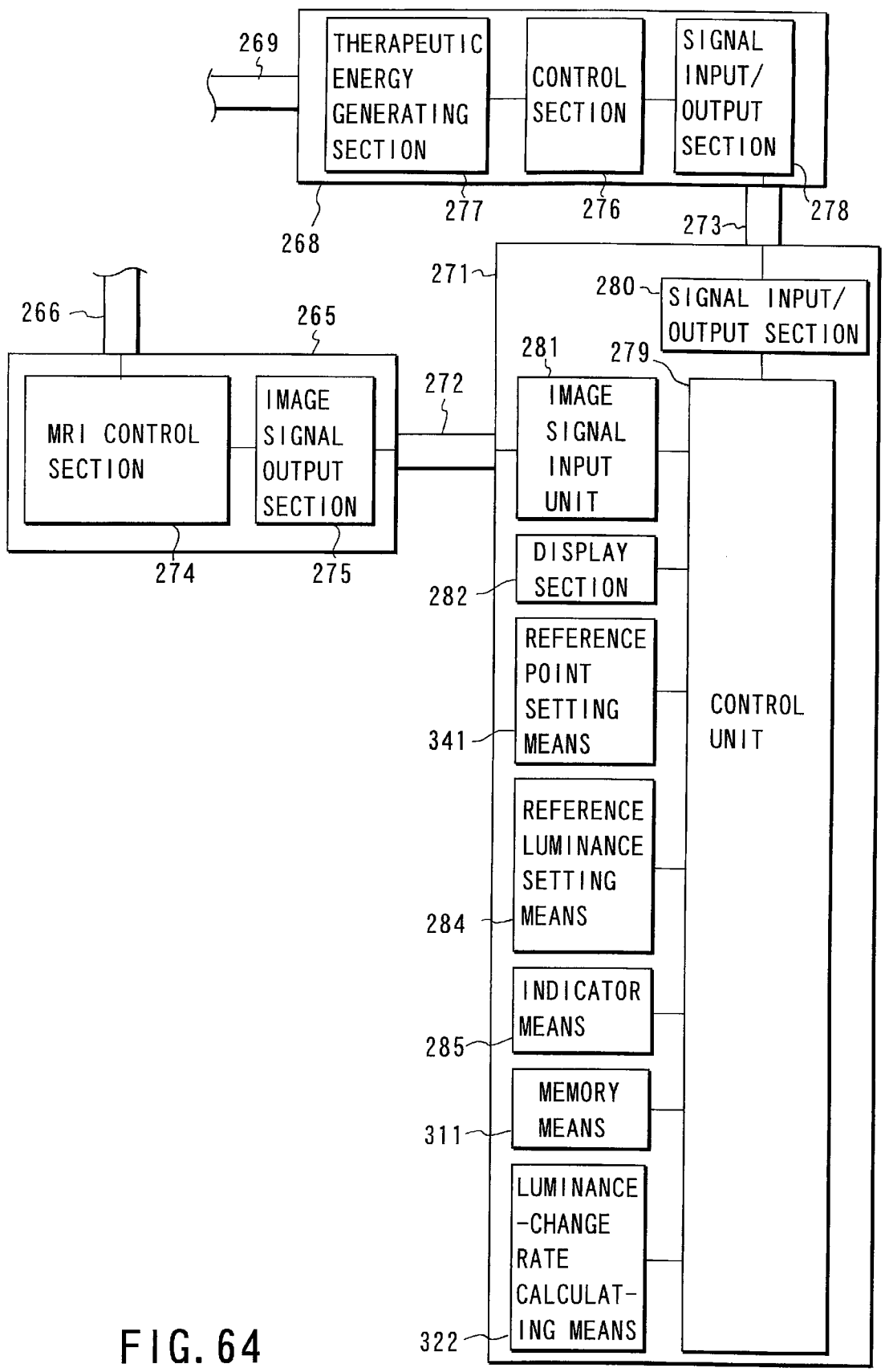
FIG. 64 is a block diagram showing the observation unit provided in a therapeutic system according to the thirty-four embodiment of the present invention.
Figure 65:
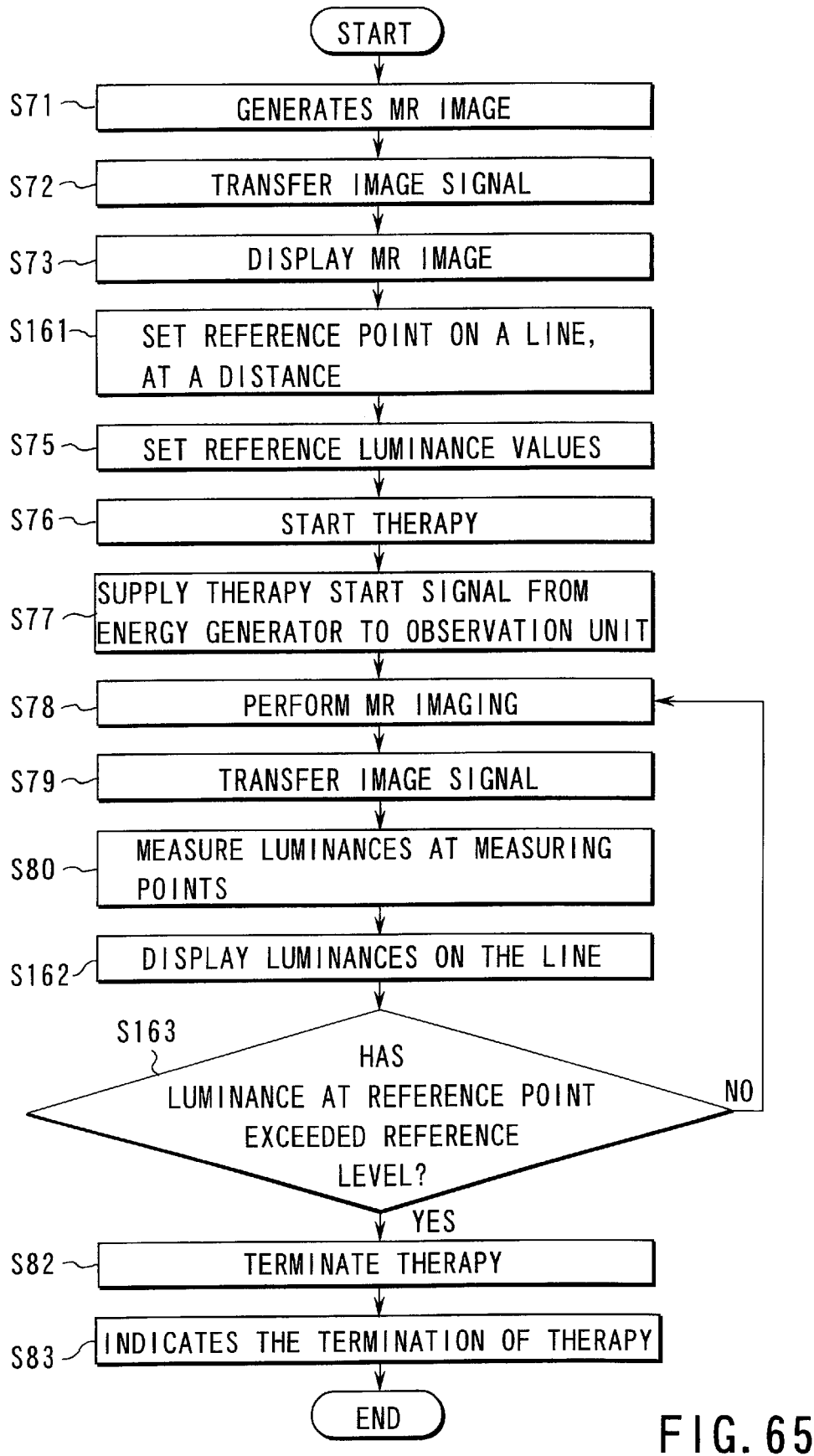
FIG. 65 is a flow chart explaining the operation of the thirty-fourth embodiment.
Figure 66:
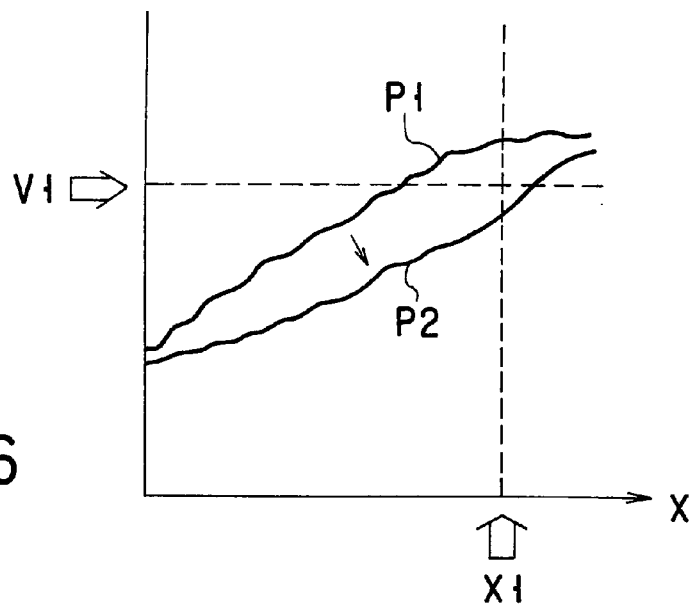
FIG. 66 is a diagram showing an MR image displayed by the display section incorporated in the observation unit of the thirty-fourth embodiment.

FIGS. 64 to 66 show a therapeutic system according to the thirty-fourth embodiment of the present invention. The thirty-fourth embodiment differs from the thirty-third embodiment (FIGS. 60 to 63) in the following respects.

As shown in FIG. 64, the observation unit 271 incorporates a reference point setting means 341 and a reference luminance setting means 284, instead of the reference line setting means 331 and the luminance-change rate setting means 321.

The operation of the therapeutic system, which is the thirty-fourth embodiment, will be explained with reference to the flow chart of FIG. 65.

Steps S71 to S73 are carried out in the same order as in the twenty-fifth embodiment (FIGS. 45 to 47) and as is illustrated in the flow chart of FIG. 47. After the display section 282 of the observation unit 271 displays the MR image in Step S73, the operation goes to Step S161. In Step S161, the input device (e.g., keyboard, mouse, track ball, touch pen, or the like) is operated, whereby the reference point setting means 341 sets a reference point X1 in the image of the affected region.

Thereafter, in Step S76, the therapy is started as in the twenty-fifth embodiment. Steps S77 to S80 are then performed in the same order as in the twenty-fifth embodiment. In Step S80, the luminance at the reference point X1 is measured. In Step S163, it is determined whether or not the luminance at the reference point X1 has exceeded the reference level V1 set by the luminance setting means 284. If NO, the operation returns to Step S78. If YES, the operation goes to Step S82, the operation goes to Step S83. In Step S83, the indicator means 285 of the observation unit 271 informs that the therapy has been terminated.

As the therapeutic probe 270 applies the therapeutic energy to the affected region Hj (i.e., living tissues), heat propagates like ripples, from the energy-emission center O in the RMI tomogram of the affected region Hj. Therefore, it can be confirmed how much the affected region Hj has been treated, by comparing the reference level V1 set by the luminance setting means 284 with the luminance at the reference point X1 which is at a certain distance from the energy-emission center O.

Moreover, the display section 282 of the observation unit 271 displays the relation between the luminance measured at the point set by the reference point setting means 341 and the distance between this point and the energy-emission center O, as is illustrated in FIG. 66. It is therefore easy for a doctor to visually understand how much the affected region Hj has been treated. If the relation is represented by a curve P1, indicating that the luminance at distance X1 is higher than the reference level V1, the doctor recognizes that the therapy can be continued. On the other hand, if the relation is represented by a curve P2, indicating that the luminance at distance X1 is lower than the reference level V1, the doctor understands that the therapy should be terminated.

Thus, the thirty-fourth embodiment is advantageous in that the doctor can visually understand how much the affected region Hj has been treated, merely by looking at the luminance-distance curve displayed by the display section 282 of the observation unit 271.

Figure 67:
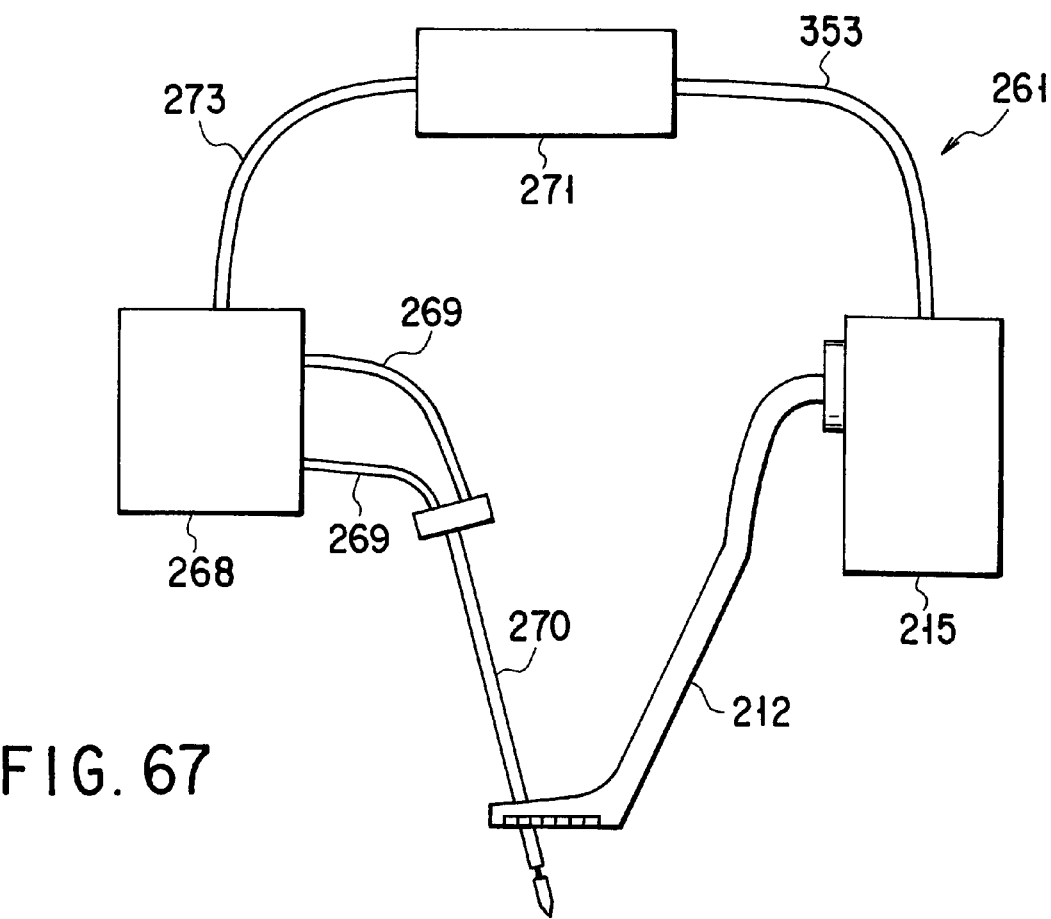
FIG. 67 is a schematic representation of a therapeutic system according to the thirty-fifth embodiment of the present invention.
Figure 68:
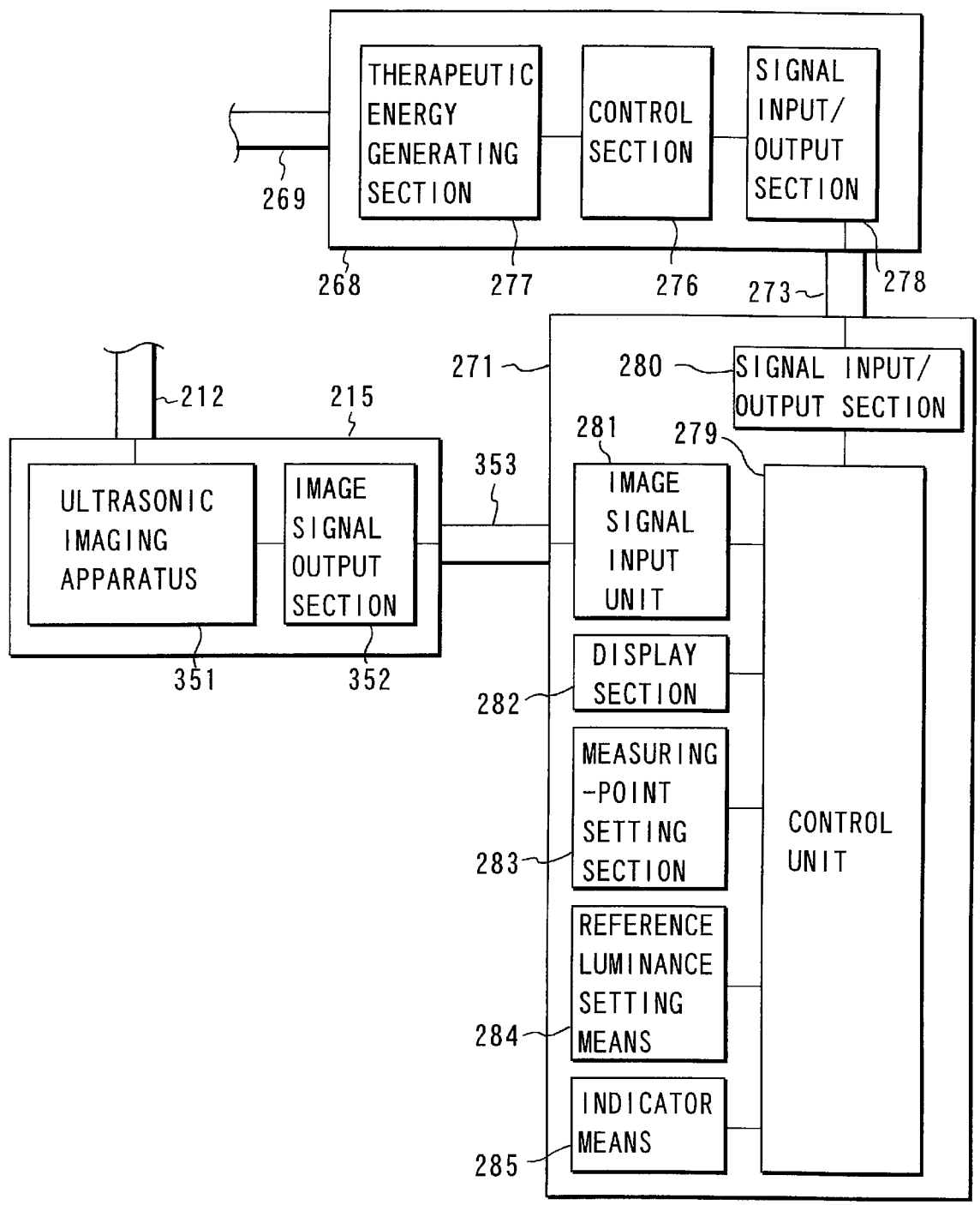
FIG. 68 is a block diagram depicting the observation unit provided in the thirty-fifth embodiment.
Figure 69:
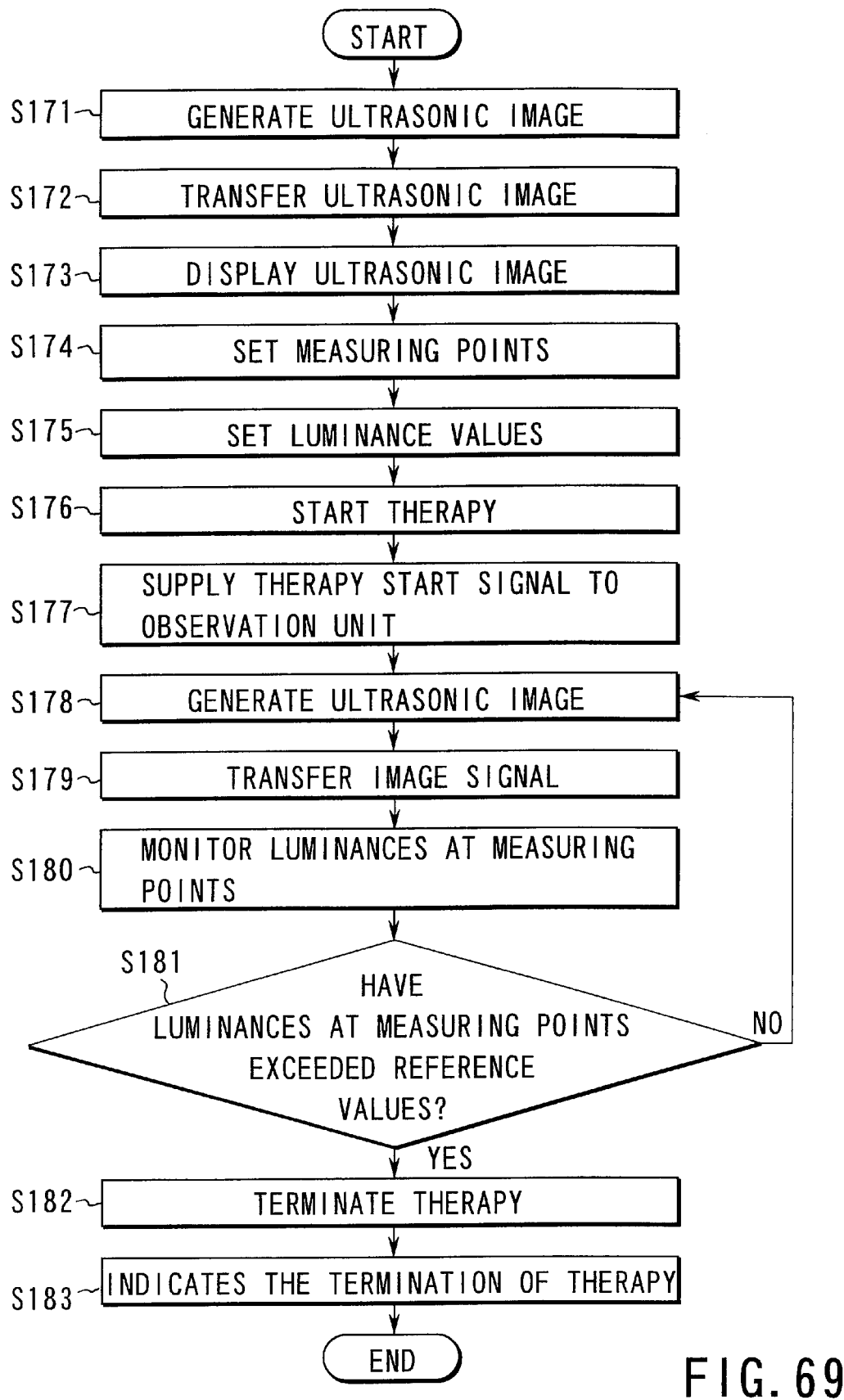
FIG. 69 is a flow chart explaining the operation of the thirty-fifth embodiment.

FIGS. 67 to 69 show a therapeutic system according to the thirty-fifth embodiment of the invention. The thirty-fifth embodiment differs from the twenty-fifth embodiment (FIGS. 45 to 47) in the following respects.

As shown in FIG. 67, an ultrasonic imaging apparatus 215 is provided, instead of the MRI apparatus 262, for detecting the position of the therapeutic probe 270. The ultrasonic imaging apparatus 215 is, for example, of the same type as the one used in the twenty-second embodiment (FIG. 40).

As shown in FIG. 68, the ultrasonic imaging apparatus 215 comprises an ultrasonic imaging section 351 and an image signal output section 352. A diagnostic ultrasonic probe 212 is connected to the input of the ultrasonic imaging section 351. The image signal input unit 281 of the observation unit 271 is connected to the image signal output section 352 by the signal cable 353.

The therapeutic system shown in FIG. 67 is operated as will be described below, with reference to the flow chart of FIG. 69.

First, the diagnostic ultrasonic probe 212 generates an ultrasonic image in Step S171, prior to the therapy performed by means of the therapeutic probe 270. In Step S172, the image signal representing the ultrasonic image is transferred from the ultrasonic imaging apparatus 215 to the observation unit 271. In Step S173, the display section 282 of the observation unit 271 displays the ultrasonic image the ultrasonic probe 212 has generated.

Thereafter, in Step S174, the doctor operates the input device (e.g., keyboard, mouse, track ball, touch pen, or the like), while observing the ultrasonic image displayed on the screen of the display section 282 of the observation unit 271. As a result, the measuring-points setting section 283 of the observation unit 271 sets four measuring points (a) to (d) in the ultrasonic image, around the image Hj of the affected region as is illustrated in FIG. 44. In Step S175, the doctor operates the input device again, while observing the ultrasonic image, setting four reference luminance values Ls for the measuring points (a) to (d), respectively.

In Step S176, the therapy is started. More precisely, the therapeutic energy generator 268 supplies a therapy start signal to the observation unit 271 in Step S177. In Step S178, the ultrasonic image the ultrasonic probe 212 applies ultrasonic waves, whereby the ultrasonic imaging apparatus 215 transfers an image signal to the observation unit 271.

In Step S180, the luminances at the four measuring points (a) to (d) are monitored. In Step S181, it is determined whether the luminances have exceeded the reference values Ls, respectively. If NO, the operation returns to Step S178. If YES, the operation goes to Step S182, in which the therapy is terminated. Then, in Step S183, the indicator means 285 of the observation unit 271 informs that the therapy has been terminated.

In the thirty-fifth embodiment, the therapy is automatically terminated in the same way as in the twenty-fifth embodiment. The influence of the therapy energy on the living tissues in the patient is therefore minimized. Further, the affected region can be reliably treated in its entirety, because the therapy is terminated when the luminances exceed the reference luminances Ls at the four measuring points (a) to (d) set around the image Hj of the affected region.

In the thirty-fifth embodiment, the ultrasonic imaging apparatus 215 of the same type as the one incorporated in the twenty-second embodiment (FIG. 40) is used as an observation means for detecting the position of the therapeutic applicator. The ultrasonic imaging apparatus 215 can be used in the other embodiments, as well.

Utilizing a component or components of any other embodiment can modify each of the embodiments described above. For instance, in the therapeutic system according to the thirty-fifth embodiment (FIGS. 67 to 69), that incorporates the ultrasonic imaging apparatus 215 the therapeutic energy generator 268 may be automatically turn on and off as in the twenty-sixth embodiment (FIG. 48).

The present invention is not limited to the embodiments described above. Various changes and modifications can be made, without departing the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A therapeutic system comprising:
   a therapeutic applicator adapted to be inserted into a body cavity and to apply therapeutic energy to treat living tissues present in the body cavity;
   an imaging apparatus that indicates a position which the therapeutic applicator takes in the body cavity, and that outputs position data representing the position of the therapeutic applicator, said imaging apparatus also being adapted to produce an image of the living tissues present in the body cavity; and
   a control unit that controls the therapeutic energy applied from the therapeutic applicator to the living tissues based on the position data outputted by the imaging apparatus so as to decrease an output of the therapeutic applicator or entirely inhibit the therapeutic applicator from applying therapeutic energy when the imaging apparatus is operated to obtain an image of the living tissues present in the body cavity;

wherein the control unit determines a rate of treatment of the living tissues based on changes in images produced by the imaging apparatus, and changes values set in the therapeutic applicator in accordance with the determined rate of treatment.

2. A therapeutic system comprising:

a therapeutic applicator adapted to be inserted into a body cavity and to apply therapeutic energy to treat living tissues present in the body cavity;

an imaging apparatus that indicates a position which the therapeutic applicator takes in the body cavity, said imaging apparatus also being adapted to produce an image of the living tissues present in the body cavity; and a control unit that controls the therapeutic energy applied from the therapeutic applicator to the living tissues so as to decrease an output of the therapeutic applicator or entirely inhibit the therapeutic applicator from applying therapeutic energy when the imaging apparatus is operated to obtain an image of the living tissues present in the body cavity;

wherein the control unit determines a rate of treatment of the living tissues based on changes in images produced by the imaging apparatus, and changes values set in the therapeutic applicator in accordance with the determined rate of treatment.

3. A therapeutic system comprising:

a therapeutic applicator adapted to be inserted into a body cavity and to apply therapeutic energy to treat living tissues present in the body cavity;

an imaging apparatus that indicates a position which the therapeutic applicator takes in the body cavity, and that outputs position data representing the position of the therapeutic applicator, said imaging apparatus also being adapted to produce an image of the living tissues present in the body cavity; and a control unit that controls the therapeutic energy applied from the therapeutic applicator to the living tissues based on the position data outputted by the imaging apparatus so as to decrease an output of the therapeutic applicator or entirely inhibit the therapeutic applicator from applying therapeutic energy when the imaging apparatus is operated to obtain an image of the living tissues present in the body cavity;

wherein the therapeutic applicator comprises a therapeutic section adapted to contact the living tissues, and the control unit supplies a tissue-separating current to the living tissues to remove the tissues from the therapeutic section when the therapeutic applicator stops applying the therapeutic energy.

4. A therapeutic system comprising:

a therapeutic applicator adapted to be inserted into a body cavity and to apply therapeutic energy to treat living tissues present in the body cavity;

an imaging apparatus that indicates a position which the therapeutic applicator takes in the body cavity, said imaging apparatus also being adapted to produce an image of the living tissues present in the body cavity; and a control unit that controls the therapeutic energy applied from the therapeutic applicator to the living tissues so as to decrease an output of the therapeutic applicator or entirely inhibit the therapeutic applicator from applying therapeutic energy when the imaging apparatus is operated to obtain an image of the living tissues present in the body cavity;

wherein the therapeutic applicator comprises a therapeutic section adapted to contact the living tissues, and the control unit supplies a tissue-separating current to the living tissues to remove the tissues from the therapeutic section when the therapeutic applicator stops applying the therapeutic energy.

5. A therapeutic system comprising:

a therapeutic applicator adapted to be inserted into a body cavity and to apply therapeutic energy to treat living tissues present in the body cavity;

an imaging apparatus that indicates a position which the therapeutic applicator takes in the body cavity, and that outputs position data representing the position of the therapeutic applicator, said imaging apparatus also being adapted to produce an image of the living tissues present in the body cavity; and a control unit that controls the therapeutic energy applied from the therapeutic applicator to the living tissues based on the position data outputted by the imaging apparatus so as to decrease an output of the therapeutic applicator or entirely inhibit the therapeutic applicator from applying therapeutic energy when the imaging apparatus is operated to obtain an image of the living tissues present in the body cavity;

wherein the control unit controls the imaging apparatus to display an image of the living tissues present in the body cavity, after decreasing the output of the therapeutic applicator or entirely inhibiting the therapeutic applicator from applying therapeutic energy;

wherein the control unit determines a rate of treatment of the living tissues based on changes in images produced by the imaging apparatus, and changes values set in the therapeutic applicator in accordance with the determined rate of treatment;

wherein said imaging apparatus comprises an MRI apparatus, and the control unit supplies an MRI start signal and an MRI stop signal to the MRI apparatus;

wherein the control unit supplies MRI parameters to the MRI apparatus;

wherein the control unit is adapted to receive an MRI signal from the MRI apparatus;

wherein the control unit supplies an output start signal, an output stop signal, and an output-level setting signal to the therapeutic applicator; and wherein the therapeutic applicator comprises a therapeutic section adapted to contact the living tissues, and the control unit supplies a tissue-separating current to the living tissues to remove the tissues from the therapeutic section when the therapeutic applicator stops applying the therapeutic energy.

* * * * *